US008058427B2

(12) United States Patent
Hsieh et al.

(10) Patent No.: US 8,058,427 B2
(45) Date of Patent: Nov. 15, 2011

(54) COUMARIN COMPOUNDS AND THEIR USE FOR TREATING CANCER

(75) Inventors: Hsing-Pang Hsieh, Taipei (TW); Jang-Yang Chang, Tainan (TW); Ching-Chuan Kuo, Tainan (TW); Yu-Sheng Chao, Monmouth Junction, NJ (US)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 12/481,783

(22) Filed: Jun. 10, 2009

(65) Prior Publication Data
US 2009/0312317 A1    Dec. 17, 2009

Related U.S. Application Data

(60) Provisional application No. 61/060,917, filed on Jun. 12, 2008.

(51) Int. Cl.
| C07D 413/12 | (2006.01) |
| C07D 405/12 | (2006.01) |
| C07D 217/04 | (2006.01) |
| C07D 401/12 | (2006.01) |
| C07D 493/02 | (2006.01) |

(52) U.S. Cl. ........ 544/150; 544/375; 546/146; 546/197; 548/454; 549/387

(58) Field of Classification Search ........................ None
See application file for complete search history.

(56) References Cited

U.S. PATENT DOCUMENTS

| 4,542,102 | A | 9/1985 | Dattagupta et al. |
| 4,713,326 | A | 12/1987 | Dattagupta et al. |
| 4,794,073 | A | 12/1988 | Dattagupta et al. |
| 4,853,327 | A | 8/1989 | Dattagupta |
| 4,950,588 | A | 8/1990 | Dattagupta |
| 4,994,263 | A | 2/1991 | Lang et al. |
| 5,372,929 | A | 12/1994 | Cimino et al. |
| 5,565,320 | A | 10/1996 | Cimino et al. |
| 6,242,188 | B1 | 6/2001 | Dattagupta et al. |
| 6,379,930 | B1 | 4/2002 | Dattagupta et al. |
| 6,448,047 | B2 | 9/2002 | Dattagupta et al. |
| 2001/0031473 | A1 | 10/2001 | Dattagupta et al. |
| 2002/0061537 | A1 | 5/2002 | Dattagupta et al. |

FOREIGN PATENT DOCUMENTS
| EP | 0130523 | 6/1988 |
| EP | 0210449 | 7/1993 |

OTHER PUBLICATIONS

N.A. Farag. Bull. Fac. Pharm. Cairo Univ., vol. 44, No. 1 (2006).*
Sibirtsev et al. Biochemistry (Moscow), vol. 70, No. 7, 2005.*
Geetanjali et al., "Synthesis of 2-Aroyl-3-phenylfuranobenzopyrones," Indian Journal of Chemistry 22B:164-165 (1983).
Pathak et al., Production of Active Oxygen Species $^1O_2$ and $O_2^-$) By Psoralens and Ultraviolet Radiation (320-400nm), Biochimica et Biophysica Acta 798:115-126 (1984).
Guilet et al., "Novel Cytotoxic 4-Phenylfuranocoumarins from *Calophyllum dispar*" J. Nat. Prod/ 64:563-568 (2001).
Bhayani et al., "Furocoumarin Studies. Part-1. New Synthesis of 4-Methylangelicin and Angelicin," J. Indian Chem. Soc. 67:71-72 (1990).
Chaturvedula et al., "New Cytotoxic Coumarins and Prenylated Benzophenone Derivatives from the Bark of *Ochrocarpos punctatus* from the Madagascar Rainforest," J. Nat. Prod. 65:965-972 (2002).
Caffieri et al., "Difurocoumarins, Psoralen Analogs: Synthesis and DNA Photobinding," Z. Naturforsch 50b:1257-1264 (1995).
Baccichetti et al., "New Benzopsoralen Derivative: T2 Phage Inactivation," Med. Biol. Environn., 23(1):7-11 (1995).
Isaacs et al., "Post-PCR Sterilization: Development and Application to an HIV-1 Diagnostic Assay," Nuclei Acids Research, vol. 19, No. 1:109-116 (1990).
Versailles et al., "Photochemical Sterilization of 3SR Reactions," PCR Methods and Applications, 3:151-158 (1993).
Zmudzk et al., "Activation of the Human Immunodeficiency Virus Promoter by UVA Radiation in Combination with Psoralens or Angelicins," Photochemistry and Photobiology, 58(2):226-232 (1993).
Miolo et al., "Antiretroviral Activity of Furocoumarins Plus UVA Light Detected by a Replication-Defective Retrovirus," Journal of Photochemistry and Photobiology, 26:241-247 (1994).
Joshi et al., "Production on Singlet Oxygen and Superoxide Radicals by Psoralens and Their Biological Significance," Biochemical and Biophysical Research Communication, 112(2):638-646 (1983).
Chen et al., "Photosensitized Cross-Linking and Cleavage of pBR322 and M13 DNA: Comparison 4,4;',6-trimethylangelicin and 3-carbethoxypsoralen," J. Photochen. Photobiol. B: Biol., 22:51-57 (1994).
Czyz et al., "Comparison of Inhibitory Effects of Mono- and Diadducts of Furocoumarins on the Transcriptional Template Activity of Phage T7 DNA," Studia Biophysica, 135(3):147-154 (1990).
van Iperen et al., "The Lack of Efficacy of 4,6,4'-Trimethylangelicin to Induce Immune Suppression in an Animal Model for Photopheresis: A Comparison with 8-MOP," Photochemistry and Photobiology, 63(5):577-582 (1996).

(Continued)

*Primary Examiner* — Rebecca Anderson
*Assistant Examiner* — Alicia L Otton
(74) *Attorney, Agent, or Firm* — Occhiuti Rohlicek & Tsao LLP

(57) ABSTRACT

Coumarin compounds of formula (I):

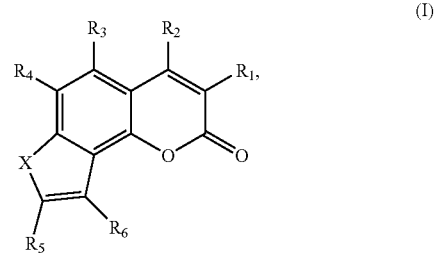

wherein $R_1$, $R_2$, $R_3$, $R_4$, $R_5$, $R_6$, and X are defined herein. Also disclosed is a method for treating cancer with coumarin compounds.

5 Claims, No Drawings

OTHER PUBLICATIONS

Rao et al., "Studies on the Synthesis of Furocoumarins. Part-XXX. A Reinvestigation of Claisen Rearrangement of 7-Cinnamyloxy-4-methylcoumarin," J. Indian Chem. Soc. 69:203-206 (1992).

Kawase et al., "Synthetic Studies on the Benzofuran Derivatives. VII. A New Synthesis of Angelicin and 4-Methylangelicin,"vol. 35, No. 1, pp. 149-151 Jan. 1962.

Rao et al., "Furocoumarins: Part 34-Synthesis and stereochemistry of Dihydrofurocoumarins," Indian Journal of Chemistry, 31B:488-491 (1992).

Traven et al., "Synthesis of New Difurocoumarins," Chemistry of Heterocyclic Compounds, 39(7):866-871 (2003).

Sibirtsev et al., "Spectral Study of Interactions of 4,8,4—Trimethylpsoralen and 4,4—Dinethylangelicin Dyes with DNA," Biochemistry (Moscow) 70(7):822-832 (2005).

Sibirtsev et al., "Dependence of Fluorescence Properties of Compounds from Psoralen, Angelicin, and Carbazole Series on the Character of Their Terminal Substituents," Russian Journal of Organic Chemistry, 39(6):881-889 (2003).

V.S. Sibirtsev, "Fluorescent DNA Probes: Study of Mechanisms of Changes in Spectral Properties and Features of Practical Application," Biochemistry (Moscow), 72(8):1090-1106 (2007).

Tolmachev et al., "New Synthesis of 8-Alkoxycarbonylangelicins" Russian Journal of Organic Chemistry, 37(7):1008-1012 (2001).

Salvi et al., "Studies in Furan Derivatives: Part V. Syntheses of Some Furocoumarins," Jour. Indian Chem. Soc., 45(5):439-445 (1968).

Traven et al., "Electronic Structure of P Systems: XX. Electronic Structure a Keto-Enoltautomerism of dihydrofuro[2,3-h]coumarin-9-ones by photoelectron spectroscopy," Russian Journal of General Chemistry, 71(6)m pp. 945-949 (2001).

Santana et al., "Furocoumarins in Medicinal Chemistry. Synthesis, natural occurrence and biological activity," Current Medicinal Chemistry, 11(24) pp. 3239-3261 (2004).

* cited by examiner

COUMARIN COMPOUNDS AND THEIR USE FOR TREATING CANCER

CROSS-REFERENCE TO RELATED APPLICATION

This application claims the benefit of the priority pursuant to 35 U.S.C. §119(e) of U.S. Provisional Patent Application No. 61/060,917, filed Jun. 12, 2008. The content of the prior application is incorporated herein by its entirety.

BACKGROUND

Cancer is a leading cause of death in developed countries. Despite continuing advances in diagnosis and treatment regimens, most existing treatment methods have undesirable side effects and limited efficacy. Treatment of cancer is complicated by the variety of mechanisms involved in the formation and metastasis of tumors. Many of them are still not well understood. Chemotherapy is a major option for the first-line treatment in cancers such as leukemia and second-line treatment for cancers such as refractory solid tumor. Most current anticancer drugs are small molecule chemicals.

SUMMARY

This invention is based on the discovery that certain coumarin compounds have potent anticancer activity. Thus, this invention relates to coumarin compounds and to their use in cancer treatment.

In one aspect, this invention features a coumarin compound of formula (I):

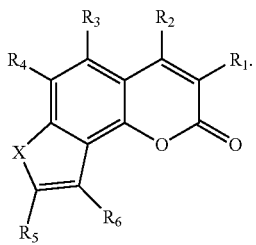

(I)

In formula (I), each of $R_1$, $R_2$, $R_3$, and $R_4$, independently, is H, alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, $C(O)R_a$, $C(O)OR_a$, $C(O)NR_aR_b$, $C(S)R_b$, or $C(NR_b)R_a$, in which each of $R_a$ and $R_b$, independently, is H, alkyl, alkenyl, alkynyl, hydroxy, alkoxy, amino, cycloalkyl, cycloalkenyl, heterocycloalkyl, heterocycloalkenyl, aryl, or heteroaryl; or $R_1$ and $R_2$, together with the carbon atoms to which they are bonded, are cycloalkenyl, heterocycloalkenyl, aryl, or heteroaryl; or $R_2$ and $R_3$, together with the carbon atoms to which they are bonded, are cycloalkenyl or heterocycloalkenyl; or $R_3$ and $R_4$, together with the carbon atoms to which they are bonded, are cycloalkenyl, heterocycloalkenyl, aryl, or heteroaryl; $R_5$ is alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, $C(O)R_c$, $C(O)OR_c$, $C(O)NR_cR_d$, $C(S)R_d$, or $C(NR_d)R_c$, in which each of $R_c$ and $R_d$, independently, is H, alkyl, alkenyl, alkynyl, hydroxy, alkoxy, amino, cycloalkyl, cycloalkenyl, heterocycloalkyl, heterocycloalkenyl, heterocy cloalkenyl, aryl, or heteroaryl; $R_6$ is cycloalkyl, cycloalkenyl, heterocycloalkyl, heterocycloalkenyl, heteroaryl, halo, nitro, cyano, amino, hydroxy, aryloxy, $C(O)R_c$, $C(O)OR_c$, $C(O)NR_cR_d$, $C(S)R_d$, $C(NR_d)R_c$, or aryl substituted with alkyl at the 3-position of the aryl, halo, nitro, cyano, amino, carboxyl, cycloalkyl, aryl, or heteroaryl; and X is O, S, or $N(R_e)$, in which $R_e$ is H, alkyl, cycloalkyl, heterocycloalkyl, aryl, or heteroaryl.

One subset of the above-described coumarin compounds includes those in which $R_5$ is alkyl, cycloalkyl, aryl, halo, $C(O)R_c$, $C(O)OR_c$, $C(O)NR_cR_d$, $C(S)R_d$, or $C(NR_d)R_c$. In these compounds, $R_5$ can be $C(O)R_cC(S)R_d$, or $C(NR_d)R_c$, in which $R_c$ can be aryl or heteroaryl and $R_d$ can be amino or hydroxy; $R_6$ can be cycloalkyl, heteroaryl, or aryl substituted with alkyl at the 3-position of the aryl, halo, nitro, cyano, amino, cycloalkyl, aryl, or heteroaryl (e.g., phenyl substituted with alkyl at the 3-position of the phenyl, halo, nitro, or amino); each of $R_1$, $R_2$, $R_3$, and $R_4$, independently, can be H, alkyl, alkenyl, cycloalkyl, cycloalkenyl, heterocycloalkyl, aryl, hydroxy, alkoxy, halo, cyano, nitro, or C(O)H; or X can be O.

Another subset of the above-described coumarin compounds includes those in which $R_6$ is cycloalkyl, heteroaryl, or aryl substituted with nitro, cyano, amino, cycloalkyl, or heteroaryl. In these compounds, $R_5$ can be $C(O)R_cC(S)R_d$, or $C(NR_d)R_c$, in which $R_c$ can be aryl or heteroaryl and $R_d$ can be amino or hydroxy; each of $R_1$, $R_2$, $R_3$, and $R_4$, independently, can be H, alkyl, alkenyl, cycloalkyl, cycloalkenyl, heterocycloalkyl, aryl, hydroxy, alkoxy, halo, cyano, nitro, or C(O)H; or X can be O.

Still another two subsets of the above-described coumarin compounds include those in which X is O and those in which each of $R_1$, $R_2$, $R_3$, and $R_4$, independently, is H, alkyl, alkenyl, cycloalkyl, cycloalkenyl, heterocycloalkyl, aryl, hydroxy, alkoxy, halo, cyano, nitro, or C(O)H.

The term "alkyl" refers to a straight or branched monovalent hydrocarbon containing, unless otherwise stated, 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkylene" refers to a straight or branched bivalent hydrocarbon, containing 1-20 carbon atoms (e.g., $C_1$-$C_{10}$). Examples of alkylene include, but are not limited to, methylene and ethylene. The term "alkenyl" refers to a straight or branched monovalent or bivalent hydrocarbon containing 2-20 carbon atoms (e.g., $C_2$-$C_{10}$) and one or more double bonds. Examples of alkenyl include, but are not limited to, ethenyl, propenyl, propenylene, allyl, and 1,4-butadienyl. The term "alkynyl" refers to a straight or branched monovalent or bivalent hydrocarbon containing 2-20 carbon atoms (e.g., $C_2$-$C_{10}$) and one or more triple bonds. Examples of alkynyl include, but are not limited to, ethynyl, ethynylene, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, iso-propoxy, n-butoxy, iso-butoxy, sec-butoxy, and tert-butoxy. The term "acyloxy" refers to an —O—C(O)—R radical in which R can be H, alkyl, alkenyl, alkynyl, cycloalkyl, cycloalkenyl, heterocycloalkyl, heterocycloalkenyl, aryl, or heteroaryl. The term "amino" refers to $NH_2$, alkylamino, or arylamino. The term "alkylamino" refers to an —N(R)-alkyl radical in which R can be H, alkyl, alkenyl, alkynyl, cycloalkyl, cycloalkenyl, heterocycloalkyl, heterocycloalkenyl, aryl, or heteroaryl. The terms "amido" and "carbamido" refer to —NRC(O)R' and —C(O)NRR' radicals respectively, in which each of R and R', independently, can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent or bivalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, 1,4-cyclohexylene, cycloheptyl, cyclooctyl, and adamantine. The term "cycloalkenyl" refers to a monovalent or bivalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent or bivalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent or bivalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "arylene" refers to a bivalent 6-carbon monocyclic, 10-carbon bicyclic, 14-carbon tricyclic aromatic ring system. The term "aryloxyl" refers to an —O-aryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Alkyl, alkenyl, alkynyl, cycloalkyl, heterocycloalkyl, cycloalkenyl, heterocycloalkenyl, amino, aryl, heteroaryl, alkylene, arylene, and heteroarylene mentioned above include both substituted and unsubstituted moieties. Possible substituents on amino, cycloalkyl, heterocycloalkyl, cycloalkenyl, heterocycloalkenyl, aryl, arylene, heteroaryl, and heteroarylene include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)NH$_2$), carboxyl (—COOH), and carboxylic ester. On the other hand, possible substituents on alkyl, alkenyl, alkynyl, or alkylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In another aspect, this invention relates to a coumarin compound of formula (I):

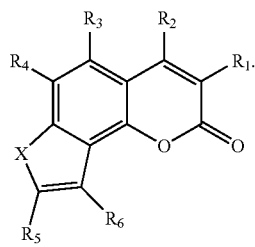

(I)

In formula (I), each of $R_1$, $R_2$, $R_3$, and $R_4$, independently, is H, alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, C(O)$R_a$, C(O)O$R_a$, C(O)NR$_a$R$_b$, C(S)R$_b$, or C(NR$_b$)R$_a$, in which each of R$_a$ and R$_b$, independently, is H, alkyl, alkenyl, alkynyl, hydroxy, alkoxy, amino, cycloalkyl, cycloalkenyl, heterocycloalkyl, heterocycloalkenyl, aryl, or heteroaryl; or $R_1$ and $R_2$, together with the carbon atoms to which they are bonded, are cycloalkenyl, heterocycloalkenyl, aryl, or heteroaryl; or $R_2$ and $R_3$, together with the carbon atoms to which they are bonded, are cycloalkenyl or heterocycloalkenyl; or $R_3$ and $R_4$, together with the carbon atoms to which they are bonded, are cycloalkenyl, heterocycloalkenyl, aryl, or heteroaryl; $R_5$ is alkyl substituted with aryl or hydroxy, alkenyl, cycloalkyl, cycloalkenyl, heterocycloalkyl, heterocycloalkenyl, heteroaryl, halo, nitro, cyano, amino, hydroxy, alkoxy, aryloxy, C(O)R$_c$, C(O)OR$_c$, C(O)NR$_d$R$_e$, C(S)R$_d$, or C(NR$_e$)R$_d$, in which R$_c$ is cycloalkyl, cycloalkenyl, heterocycloalkyl, heterocycloalkenyl, heteroaryl, or aryl substituted with alkyl, halo, nitro, cyano, amino, amido, cycloalkyl, aryl, heteroaryl, hydroxy, alkoxy, acyloxy, silyloxy, or phosphate at the 3-position of the aryl, and each of R$_d$ and R$_e$, independently, is H, alkyl, alkenyl, alkynyl, hydroxy, alkoxy, amino, cycloalkyl, cycloalkenyl, heterocycloalkyl, heterocycloalkenyl, aryl, or heteroaryl; $R_6$ is alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, or aryloxy; and X is O, S, or N(R$_f$), in which R$_f$ is H, alkyl, cycloalkyl, heterocycloalkyl, aryl, or heteroaryl.

One subset of the just-described coumarin compounds includes those in which $R_6$ is aryl or heteroaryl. In these compounds, $R_6$ can be phenyl; $R_5$ can be C(O)R$_c$, in which R$_c$ can be heteroaryl or aryl substituted with alkyl, halo, hydroxy, or alkoxy at the 2- or 3-position of the aryl; $R_5$ can be C(S)R$_d$, or C(NR$_e$)R$_d$, in which R$_d$ can be aryl or heteroaryl and R$_e$ can be amino or hydroxy; $R_2$ can be methyl; or X can be O.

In yet another aspect, this invention relates to a coumarin compound of formula (I):

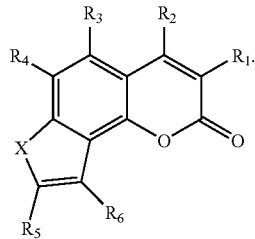

(I)

In formula (I), each of $R_1$, $R_3$, and $R_4$, independently, is H, alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, $C(O)R_a$, $C(O)OR_a$, $C(O)NR_aR_b$, $C(S)R_b$, or $C(NR_b)R_a$, in which each of $R_a$ and $R_b$, independently, is H, alkyl, alkenyl, alkynyl, hydroxy, alkoxy, amino, cycloalkyl, cycloalkenyl, heterocycloalkyl, heterocycloalkenyl, aryl, or heteroaryl; $R_2$ is H, $C_2$-$C_{10}$ alkyl, alkenyl, alkynyl, cycloalkyl, cycloalkenyl, heterocycloalkyl, heterocycloalkenyl, heteroaryl, halo, nitro, cyano, amino, hydroxy, alkoxy, aryloxy, $C(O)R_a$, $C(O)OR_a$, $C(O)NR_aR_b$, $C(S)R_b$, or $C(NR_b)R_a$; or $R_1$ and $R_2$, together with the carbon atoms to which they are bonded, are cycloalkenyl, heterocycloalkenyl, aryl, or heteroaryl; or $R_2$ and $R_3$, together with the carbon atoms to which they are bonded, are cycloalkenyl or heterocycloalkenyl; or $R_3$ and $R_4$, together with the carbon atoms to which they are bonded, are cycloalkenyl, heterocycloalkenyl, aryl, or heteroaryl; $R_5$ is $C(O)R_c$, $C(O)OR_c$, $C(O)NR_dR_e$, $C(S)R_d$, or $C(NR_e)R_d$, in which, $R_c$ is aryl or heteroaryl, and each of $R_d$ and $R_e$, independently, is H, alkyl, alkenyl, alkynyl, hydroxy, alkoxy, amino, cycloalkyl, cycloalkenyl, heterocycloalkyl, heterocycloalkenyl, aryl, or heteroaryl; $R_6$ is aryl or heteroaryl; and X is O, S, or $N(R_f)$, in which $R_f$ is H, alkyl, cycloalkyl, heterocycloalkyl, aryl, or heteroaryl.

The coumarin compounds described herein include the compounds themselves, as well as their salts, their solvates, and their prodrugs, if applicable. A salt, for example, can be formed between an anion and a positively charged group (e.g., amino) on a coumarin compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a coumarin compound. Suitable cations include sodium ion, potassium ion, magnesium ion, calcium ion, and an ammonium cation such as tetramethylammonium ion. The coumarin compounds also include those salts containing quaternary nitrogen atoms. Examples of prodrugs include esters and other pharmaceutically acceptable derivatives, which, upon administration to a subject, are capable of providing active coumarin compounds.

Further, this invention relates to a method for treating cancer by administering to a subject in need thereof an effective amount of a coumarin compound of formula (I):

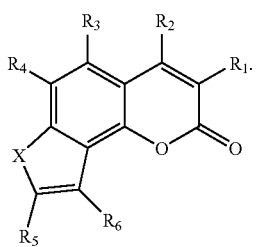

(I)

In this formula, each of $R_1$, $R_2$, $R_3$, and $R_4$, independently, is H, alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, $C(O)R_a$, $C(O)OR_a$, $C(O)NR_aR_b$, $C(S)R_b$, or $C(NR_b)R_a$, in which each of $R_a$ and $R_b$, independently, is H, alkyl, alkenyl, alkynyl, hydroxy, alkoxy, amino, cycloalkyl, cycloalkenyl, heterocycloalkyl, heterocycloalkenyl, aryl, or heteroaryl; or $R_1$ and $R_2$, together with the carbon atoms to which they are bonded, are cycloalkenyl, heterocycloalkenyl, aryl, or heteroaryl; or $R_2$ and $R_3$, together with the carbon atoms to which they are bonded, are cycloalkenyl or heterocycloalkenyl; or $R_3$ and $R_4$, together with the carbon atoms to which they are bonded, are cycloalkenyl, heterocycloalkenyl, aryl, or heteroaryl; $R_5$ is H, alkyl substituted with aryl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, $C(O)R_c$, $C(O)OR_c$, $C(O)NR_cR_d$, $C(S)R_d$, or $C(NR_d)R_c$, in which each of $R_c$ and $R_d$, independently, is H, alkyl, alkenyl, alkynyl, hydroxy, alkoxy, amino, cycloalkyl, cycloalkenyl, heterocycloalkyl, heterocycloalkenyl, aryl, or heteroaryl; $R_6$ is H, alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, $C(O)R_c$, $C(O)OR_c$, $C(O)NR_cR_d$, $C(S)R_d$, or $C(NR_d)R_c$; or $R_5$ and $R_6$, together with the carbon atoms to which they are bonded, are cycloalkenyl, heterocycloalkenyl, aryl, or heteroaryl; and X is O, S, or $N(R_e)$, in which $R_e$ is H, alkyl, cycloalkyl, heterocycloalkyl, aryl, or heteroaryl. Examples of cancer include, but are not limited to, nasopharyngeal carcinoma, cervical carcinoma, gastric carcinom, breast carcinoma, colorectal carcinoma, non-small cell lung carcinoma, lymphoma, leukemia, and hepatocellular carcinoma.

Referring to formula (I), a subset of the just-described compounds are those in which $R_5$ is alkyl substituted with aryl or hydroxy, cycloalkyl, aryl, halo, $C(O)R_c$, or $C(O)OR_c$. In these compounds, $R_5$ can be alkyl substituted with aryl or $C(O)R_c$, in which $R_c$ can be aryl or heteroaryl; $R_6$ can be aryl or heteroaryl; $R_2$ can be alkyl or $C(O)H$; or X can be O.

Another subset of these coumarin compounds includes those in which $R_6$ is alkyl, cycloalkyl, aryl, heteroaryl. In these compounds, $R_6$ can be aryl or heteroaryl; $R_5$ can be $C(S)R_d$, or $C(NR_d)R_c$; $R_2$ can be alkyl or $C(O)H$; or X can be O.

Yet another subset of these compounds includes those in which $R_5$ is $C(S)R_d$, or $C(NR_d)R_c$. Still another two subsets of the compounds of formula (I) include those in which X is O and those in which each of $R_1$, $R_2$, $R_3$, and $R_4$, independently, is H, alkyl, aryl, heteroaryl, nitro, hydroxy, alkoxy, aryloxy, or $C(O)R_a$; or $R_1$ and $R_2$, together with the carbon atoms to which they are bonded, are cycloalkenyl, heterocycloalkenyl, aryl, or heteroaryl.

Also within the scope of this invention is a pharmaceutical composition containing one or more of the above-described coumarin compounds for use in treating cancer, as well as this therapeutic use and use of the compounds for the manufacture of a medicament for treating cancer.

8-Benzoyl-4-methyl-9-phenylcyclopenta[h]chromen-2(7H)-one and its analogs, as well as their therapeutic use as described above, are also contemplated.

The details of one or more embodiments of the invention are set forth in the description below. Other features, objects, and advantages of the invention will be apparent from the description and the claims.

DETAILED DESCRIPTION
Shown below are exemplary compounds of this invention:
Compound 1
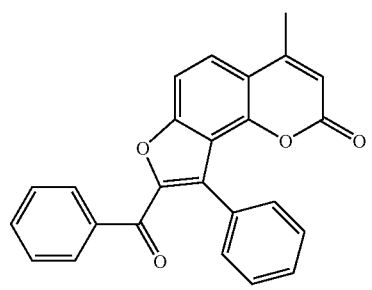
Compound 2
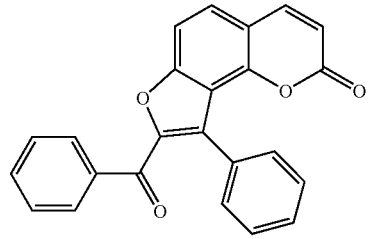
Compound 3
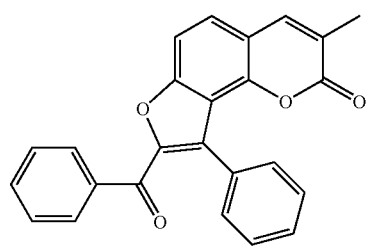
Compound 4
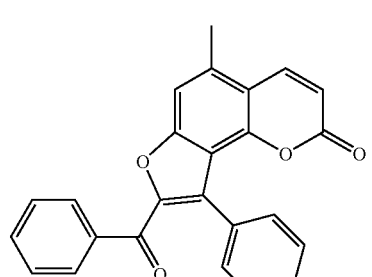
Compound 5
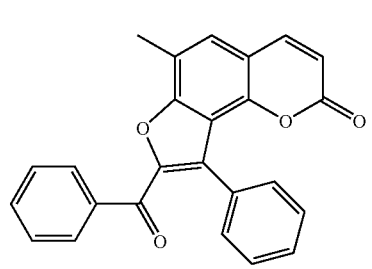
Compound 6
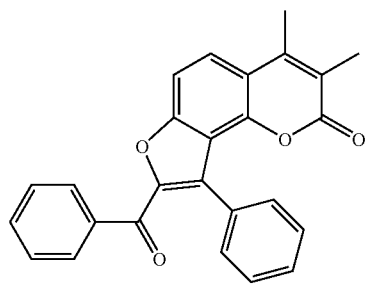
Compound 7
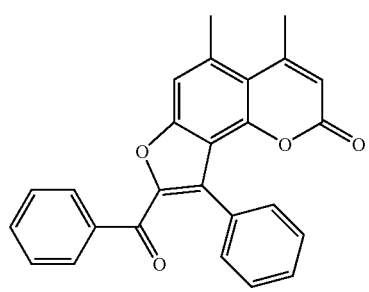
Compound 8
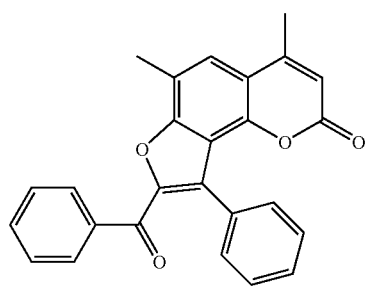
Compound 9
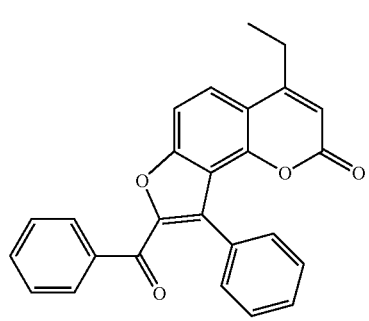
Compound 10
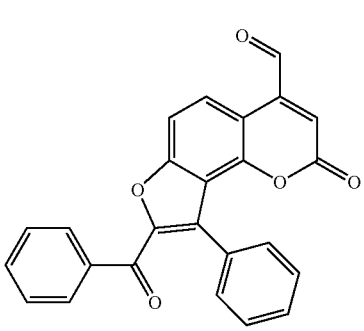

Compound 11
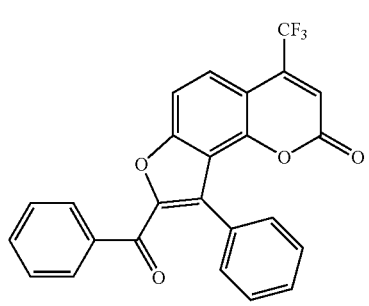
Compound 12
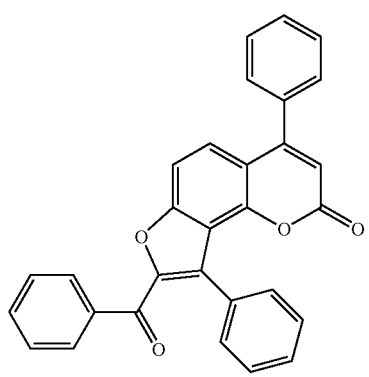
Compound 13
Compound 14
Compound 15
Compound 16
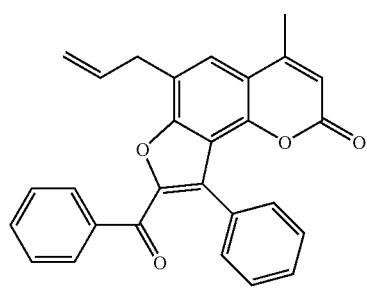
Compound 17
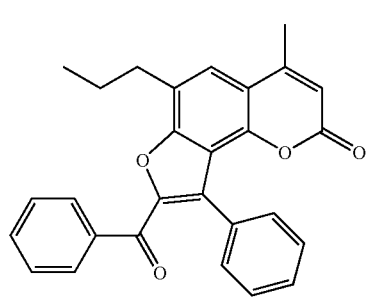
Compound 18
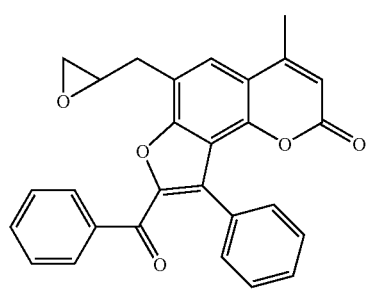
Compound 19
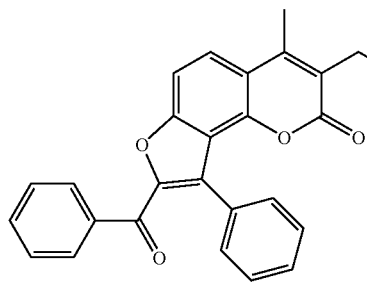
Compound 20
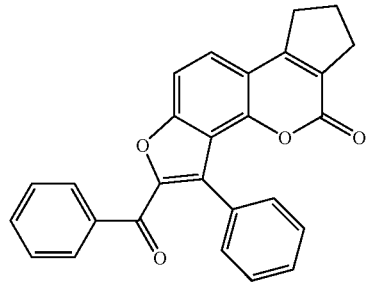

Compound 21
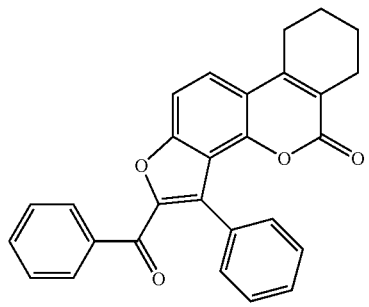
Compound 22
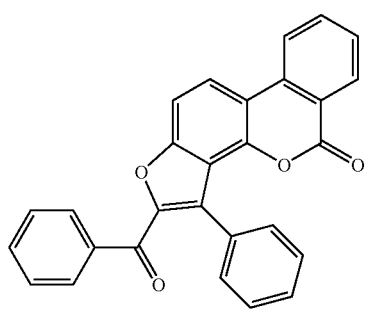
Compound 23
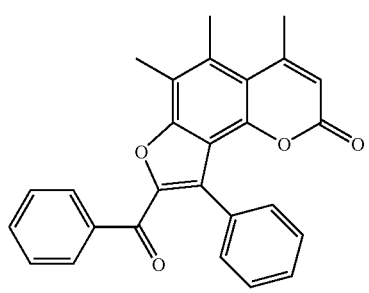
Compound 24
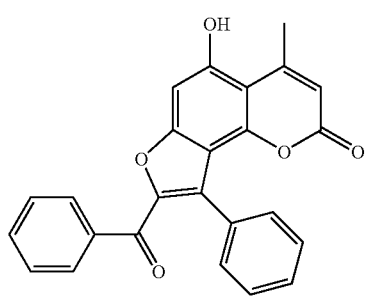
Compound 25
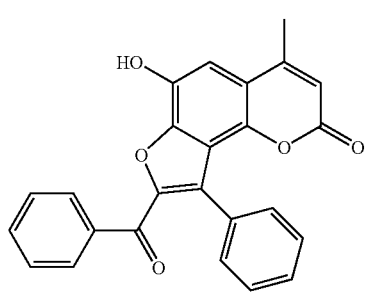
Compound 26
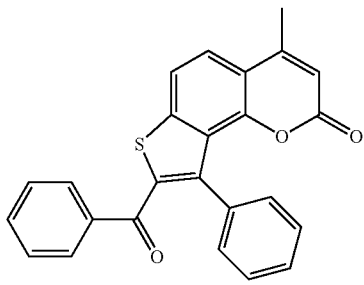
Compound 27
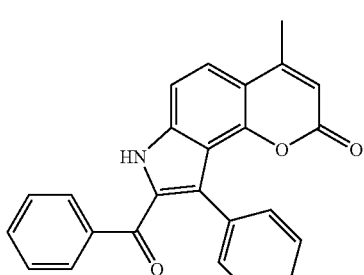
Compound 28
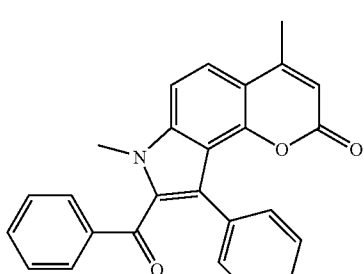
Compound 29
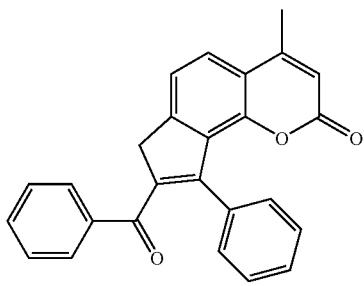
Compound 30
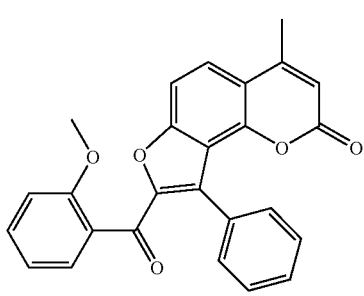

Compound 31
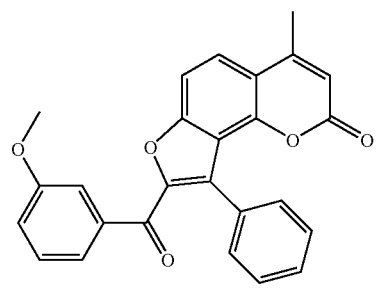
Compound 32
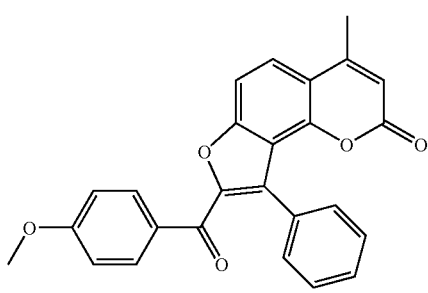
Compound 33
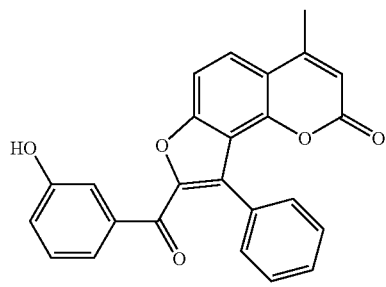
Compound 34
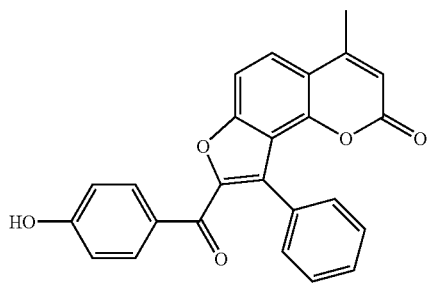
Compound 35
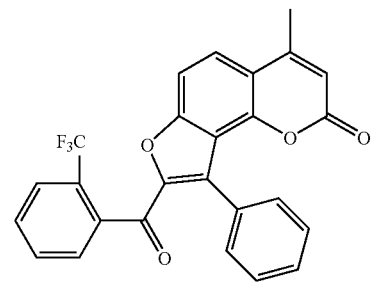
Compound 36
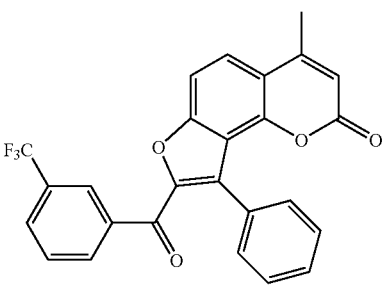
Compound 37
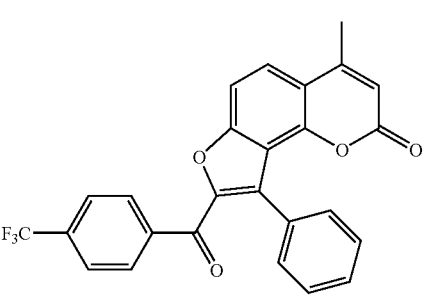
Compound 38
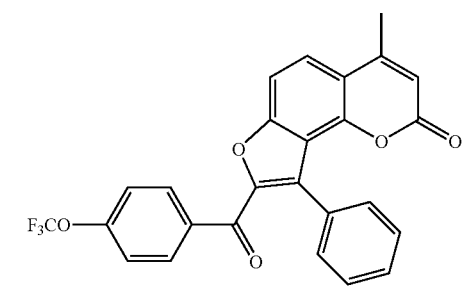
Compound 39
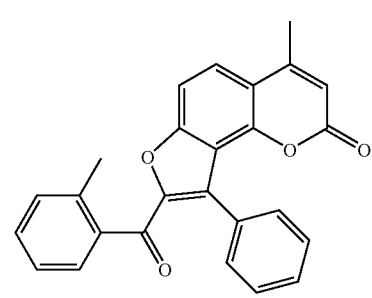
Compound 40
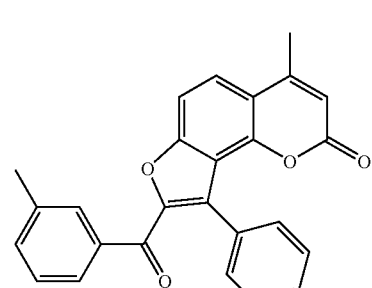

Compound 41
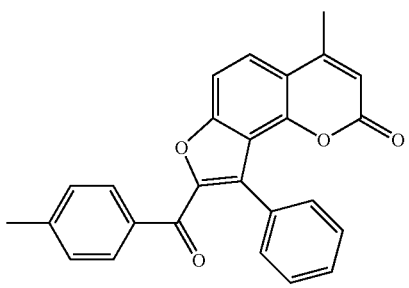
Compound 42
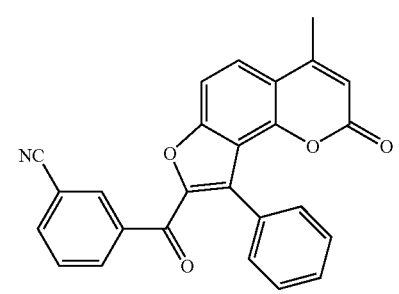
Compound 43
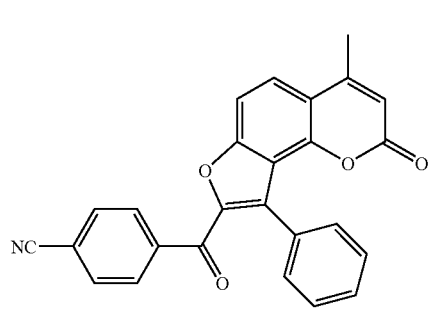
Compound 44
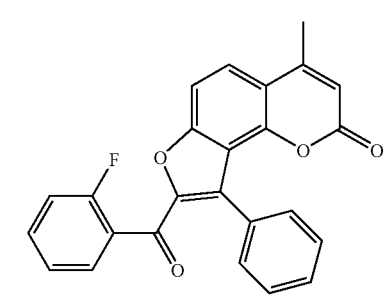
Compound 45
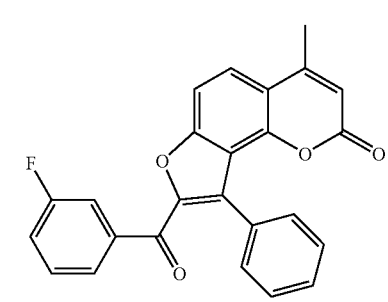
Compound 46
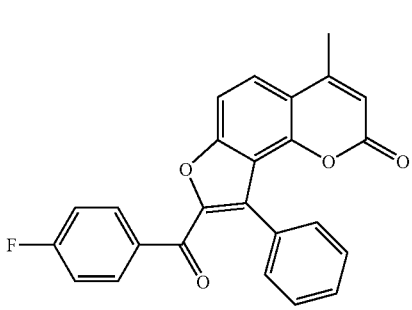
Compound 47
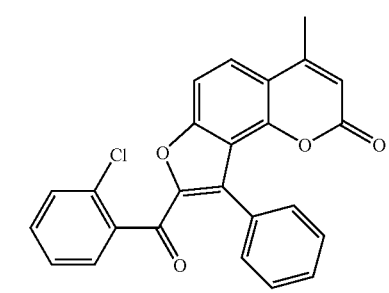
Compound 48
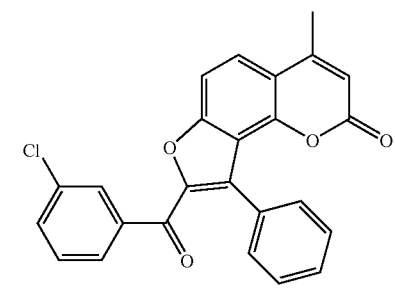
Compound 49
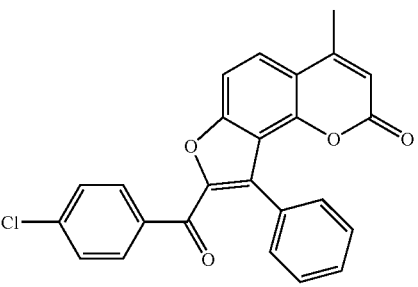
Compound 50
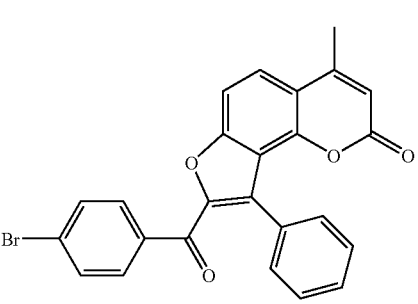

Compound 51
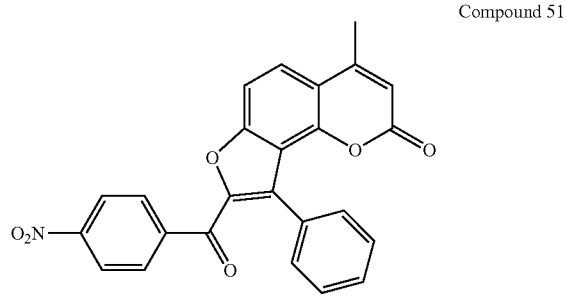
Compound 52
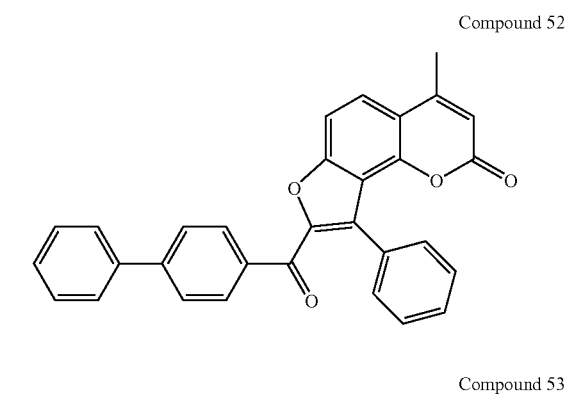
Compound 53
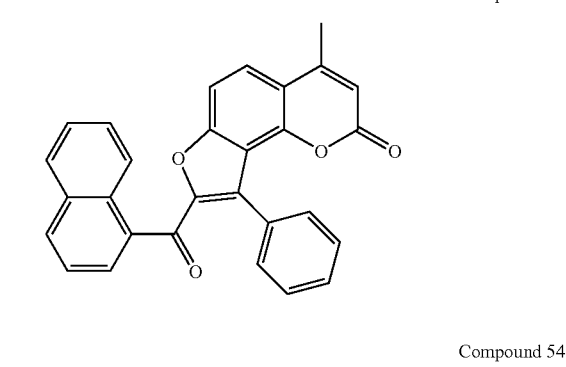
Compound 54
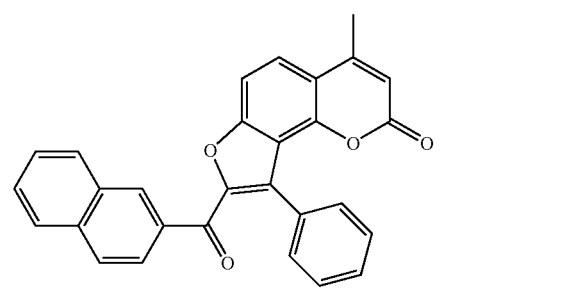
Compound 55
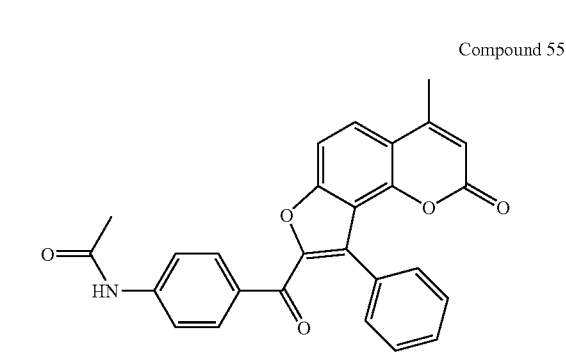
Compound 56
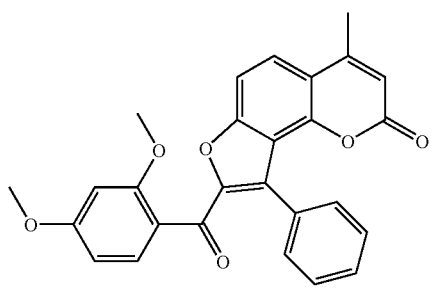
Compound 57
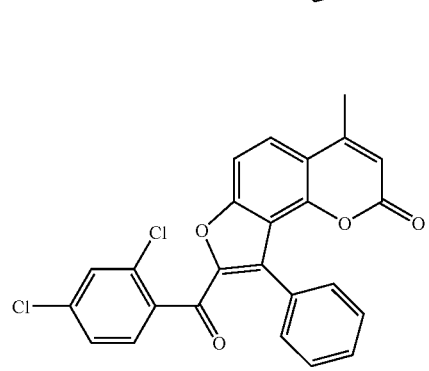
Compound 58
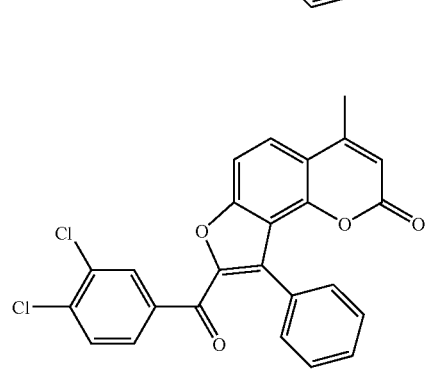
Compound 59
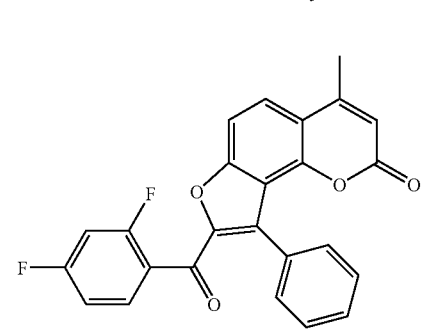
Compound 60
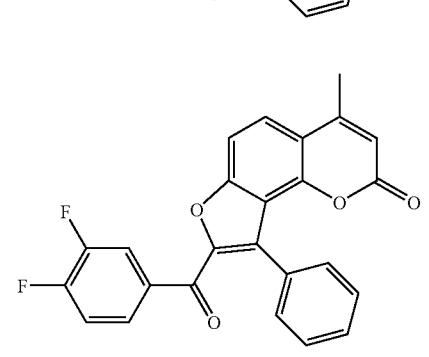

Compound 61
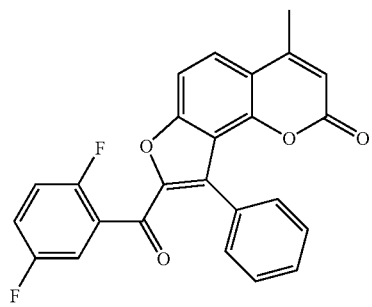
Compound 62
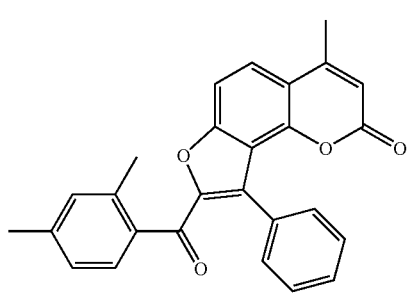
Compound 63
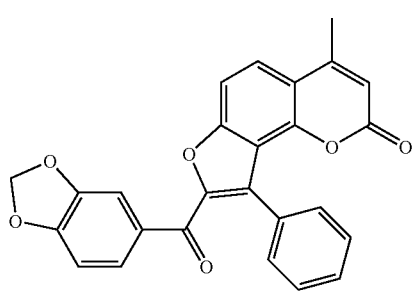
Compound 64
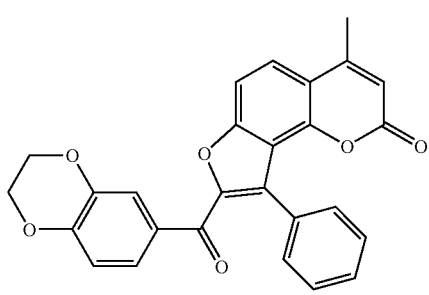
Compound 65
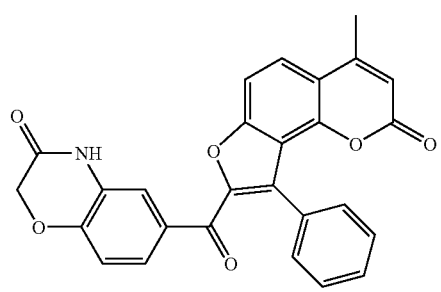
Compound 66
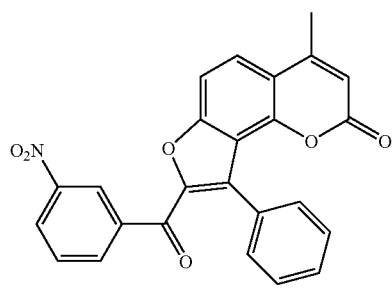
Compound 67
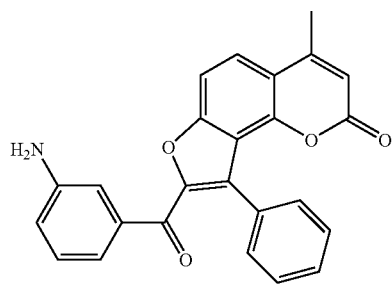
Compound 68
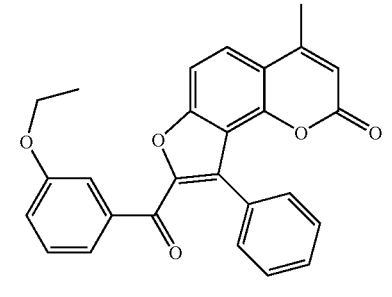
Compound 69
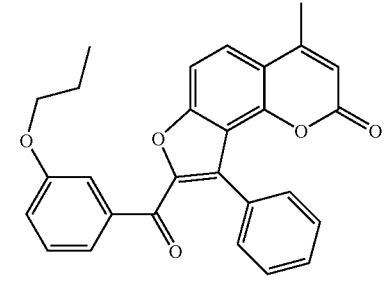
Compound 70

-continued
Compound 71
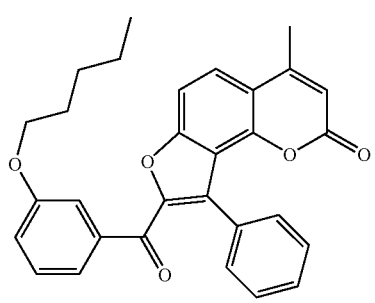
Compound 72
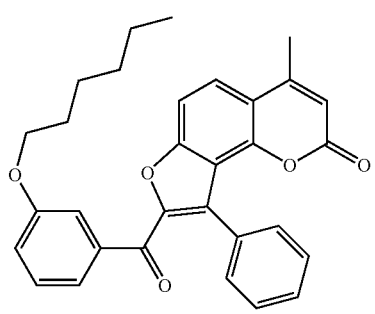
Compound 73
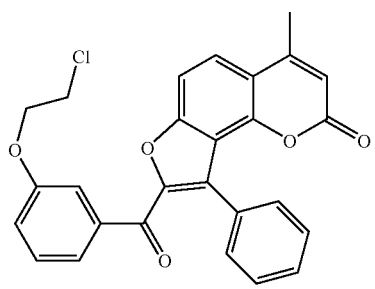
Compound 74
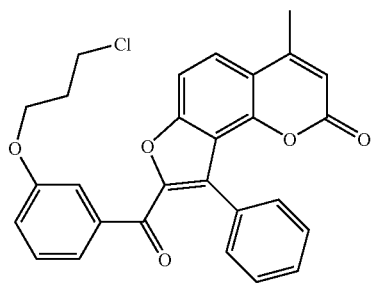
Compound 75
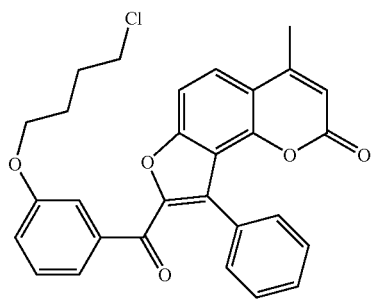
-continued
Compound 76
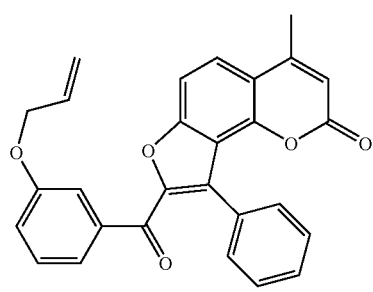
Compound 77
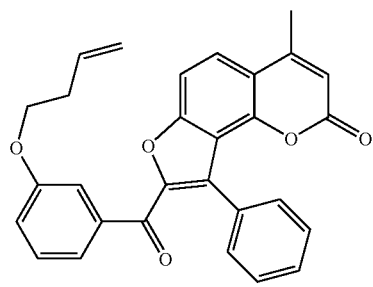
Compound 78
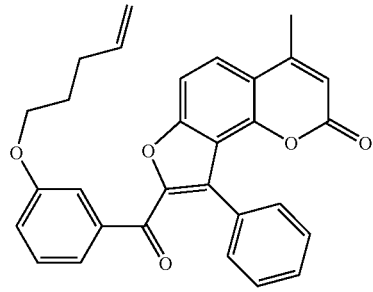
Compound 79
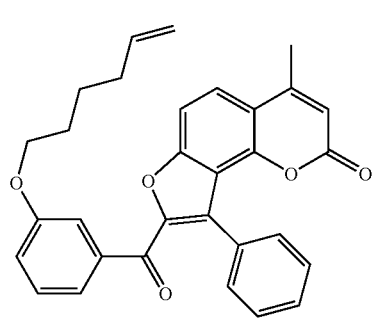
Compound 80
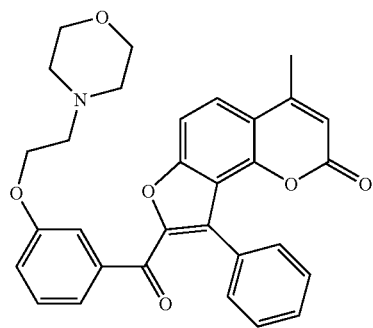

-continued
Compound 81
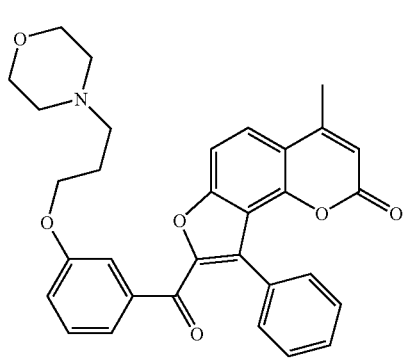
Compound 82
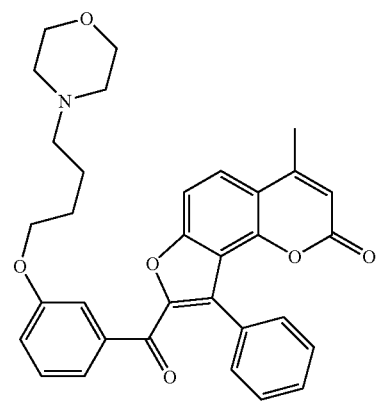
Compound 83
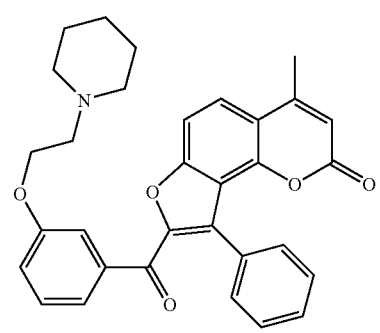
Compound 84
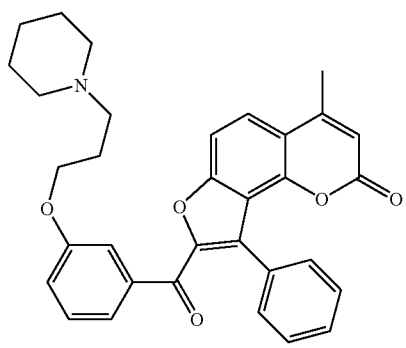
-continued
Compound 85
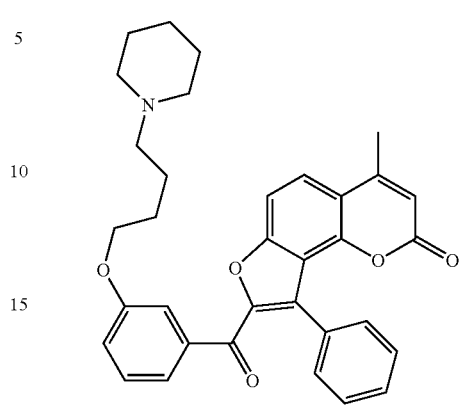
Compound 86
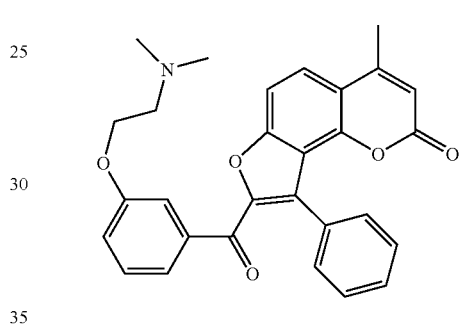
Compound 87
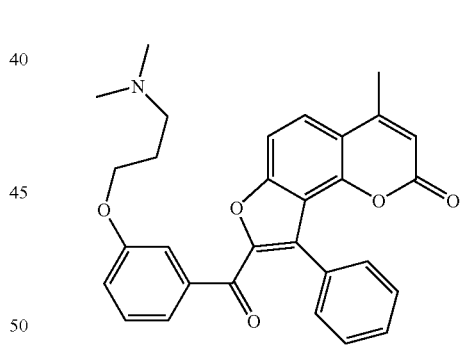
Compound 88
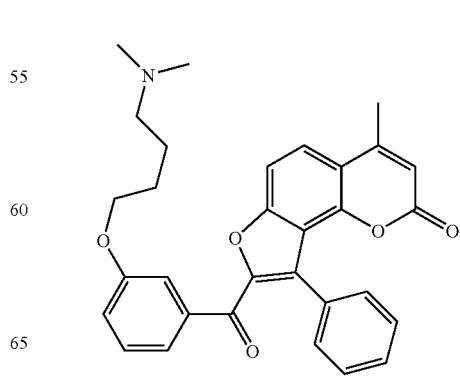

Compound 89
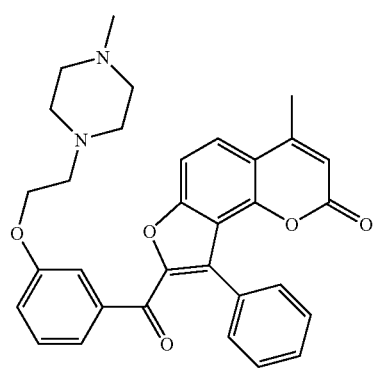
Compound 90
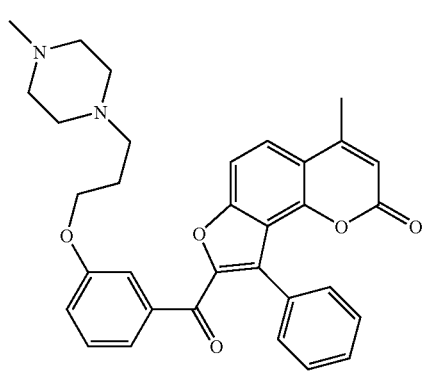
Compound 91
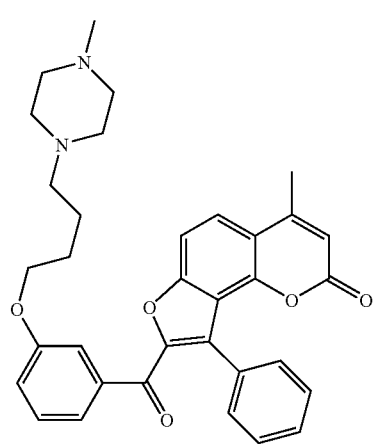
Compound 92
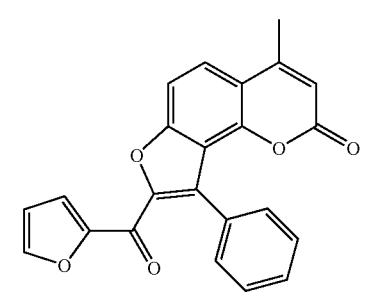
Compound 93
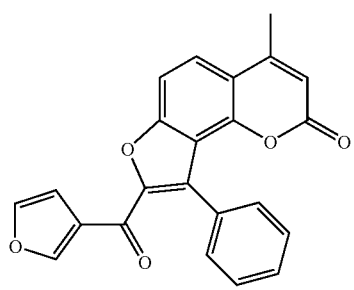
Compound 94
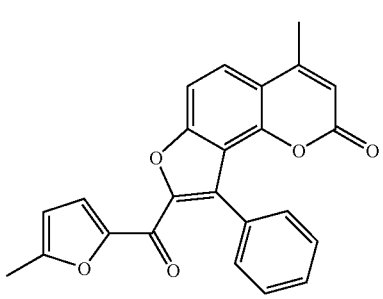
Compound 95
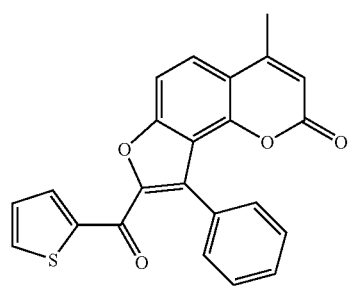
Compound 96
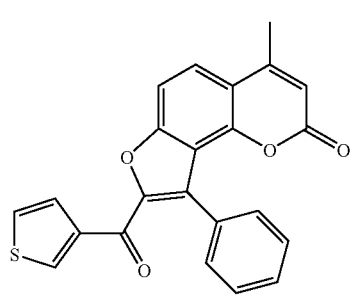
Compound 97
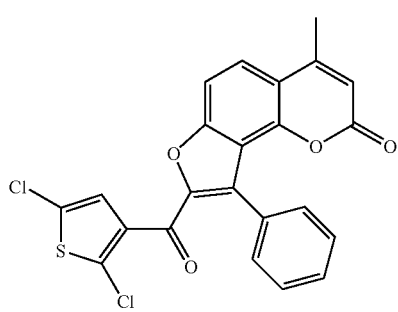

Compound 98
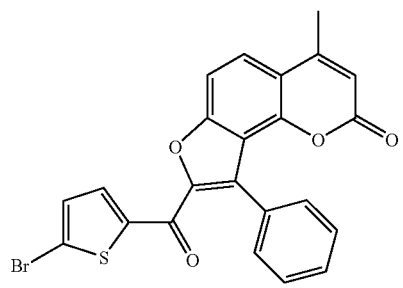
Compound 99
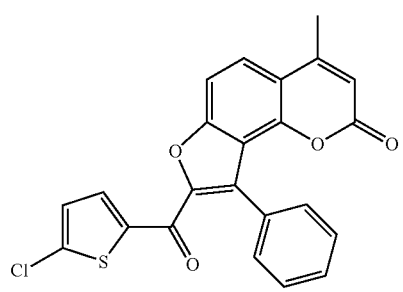
Compound 100
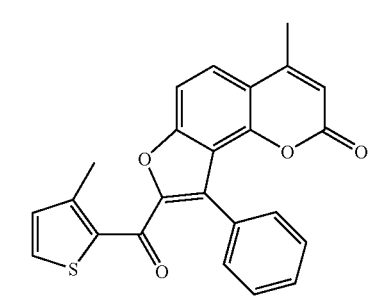
Compound 101
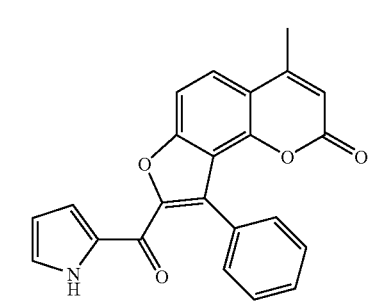
Compound 102
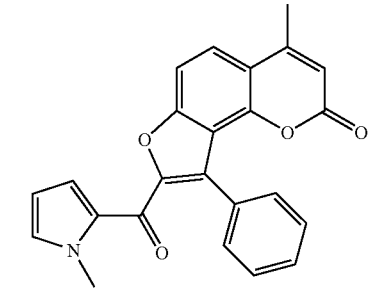
Compound 103
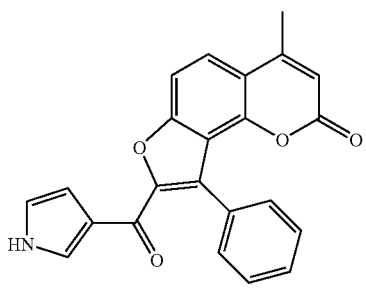
Compound 104
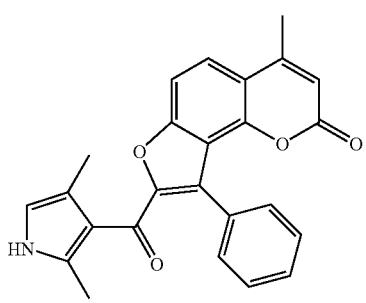
Compound 105
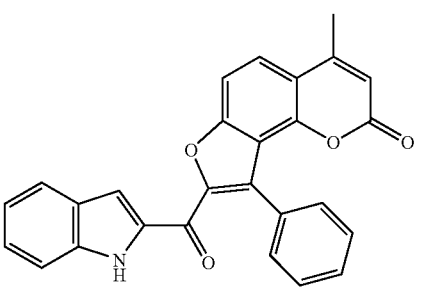
Compound 106
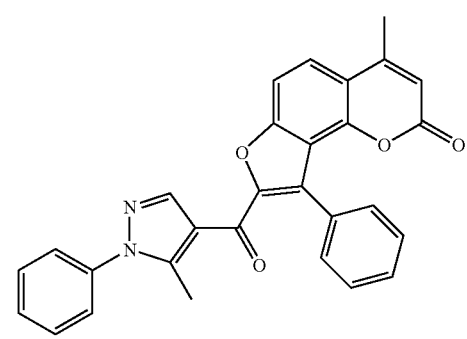
Compound 107
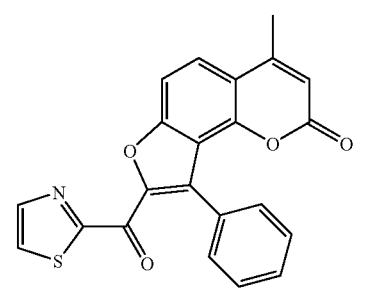

Compound 108
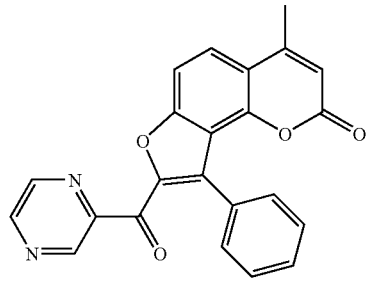
Compound 113
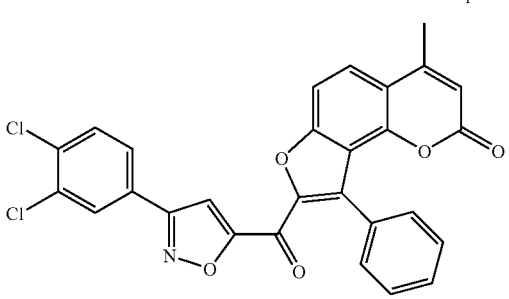
Compound 109
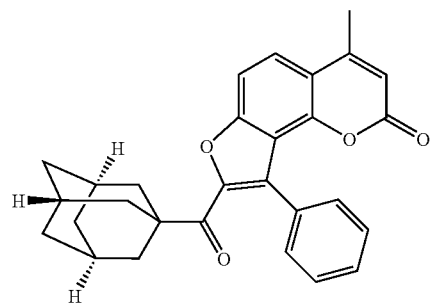
Compound 114
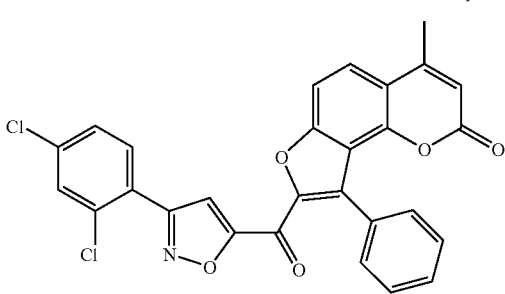
Compound 110
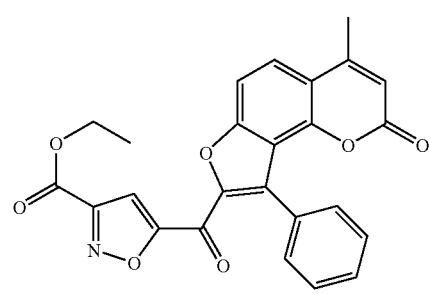
Compound 115
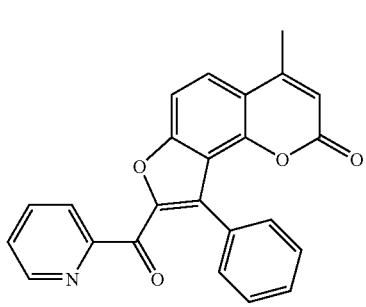
Compound 111
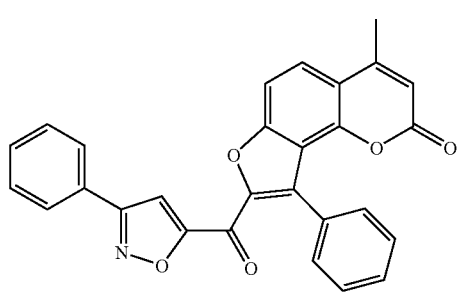
Compound 116
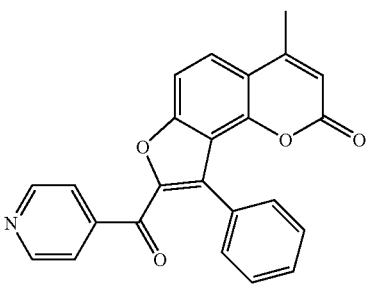
Compound 112
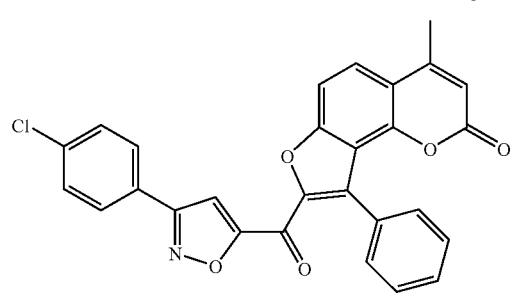
Compound 117
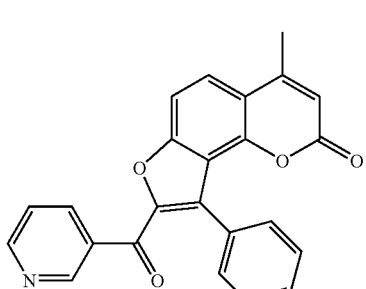

Compound 118
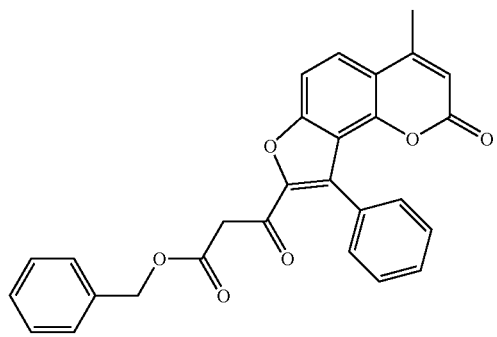
Compound 119
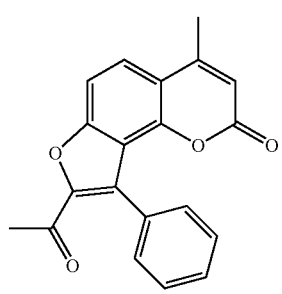
Compound 120
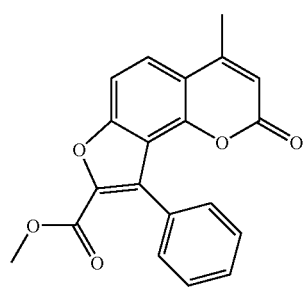
Compound 121
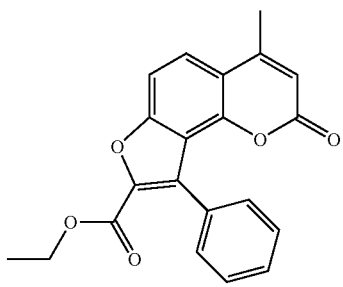
Compound 122
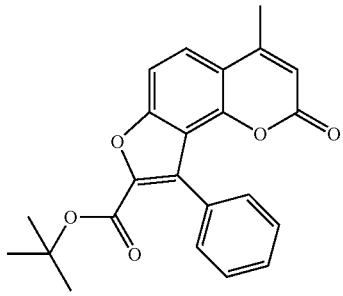
Compound 123
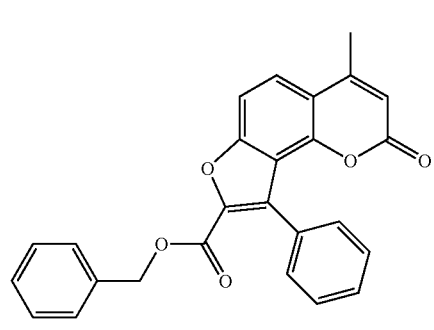
Compound 124
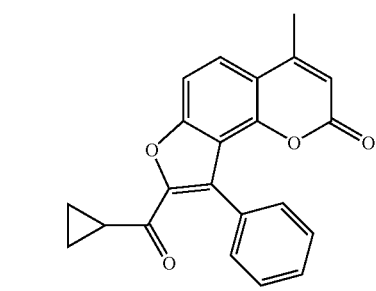
Compound 125
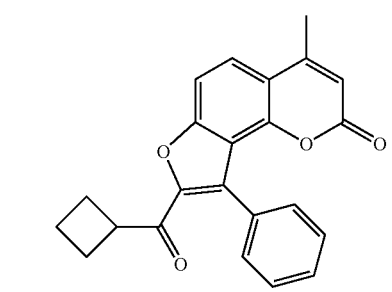
Compound 126
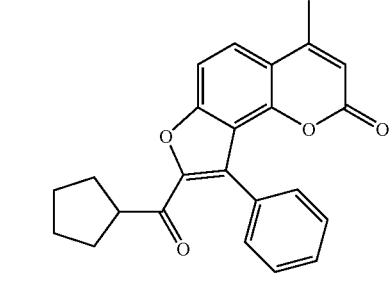
Compound 127
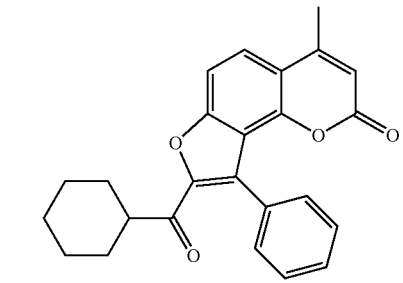

Compound 128
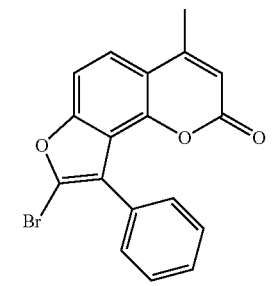
Compound 129
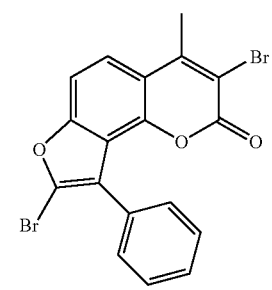
Compound 130
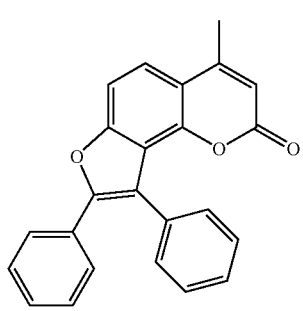
Compound 131
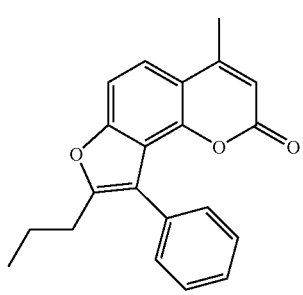
Compound 132
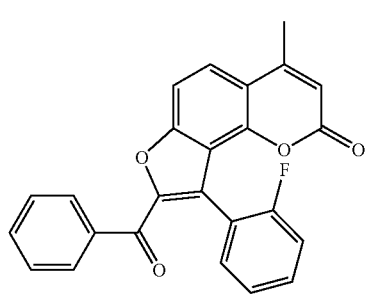
Compound 133
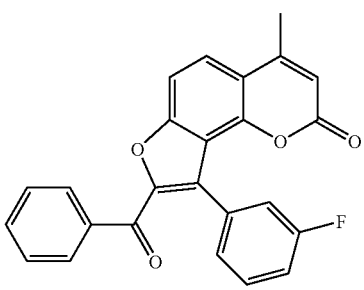
Compound 134
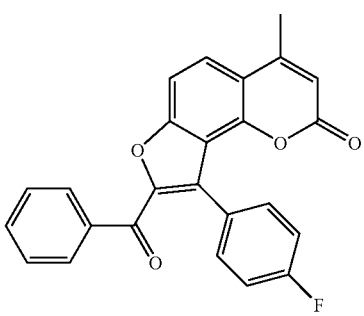
Compound 135
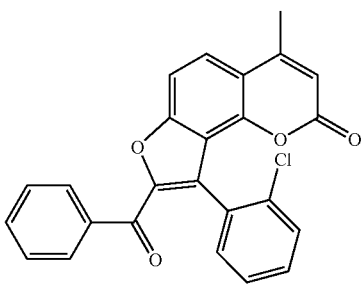
Compound 136
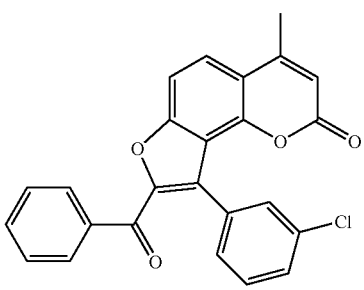
Compound 137
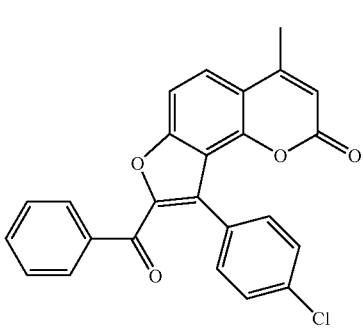

Compound 138
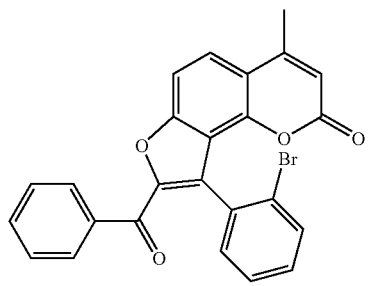
Compound 139
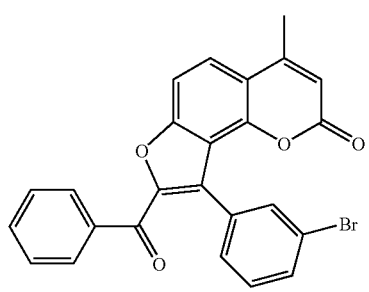
Compound 140
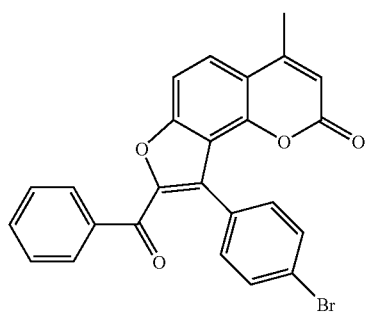
Compound 141
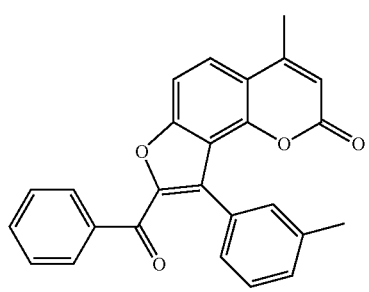
Compound 142
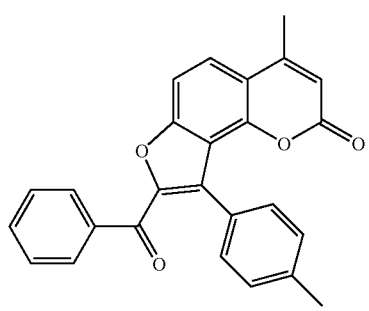
Compound 143
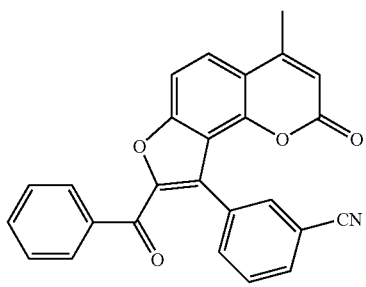
Compound 144
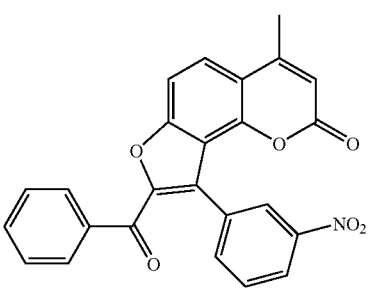
Compound 145
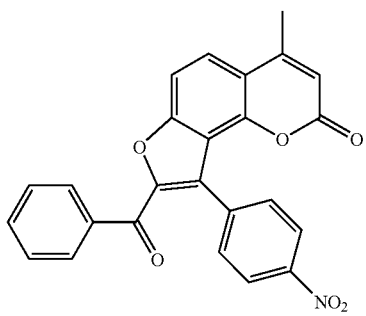
Compound 146
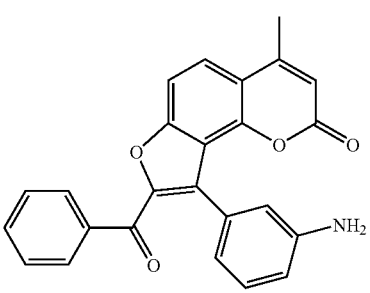
Compound 147
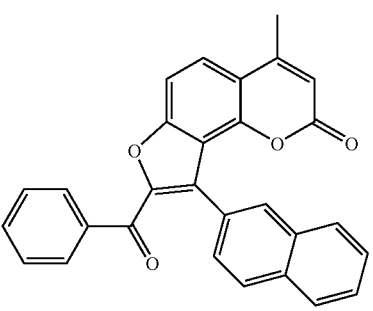

Compound 148
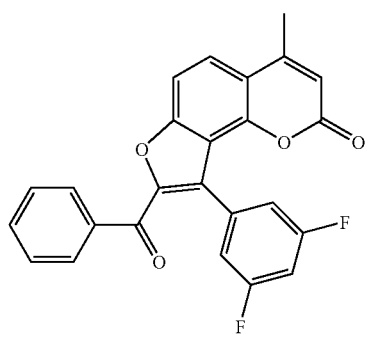
Compound 149
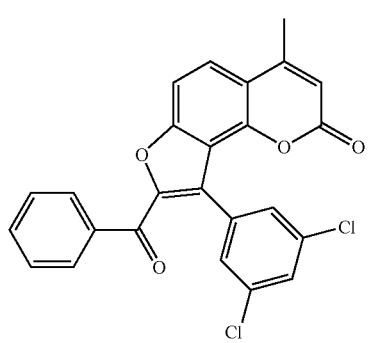
Compound 150
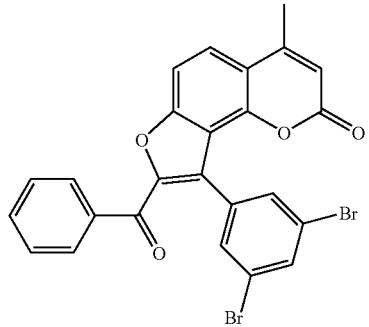
Compound 151
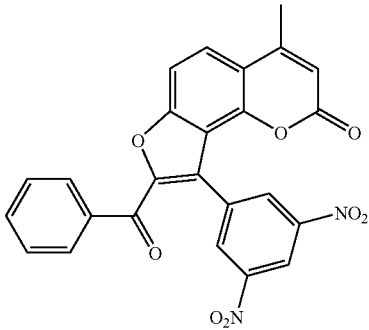
Compound 152
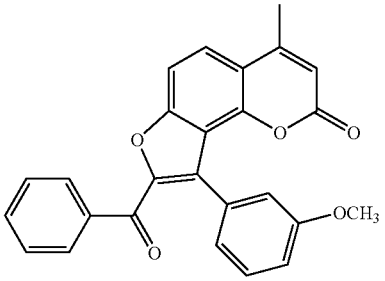
Compound 153
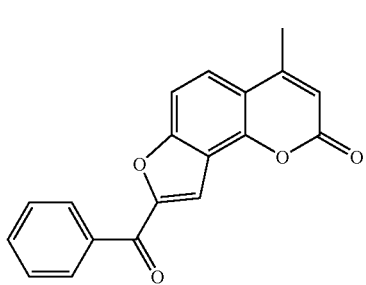
Compound 154
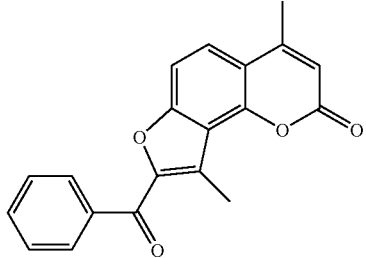
Compound 155
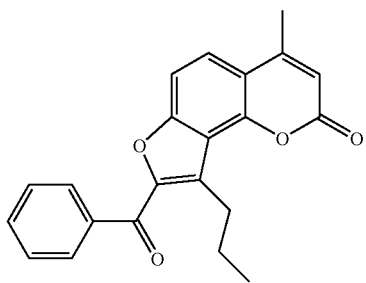
Compound 156
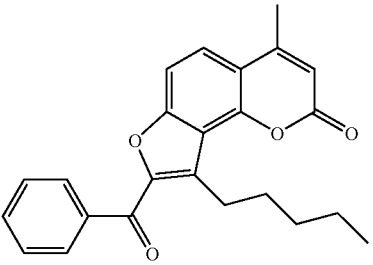
Compound 157
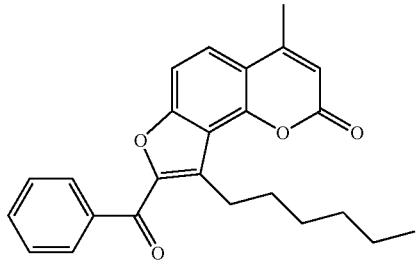

Compound 158
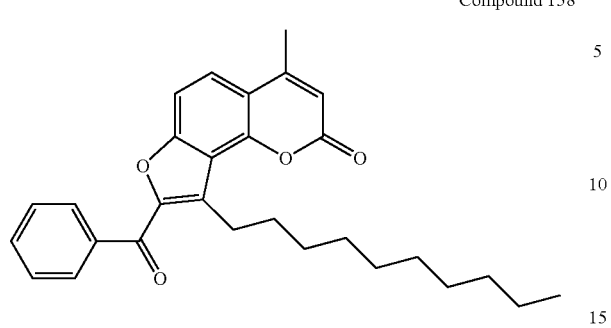
Compound 159
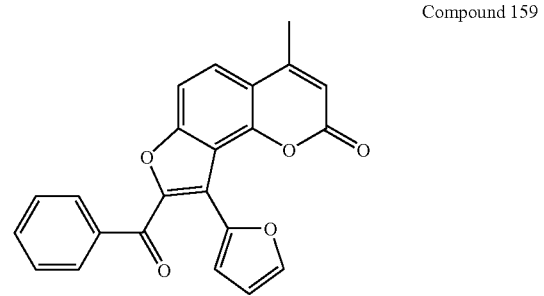
Compound 160
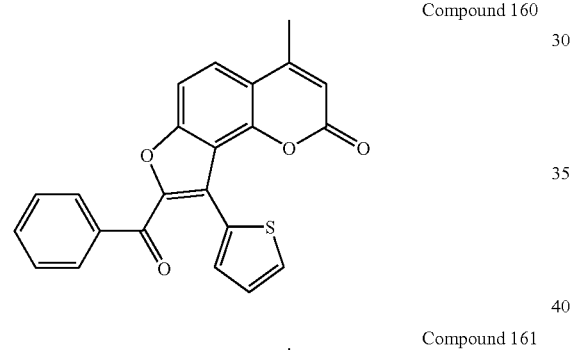
Compound 161
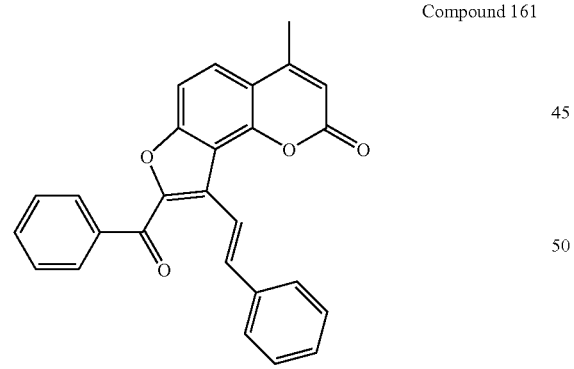
Compound 162
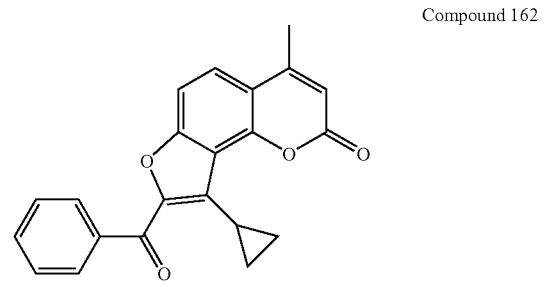
Compound 163
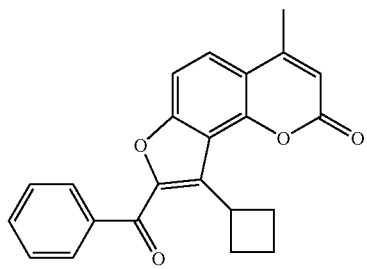
Compound 164
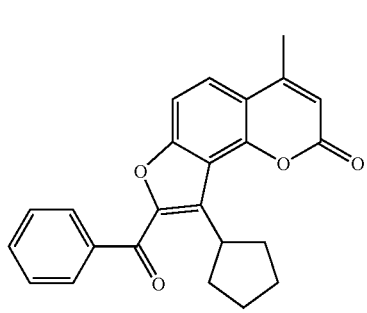
Compound 165
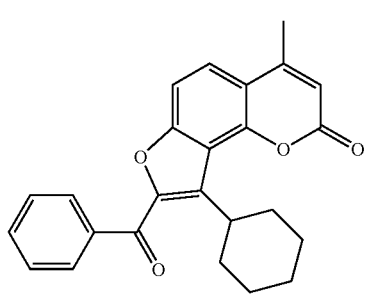
Compound 166
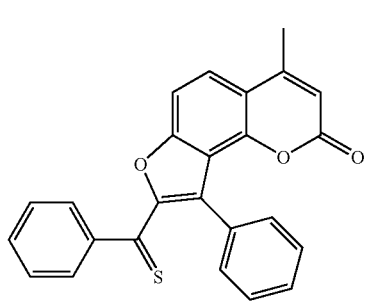
Compound 167
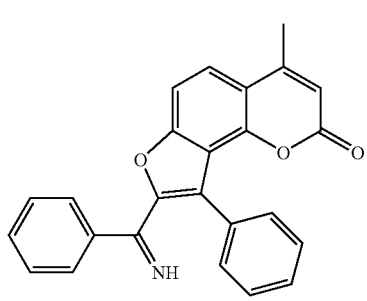

Compound 168
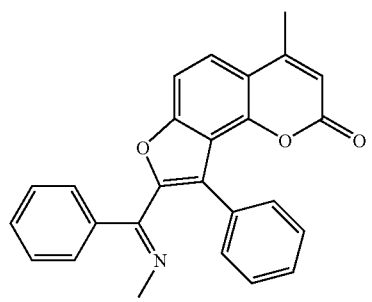
Compound 169
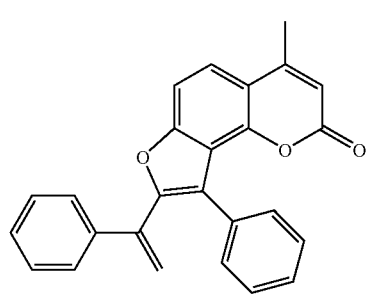
Compound 170
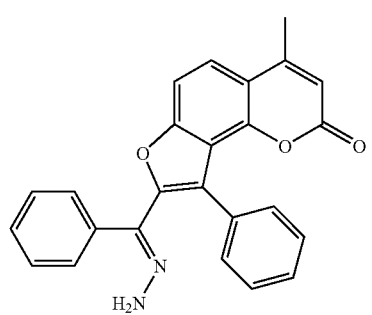
Compound 171
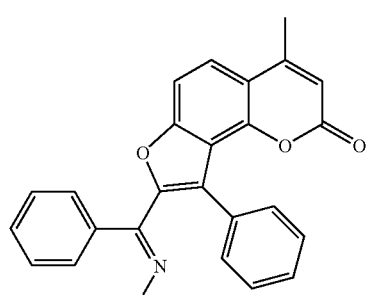
Compound 172
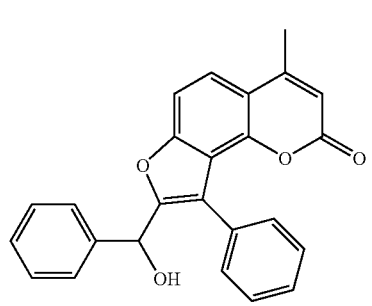
Compound 173
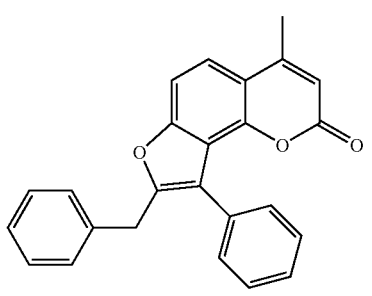
Compound 174
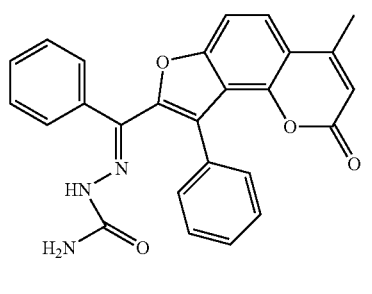
Compound 175
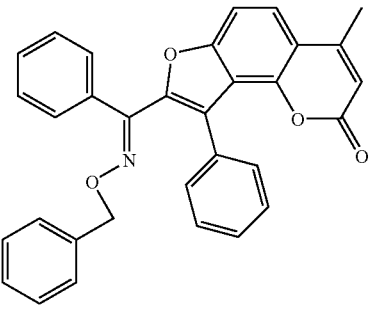
Compound 176
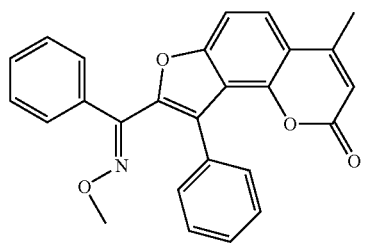
Compound 177
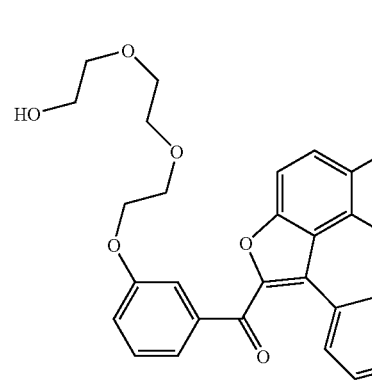

Compound 178
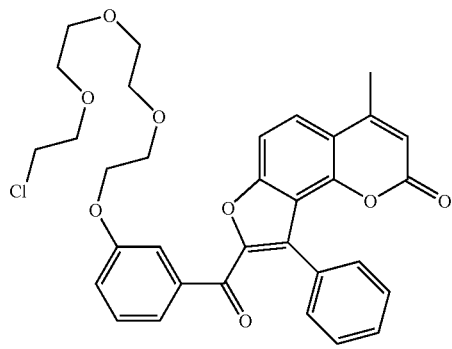
Compound 179
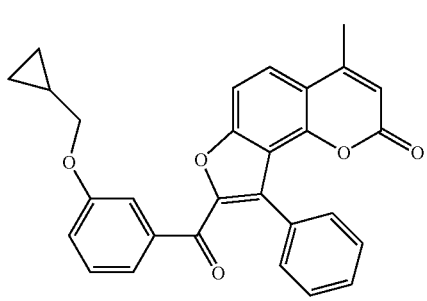
Compound 180
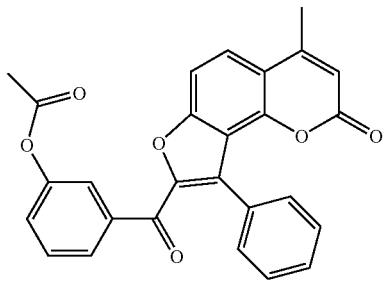
Compound 181
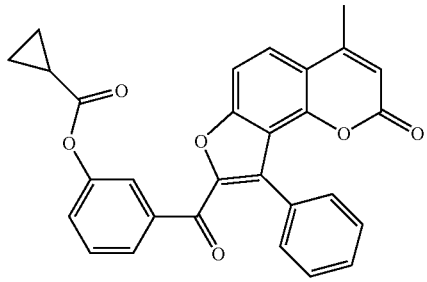
Compound 182
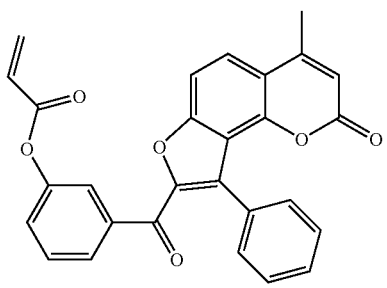
Compound 183
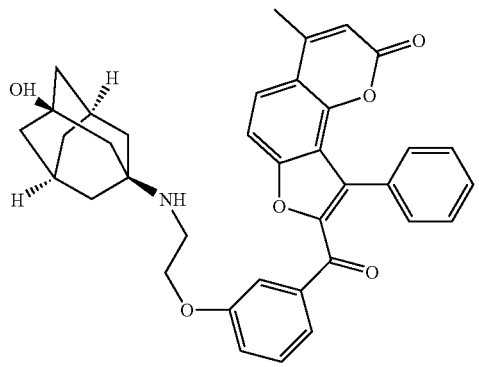
Compound 184
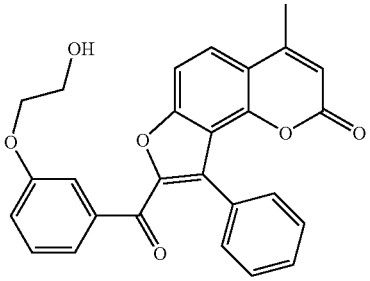
Compound 185
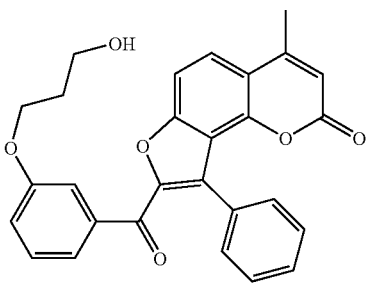
Compound 186
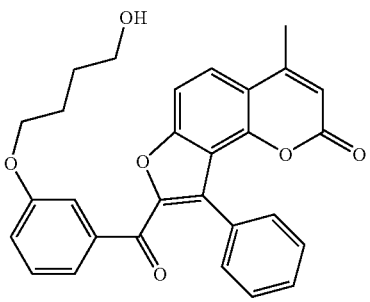
Compound 187
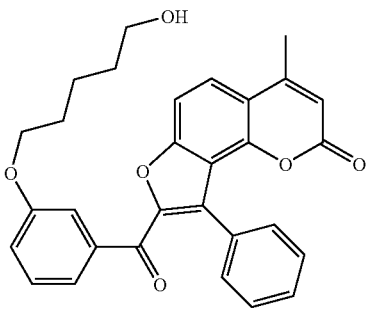

Compound 188
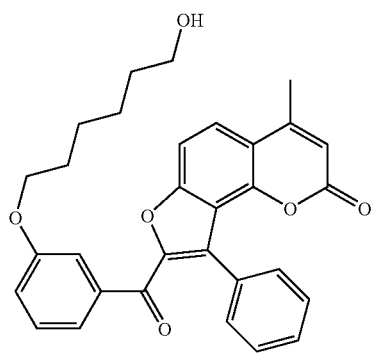
Compound 189
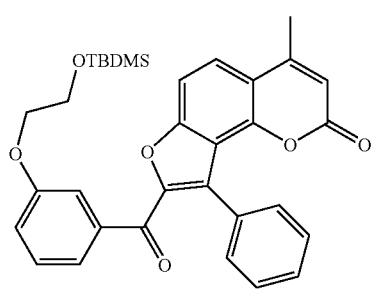
Compound 190
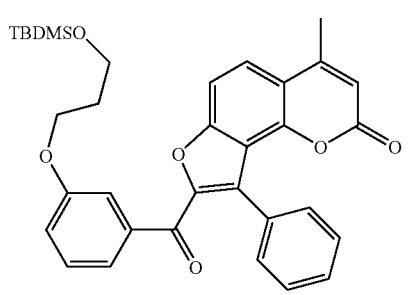
Compound 191
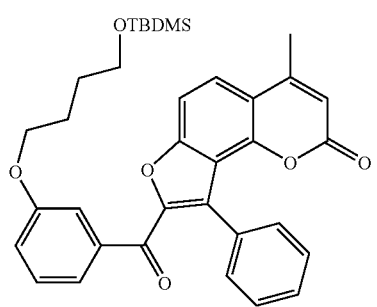
Compound 192
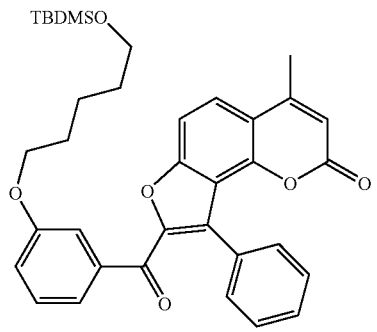
Compound 193
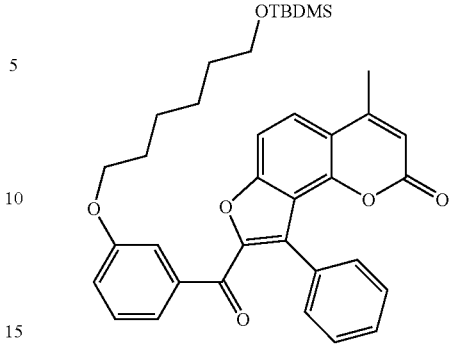
Compound 194
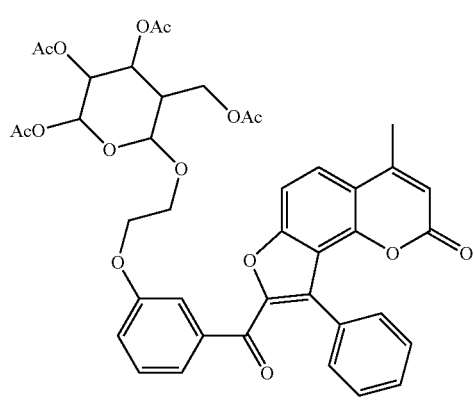
Compound 195
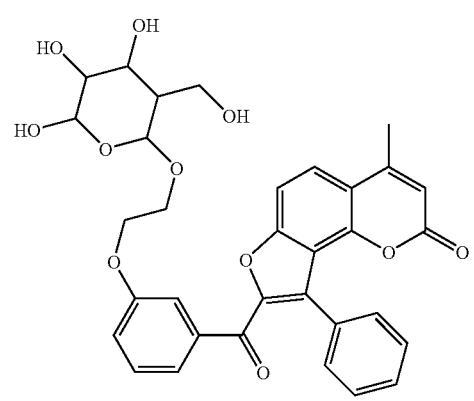
Compound 196
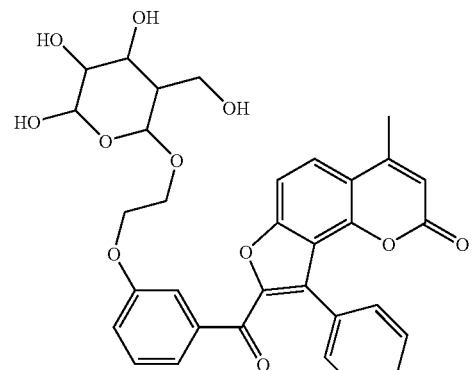

Compound 197
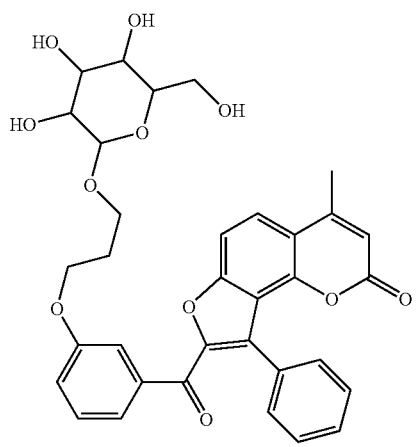
Compound 201
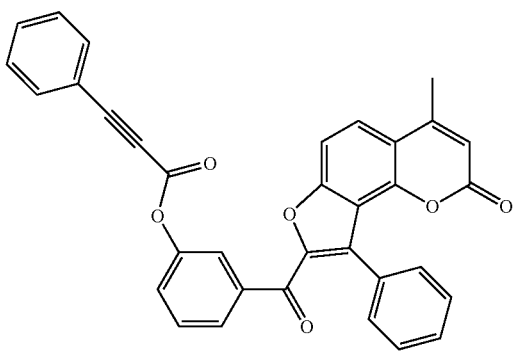
Compound 198
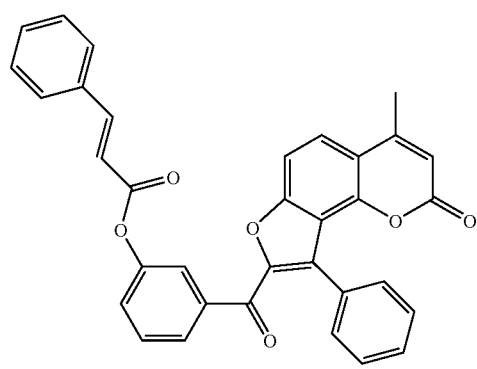
Compound 202
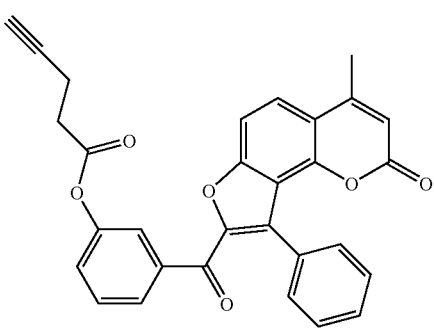
Compound 199
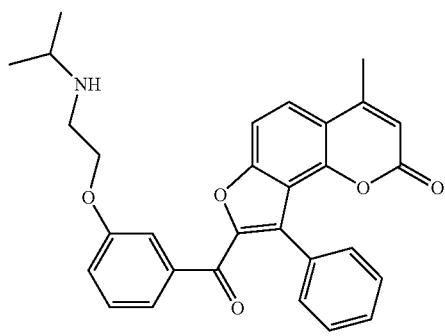
Comopund 203
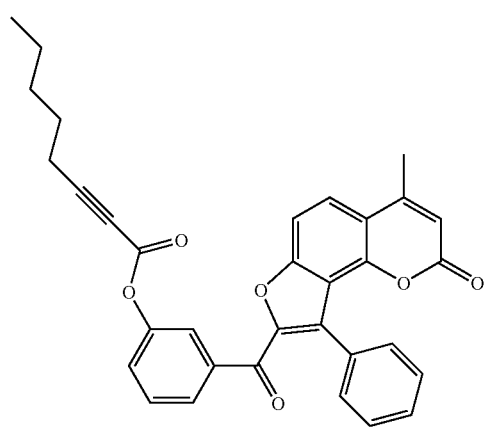
Compound 200
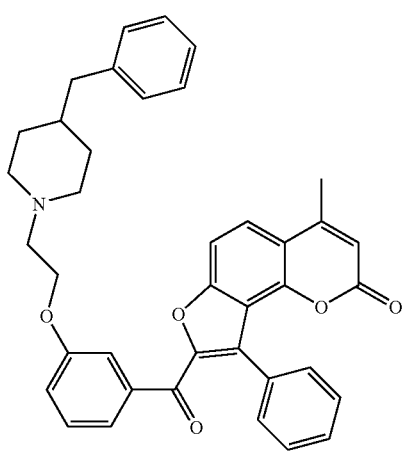
Compound 204
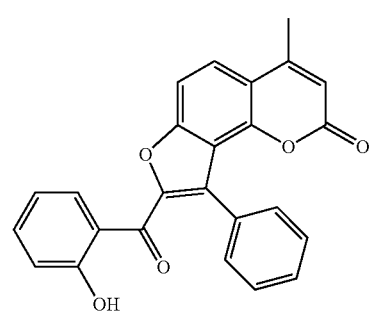

Compound 205
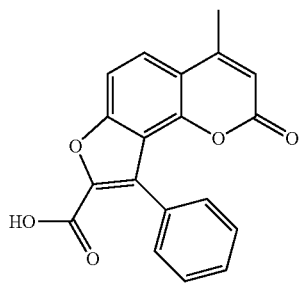
Compound 206
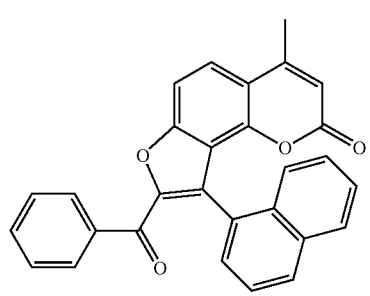
Compound 207
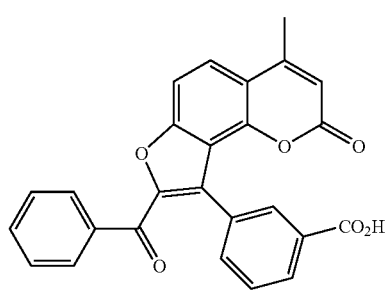
Compound 208
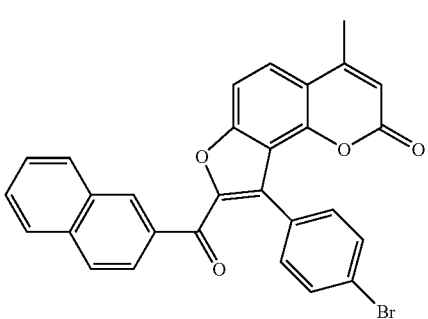
Compound 209
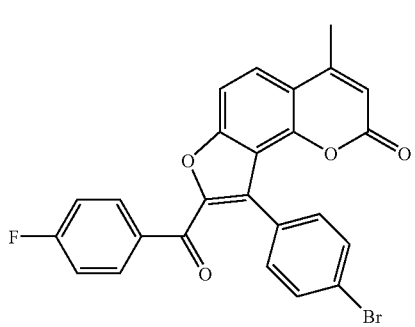
Compound 210
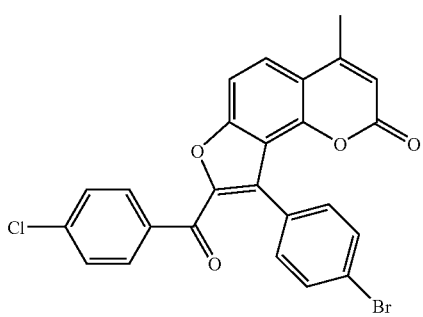
Compound 211
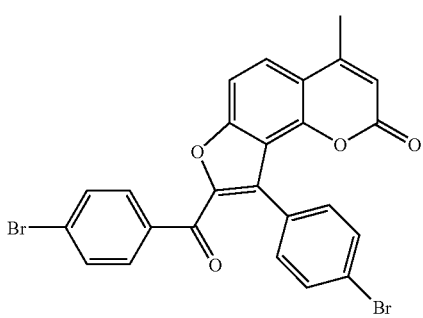
Compound 212
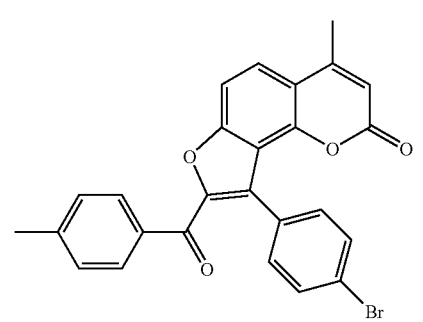
Compound 213
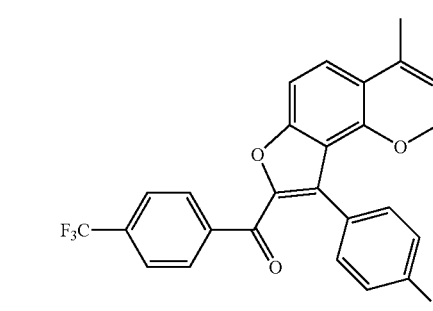
Compound 214
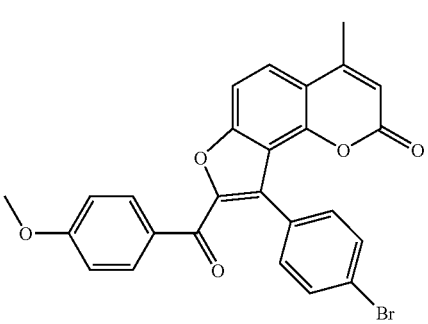

Compound 215
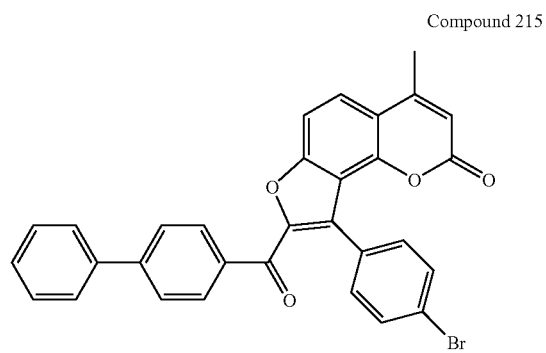
Compound 216
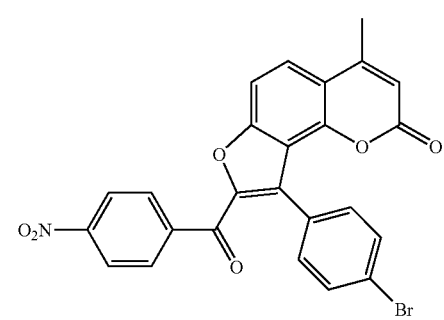
Compound 217
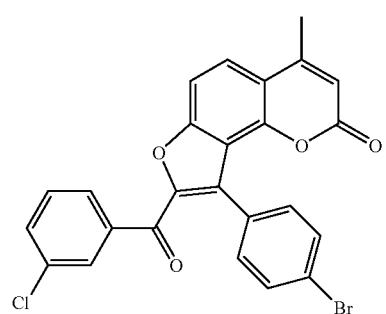
Compound 218
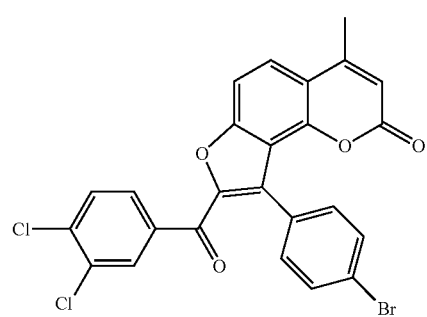
Compound 219
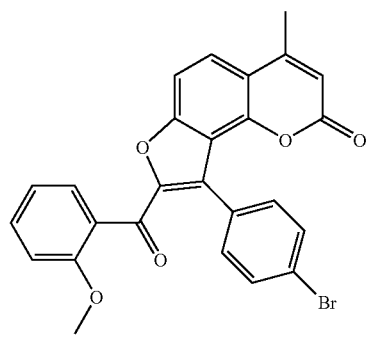
Compound 220
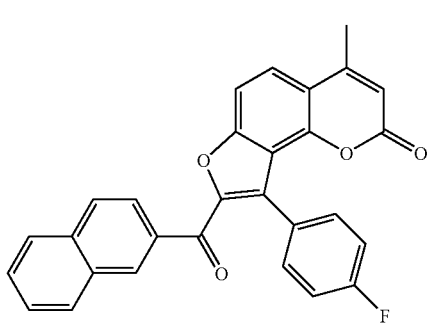
Compound 221
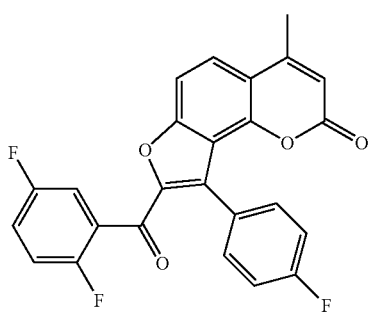
Compound 222
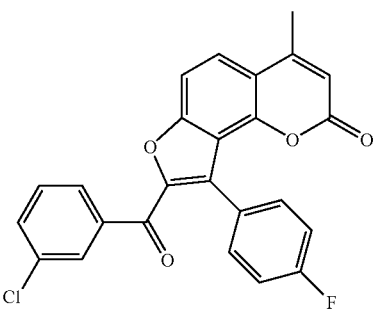
Compound 223
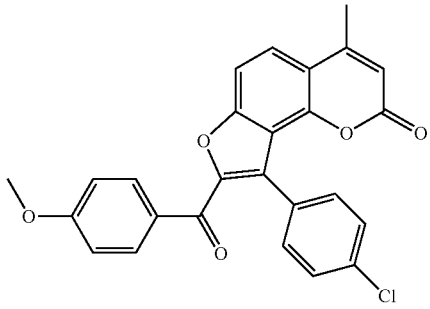

Compound 224
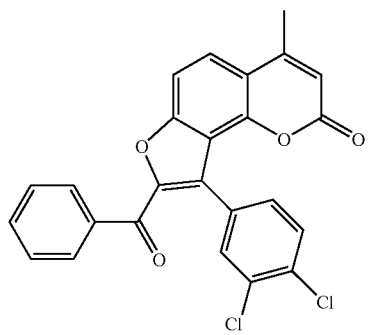
Compound 225
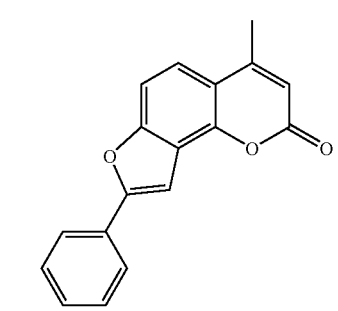
Compound 226
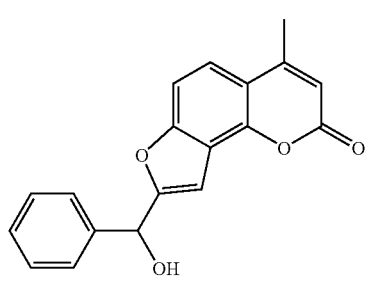
Compound 227
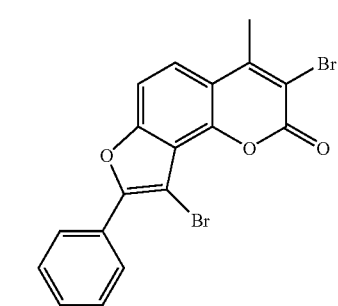
Compound 228
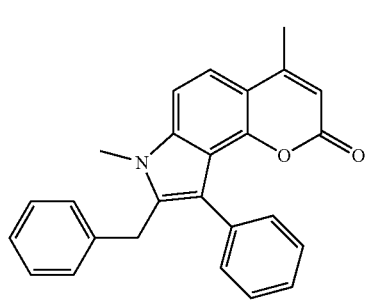
Compound 229
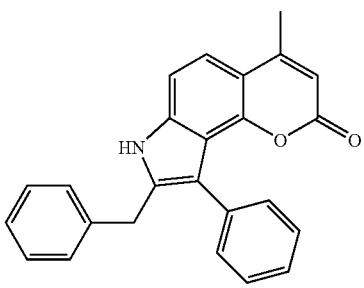
Compound 230
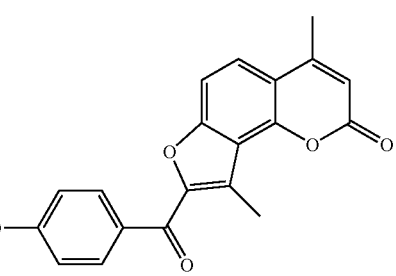
Compound 231
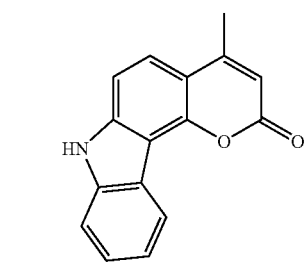
Compound 232
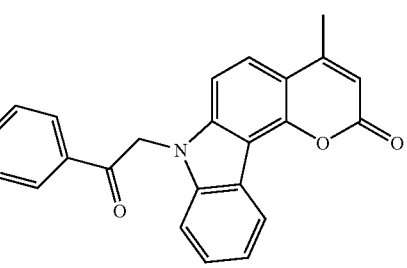
Compound 233
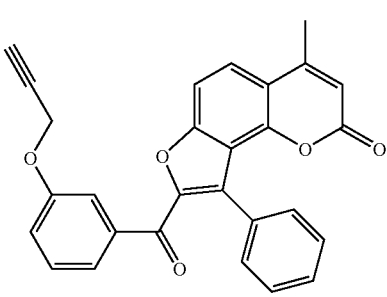

Compound 234
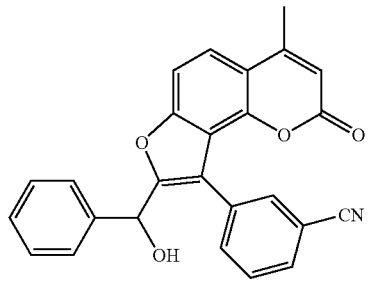
Compound 235
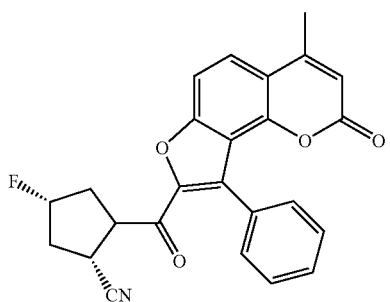
Compound 236
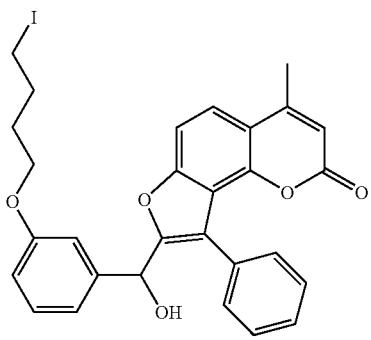
Compound 237
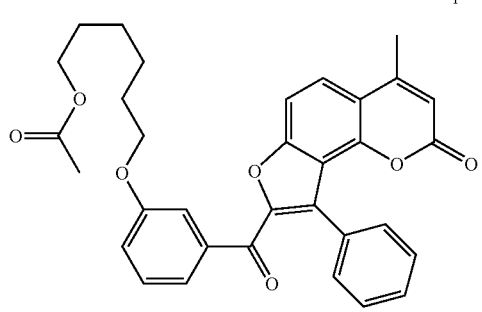
Compound 238
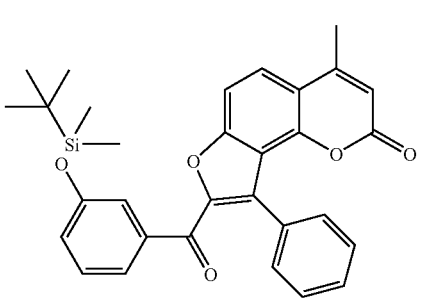
Compound 239
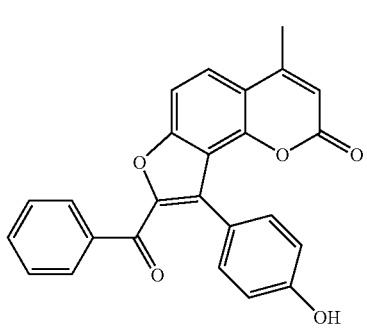
Compound 240
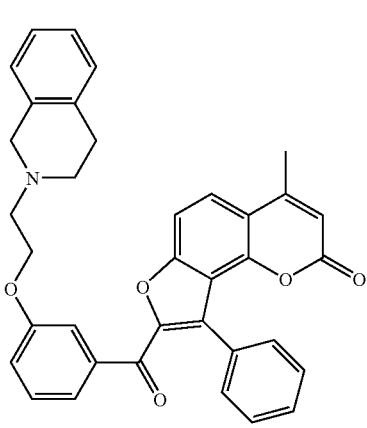
Compound 241
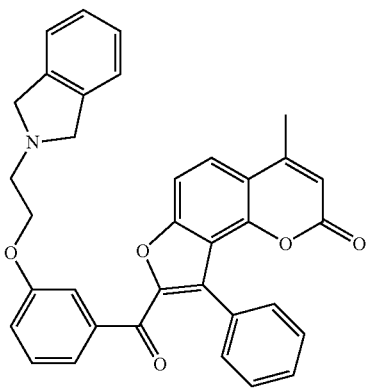
Compound 242
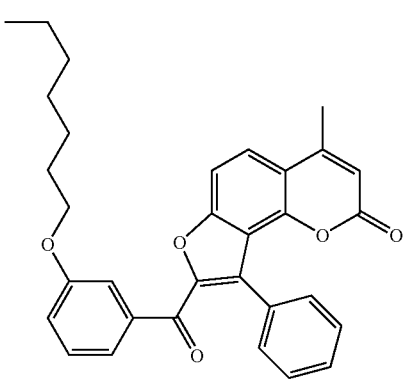

Compound 243
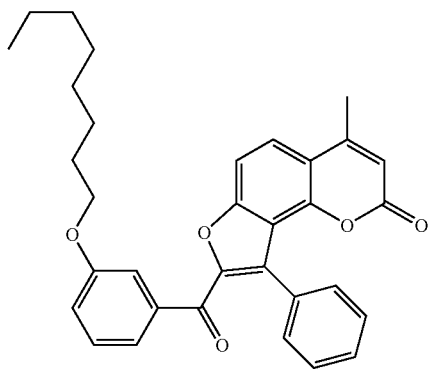
Compound 244
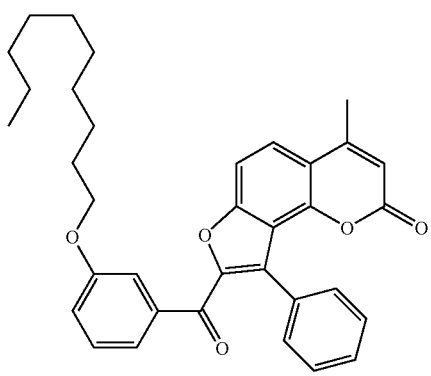
Compound 245
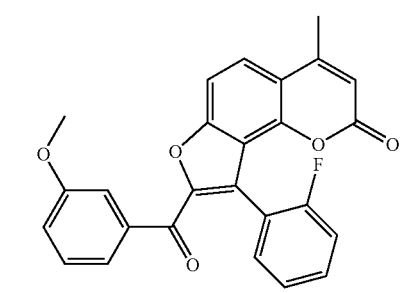
Compound 246
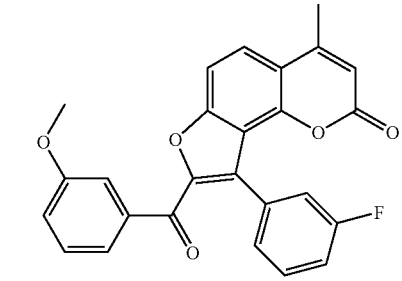
Compound 247
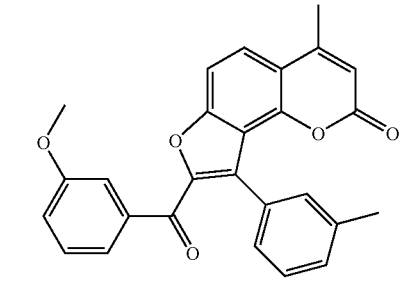
Compound 248
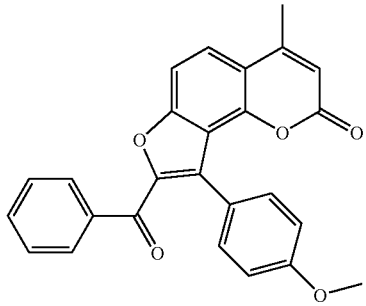
Compound 249
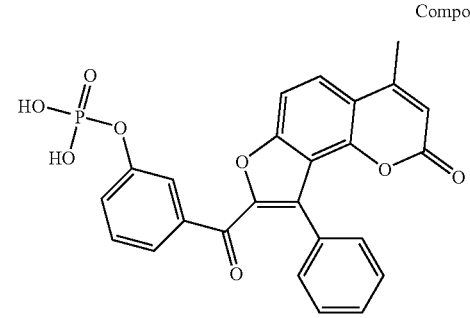
Compound 250
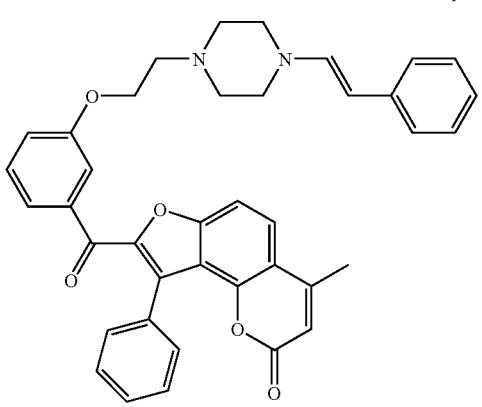
Compound 251
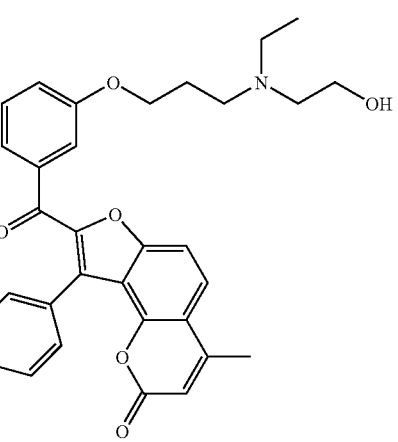

Compound 252
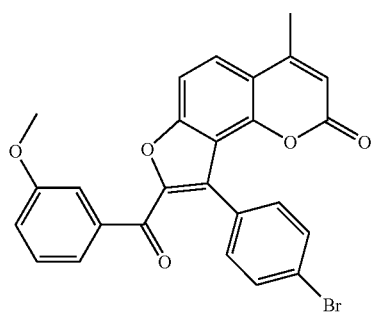
Compound 253
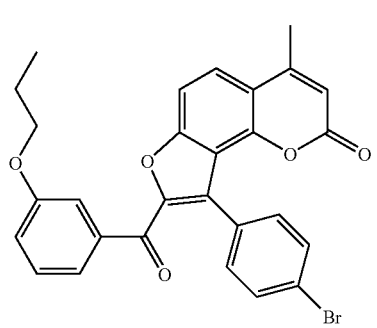
Compound 254
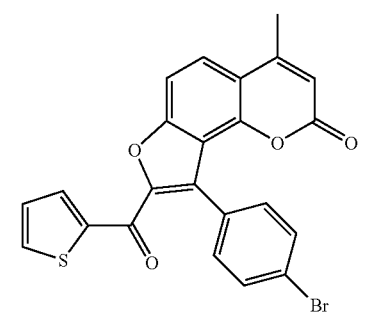
Compound 255
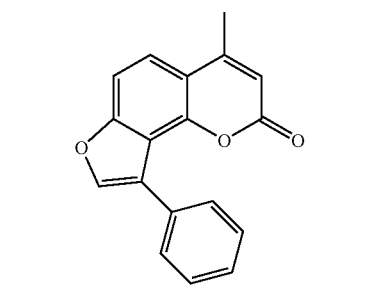
Compound 256
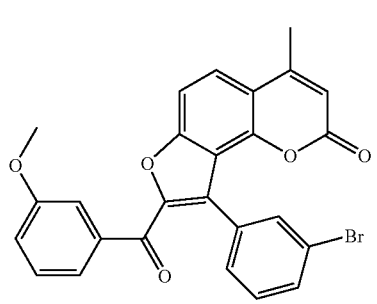
Compound 257
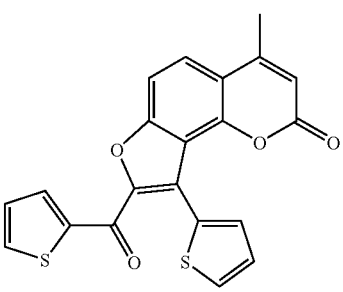
Compound 258
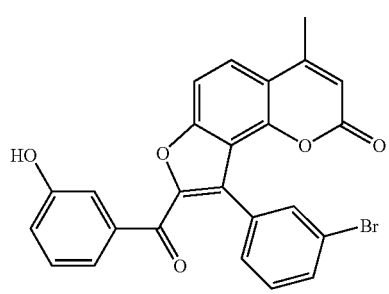
Compound 259
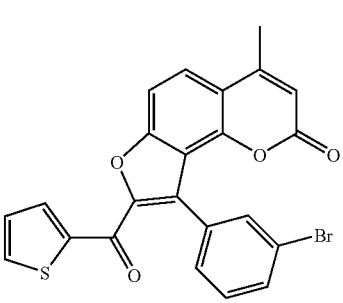
Compound 260
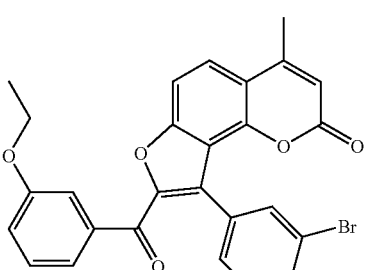
Compound 261

Compound 262

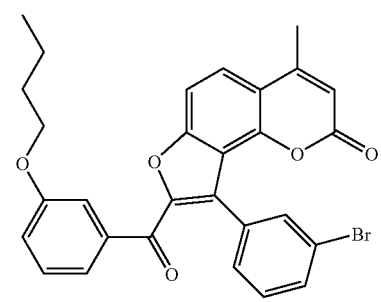

Compound 263

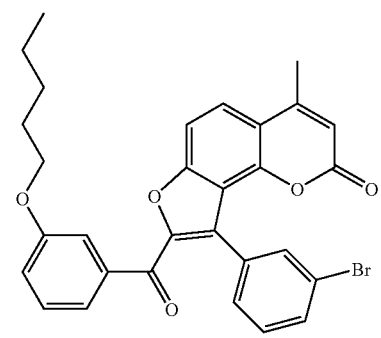

Compound 264

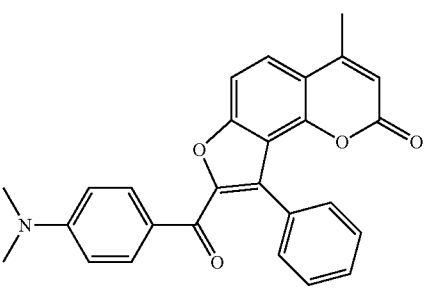

Compound 265

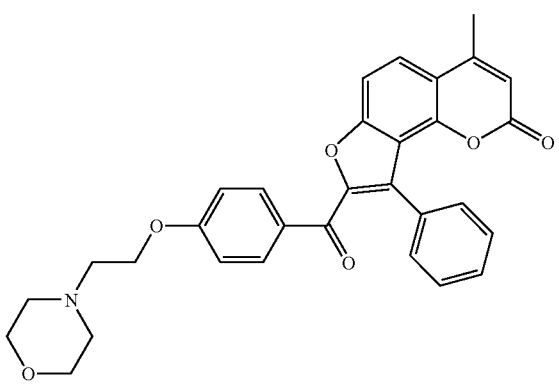

Compound 266

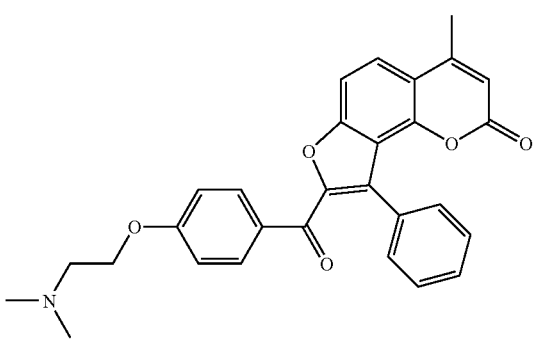

Compound 267

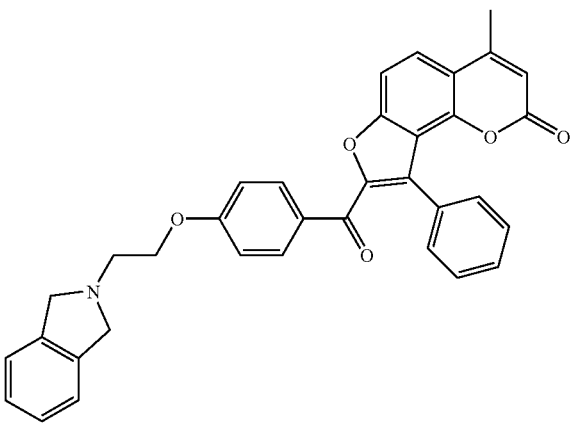

The coumarin compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof The coumarin compounds of this invention can also be synthesized in manners similar to those described, e.g., in Brubaker et al., *J. Med. Chem.*, 1986, 29, 1094-1099, Limaye, *Chem. Ber.*, 1934, 67, 12-14, and Geetanjali et al., *Indian J. Chem. Sect. B*, 1983, 22, 164-165, with necessary modifications as recognized by those skilled in the art.

The route shown in Scheme 1 exemplifies synthesis of the coumarin compounds of the present invention. Triethylamine is added to a solution of 7-hydroxy-4-methyl-chromen-2-one (i) and a benzoyl chloride (ii) in THF at room temperature. The reaction mixture is stirred at room temperature overnight and filtered. The filtrate is concentrated to afford a 7-benzoyloxy-4-methyl-coumarin (iii). A mixture of compound (iii) and finely powdered aluminum chloride is heated at 170° C. for 2 hours to afford an 8-benzoyl-7-hydroxy-4-methyl-chromen-2-one (iv). A mixture of compound (iv), 2-bromoacetophenone (v), and K$_2$CO$_3$ in CH$_3$CN is refluxed overnight. The reaction mixture is filtered and the filtrate is concentrated. The residue is purified by column chromatography to afford a pure 8-benzoyl-4-methyl-9-phenyl-furo[2,3-h]chromen-2-one (vi).

Scheme 1

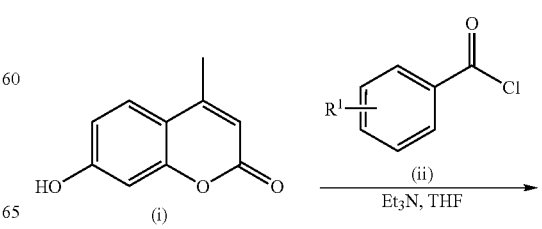

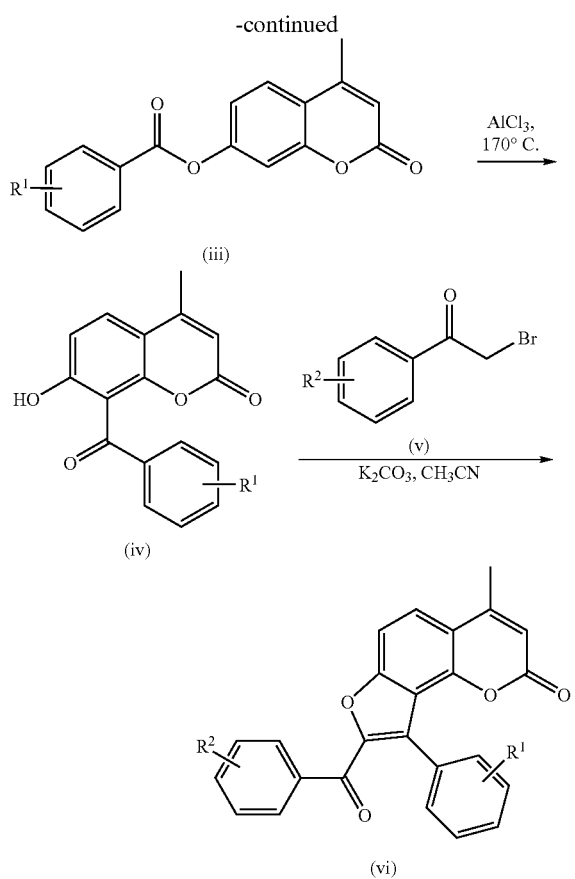

A coumarin compound thus synthesized can be further purified by flash column chromatography, high performance liquid chromatography, crystallization, or any other suitable methods.

The coumarin compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention are (1) a pharmaceutical composition that contains an effective amount of at least one of the coumarin compounds of this invention and a pharmaceutically acceptable carrier, and (2) a method for treating cancer by administering to a subject in need of this treatment an effective amount of such a coumarin compound.

As used herein, the term "treating" refers to administering a coumarin compound to a subject that has cancer, or has a symptom of or a predisposition toward it, with the purpose to prevent, cure, heal, alleviate, relieve, alter, remedy, ameliorate, improve, or affect the disorder, the symptoms of or the predisposition toward the cancer. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

Cancer that can be treated by the methods of the invention includes both solid and haematological tumours of various organs. Examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

The compounds described herein can be administered in conjunction with another therapeutic agent such as a cytotoxic agent, or be applied in combination with another therapy such as radiotherapy and immunotherapy. Non-limiting examples of cytotoxic agents suitable for use in combination with the coumarin compounds of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs, including, e.g., CC-5013 and CC-4047; protein kinase inhibitors, including, e.g., imatinib mesylate, gefitinib, dasatinib, erlotinib, lapatinib, sunitinib, nilotinib, and sorafenib; antibodies, including, e.g., trastuzumab, rituximab, cetuximab, and bevacizumab; mitoxantrone; dexamethasone; prednisone; and temozolomide.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A coumarin compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the active coumarin compounds can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the coumarin compounds of this invention in anticancer activities such as inhibiting growth of tumor cells. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of 8-benzoyl-4-methyl-9-phenyl-furo[2,3-h]chromen-2-one (Compound 1)

7-benzoyloxy-4-methyl-coumarin: To a solution of 7-hydroxy-4-methyl-chromen-2-one (0.5210 g, 3.0 mmol) and benzoyl chloride (0.4844 g, 0.4 mL, d=1.211 g/mL, 3.4 mmol) in THF (40 mL) was added Et$_3$N (1 mL) at room temperature. The reaction mixture was stirred at room temperature overnight and filtered. The filtrate was concentrated to give the crude product 7-benzoyloxy-4-methyl-coumarin.
$^1$H NMR δ 8.230-7.210 (m, 8H), 6.297 (d, J=0.9 Hz, 1H), 2.466 (d, J=0.9 Hz, 3H).

8-benzoyloxy-7-hydroxy-4-methyl-chromen-2-one: A mixture of 7-benzoyloxy-4-methyl-coumarin (0.28 g, 1 mmol) and finely powdered aluminum chloride (0.40 g, 3 mmol) was heated at 170° C. for 2 hours. After the mixture was cooled to room temperature, ice and dilute hydrochloric acid were added. The mixture was extracted with ethyl acetate. The ethyl acetate solution was washed successively with dilute acid, water, and sat. NaHCO$_3$ (aq). The organic layer was concentrated to provide 8-benzoyloxy-7-hydroxy-4-methyl-chromen-2-one (0.21 g) as a grayish material.
$^1$H NMR (300 MHz, CDCl$_3$): δ 10.85 (br, OH), 7.717-7.657 (m, 3H), 7.637~7.573 (m, 1H), 7.501-7.429 (m, 2H), 7.021 (d, J=9 Hz, 1H), 6.072 (s, 1H), 2.415 (d, J=0.6 Hz, 3H)

8-benzoyl-4-methyl-9-phenyl-furo[2,3-h]chromen-2-one: A mixture of 8-benzoyl-7-hydroxy-4-methyl-chromen-2-one (30 mg, 0.1 mmol), 2-bromoacetophenone (22 mg, 0.11 mmol), and K$_2$CO$_3$ (143 mg, 1.03 mmol) in CH$_3$CN (5 mL) was refluxed overnight. The reaction mixture was filtered and the filtrate was concentrated. The residue was purified by silica gel column chromatography (hexane/ethyl acetate=3/1 then hexane/ethyl acetate=1/1, R$_f$=0.33 hexane/ethyl acetate=1/1) to provide 8-benzoyl-4-methyl-9-phenyl-furo [2,3-h]chromen-2-one as a yellow solid (71% yield).
$^1$H NMR δ 7.783-7.323 (m, 12H), 6.240 (d, J=0.9 Hz, 1H), 2.487 (d, J=1.2 Hz, 3H). $^{13}$C NMR δ 185.454, 159.440, 156.417, 152.814, 149.928, 148.096, 136.540, 132.845, 130.616, 129.624, 128.708, 128.647, 128.036, 127.716, 124.189, 116.311, 115.304, 113.487, 108.907, 19.491.

Example 2

Syntheses of Compounds 2-4, 6, 8-12, 14, 16-22, 26, 30-92, 94-98, 100-102, 105-107, 109-122, 127-151, 153-161, 165, 166, 170-191, and 193-267

Compounds 2-4, 6, 8-12, 16-22, 26, 30-92, 94-98, 100-102, 105-107, 109-122, 127-151, 153-161, 165, 166, 170-191, and 193-267 were prepared in a manner similar to that described in Example 1. $^1$H NMR, $^{13}$C NMR, IR, or MS data of these compounds are listed in Table 1 below:

TABLE 1

| Cpd# | Analytical Data |
|---|---|
| 2 | $^1$H NMR (400 MHz, CDCl$_3$): δ 7.78-7.74 (m, 3H), 7.58-7.41 (m, 5H), 7.32-7.26 (m, 5H), 6.35 (d, J = 9.6 Hz, 1H). $^{13}$C NMR (125 MHz, CDCl$_3$): δ 185.4, 159.4, 156.6, 150.5, 148.2, 144.0, 136.6, 132.9, 130.6, 129.7, 129.5, 128.8, 128.4, 128.1, 127.8, 127.5, 116.4, 114.9, 114.3, 109.4. HRMS (M$^+$): Calcd. for C$_{24}$H$_{14}$O$_4$ 366.0892, found 366.0876. |

TABLE 1-continued

| Cpd# | Analytical Data |
|---|---|
| 3 | $^1$H NMR (600 MHz, CDCl$_3$): δ 7.76-7.75 (m, 2H), 7.57 (d, J = 1.1 Hz, 1H), 7.51-7.41 (m, 5H), 7.31-7.26 (m, 5H), 2.15 (s, 3H). $^{13}$C NMR (150 MHz, CDCl$_3$): δ 185.5, 160.9, 155.8, 149.1, 147.9, 139.7, 136.6, 132.8, 130.6, 129.6, 128.7, 128.4, 128.0, 127.7, 126.8, 124.1, 116.1, 114.9, 109.1, 17.7. HRMS (M$^+$): Calcd. for C$_{25}$H$_{16}$O$_4$ 380.1049, found 380.1039. |
| 4 | $^1$H NMR (400 MHz, CDCl$_3$): δ 7.97 (d, J = 10.0 Hz, 1H), 7.77-7.75 (m, 2H), 7.74-7.38 (m, 4H), 7.32-7.26 (m, 5H), 6.38 (d, J = 10.0 Hz, 1H), 2.66 (s, 3H). |
| 6 | $^1$H NMR (600 MHz, CDCl$_3$): δ 7.76-7.72 (m, 1H), 7.73 (d, J = 9.0 Hz, 1H), 7.54 (d, J = 9.0 Hz, 1H), 7.46-7.41 (m, 2H), 7.30-7.26 (m, 5H), 2.46 (s, 3H), 2.17 (s, 3H). $^{13}$C NMR (150 MHz, CDCl$_3$): δ 185.6, 160.7, 155.7, 148.1, 148.0, 146.3, 136.7, 132.8, 130.7, 129.8, 129.7, 128.8, 128.7, 128.0, 127.7, 124.2, 120.8, 115.9, 108.7, 15.9, 13.4. HRMS (M$^+$): Calcd. for C$_{26}$H$_{18}$O$_4$ 394.1205, found 394.1194. |
| 8 | $^1$H NMR (300 MHz, CDCl$_3$): δ 8.02-7.96 (m, 1H), 7.81-7.78 (m, 2H), 7.54-7.42 (m, 4H), 7.34-7.26 (m, 4H), 6.09 (s, 1H), 2.63 (s, 3H), 2.47 (s, 3H). |
| 9 | $^1$H NMR (600 MHz, CDCl$_3$): δ 7.76-7.73 (m, 2H), 7.54 (d, J = 8.9 Hz, 1H), 7.45-7.42 (m, 3H), 7.30-7.27 (m, 5H), 6.23 (q, J = 2.0 Hz, 1H), 2.85 (qd, J = 7.4, 2.0 Hz, 2H), 1.33 (t, J = 7.4 Hz, 3H). $^{13}$C NMR (150 MHz, CDCl$_3$): δ 185.6, 159.8, 157.8, 156.3, 150.1, 148.1, 136.6, 132.8, 130.6, 129.6, 128.7, 128.0, 127.7, 123.8, 116.5, 114.6, 111.5, 108.9, 25.4, 12.2. HRMS (M$^+$): Calcd. for C$_{26}$H$_{18}$O$_4$ 394.1205, found 394.1205. |
| 10 | $^1$H NMR (600 MHz, CDCl$_3$): δ 10.09 (s, 1H), 8.77 (d, J = 9.1 Hz, 1H), 7.77 (d, J = 7.2 Hz, 1H), 7.63 (d, J = 9.1 Hz, 1H), 7.46-7.44 (m, 4H), 7.33-7.27 (m, 5H), 6.83 (s, 1H). $^{13}$C NMR (150 MHz, CDCl$_3$): δ 191.5 (CH), 185.3 (CH), 159.0 (C), 156.8 (C), 144.1 (C), 136.4 (C), 133.1 (CH), 130.5 (CH), 129.7 (CH × 2, C), 129.4 (C), 128.9 (CH), 128.2 (C), 128.1 (CH × 2), 127.9 (CH × 2), 125.5 (CH), 124.2 (C), 116.4 (C), 113.6 (C), 110.1 (CH), 109.0 (C). EIMS m/z (relative intensity): 394 (M$^+$, 27), 380 (26), 379 (36), 235 (45), 221 (49), 133 (73), 119 (82), 105 (100), 97 (56), 85 (74). HRMS Calcd. for C$_{25}$H$_{14}$O$_4$ 394.3757, found 394.0847. IR (neat): 2920, 2851, 1734, 1709, 1653, 1600, 1446, 1356, 1239, 1078 cm$^{-1}$. |
| 11 | $^1$H NMR (600 MHz, CDCl$_3$): δ 8.03-8.00 (m, 1H), 7.77-7.75 (m, 1H), 7.62 (d, J = 9.1 Hz, 1H), 7.45-7.43 (m, 3H), 7.32-7.28 (m, 5H), 6.86 (s, 1H), 6.72 (s, 1H). $^{13}$C NMR (150 MHz, CDCl$_3$): δ 185.3 (C), 158.7 (C), 156.5 (C), 156.5 (C), 150.9 (C), 150.2 (C), 148.4 (C), 136.5 (C), 134.2 (q, J = 90.2 Hz, C), 133.0 (CH), 130.6 (CH × 2), 129.7 (CH × 2), 129.4 (CH), 128.9 (CH), 128.1 (CH × 2), 127.8 (CH × 2), 124.1 (CH), 116.9 (C), 112.8 (CH), 110.5 (C), 109.4 (CH). |
| 12 | $^1$H NMR (600 MHz, CDCl$_3$): δ 7.77-7.75 (m, 2H), 7.58 (d, J = 9.0 Hz, 1H), 7.53-7.52 (m, 3H), 7.50-7.47 (m, 3H), 7.50-7.42 (m, 3H), 7.33-7.32 (m, 3H), 7.29-7.27 (m, 2H), 6.31 (s, 1H). $^{13}$C NMR (100 MHz, CDCl$_3$): δ 185.5, 159.4, 156.6, 156.3, 150.7, 148.2, 136.6, 135.7, 132.9, 130.7, 129.8, 129.7, 128.9, 128.8, 128.3, 128.1, 127.8, 126.7, 116.6, 114.5, 114.2, 113.6, 108.9. HRMS (M$^+$): Calcd. for C$_{30}$H$_{18}$O$_4$ 442.1205, found 442.1206. |
| 14 | $^1$H NMR (300 MHz, CDCl$_3$): δ 7.77-7.72 (m, 3H), 7.53-7.41 (m, 4H), 7.31-7.31 (m, 5H), 6.20 (s, 1H), 2.76 (t, J = 7.6 Hz, 2H), 1.76-1.71 (m, 2H), 1.05 (t, J = 7.6 Hz, 3H). $^{13}$C NMR (75 MHz, CDCl$_3$): δ 185.3, 159.5, 156.1, 150.0, 147.9, 136.4, 132.7, 130.5, 129.5, 128.6, 127.9, 127.6, 123.9, 116.3, 114.5, 112.2, 108.7, 34.4, 21.3, 13.7. |
| 16 | $^1$H NMR (600 MHz, CDCl$_3$): δ 7.83~7.81 (m, 2H), 7.49-7.45 (m, 4H), 7.33-7.30 (m, 5H), 6.22 (s, 1H), 6.11-6.05 (m, 1H), 5.24-5.20 (m, 2H), 3.76-3.75 (m, 2H), 2.47 (s, 3H). $^{13}$C NMR (150 MHz, CDCl$_3$): δ 185.1 (C), 159.7 (C), 154.9 (C), 152.8 (C), 148.6 (C), 148.0 (C), 136.7 (C), 134.8 (CH), 132.9 (CH), 130.6 (CH × 2), 129.8 (CH × 2), 129.7 (C), 129.0 (C), 128.7 (CH), 128.0 (CH × 2), 127.7 (CH × 2), 123.3 (CH), 121.4 (C), 117.4 (CH$_2$), 116.1 (C), 115.4 (C), 113.5 (CH), 33.5 (CH$_2$), 19.6 (CH$_3$). EIMS m/z (relative intensity): 420 (M$^+$, 100), 391 (10), 334 (53), 320 (70), 305 (11). HRMS Calcd. for C$_{28}$H$_{20}$O$_4$ 420.1362, found 420.1356. IR (neat): 2980, 2918, 1730, 1650, 1552, 1585, 1494, 1474, 1446, 1348, 1226, 1227, 1179, 1126 cm$^{-1}$. |
| 17 | $^1$H NMR (400 MHz, CDCl$_3$): δ 7.81-7.80 (m, 2H), 7.49-7.43 (m, 4H), 7.35-7.28 (m, 5H), 6.21 (s, 1H), 2.97 (t, J = 7.6 Hz, 2H), 2.47 (s, 3H), 1.84 (tq, J = 7.2, 7.6 Hz, 2H), 1.03 (t, J = 7.2 Hz, 3H). $^{13}$C NMR (100 MHz, CDCl$_3$): δ 185.3 (C), 159.7 (C), 155.2 (C), 152.8 (C), 148.3 (C), 147.9 (C), 136.8 (C), 132.8 (CH), 130.6 (CH × 2), 129.8 (C), 129.7 (CH × 2), 128.9 (C), 128.7 (CH), 128.1 (CH × 2), 127.7 (CH × 2), 123.8 (C), 123.2 (CH), 116.0 (C), 115.3 (C), 113.5 (CH), 31.5 (CH$_2$), 23.0 (CH$_2$), 19.6 (CH$_3$), 13.9 (CH$_3$). EIMS m/z (relative intensity): 422 (M$^+$, 5), 336 (26), 322 (100), 307 (40), 293 (95), 245 (41), 215 (93), 187 (68), 132 (15), 105 (63), 91 (42), 77 (54). HRMS Calcd. for C$_{28}$H$_{22}$O$_4$ 422.1518, found 422.1499. IR (neat): 2957, 2927, 2868, 1731, 1651, 1584, 1553, 1490, 1446, 1420, 1373, 1348, 1265, 1230, 1179, 1082 cm$^{-1}$. |
| 18 | $^1$H NMR (600 MHz, CDCl$_3$): δ 7.78-7.76 (m, 2H), 7.60 (s, 1H), 7.47-7.39 (m, 3H), 7.32-7.24 (m, 5H), 6.22 (q, J = 1.0 Hz, 1H), 3.40 (dd, J = 4.5, 14.7 Hz, 1H), 3.37-3.35 (m, 1H), 3.11 (dd, J = 6.1, 14.7 Hz, 1H), 2.86 (dd, J = 3.3, 7.8 Hz, 1H), 2.64 (dd, J = 2.5, 4.8 Hz, 1H), 2.48 (d, J = 1.0 Hz, 3H). $^{13}$C NMR (150 MHz, CDCl$_3$): δ 185.4 (C), 159.6 (C), 155.1 (C), 152.8 (C), 148.9 (C), 148.0 (C), 136.6 (C), 132.9 (CH), 130.6 (CH × 2), 129.7 (CH × 2), 129.5 (C), 129.0 (C), 128.8 (CH), 128.0 (CH × 2), 127.8 (CH × 2), 124.3 (CH), 118.5 (C), 116.1 (C), 115.5 (C), 113.6 (CH), 51.1 (CH), 47.1 (CH$_2$), 32.4 (CH$_2$), 19.6 (CH$_3$). EIMS m/z (relative intensity): 436 (M$^+$, 39), 395 (100), 380 (72), 208 (30), 204 (42), 191 (54), 172 (67), 144 (57), 105 (40), 77 (23). HRMS Calcd. for C$_{28}$H$_{20}$O$_5$ 436.1311, found 436.1294. IR (neat): 2985, 2952, 2918, 1731, 1651, 1553, 1492, 1474, 1446, 1367, 1349, 1267, 1227, 1181, 1124 cm$^{-1}$. |

TABLE 1-continued

| Cpd# | Analytical Data |
|---|---|
| 19 | LCMS [M + 1]$^+$: 471.1 |
| 20 | $^1$H NMR (600 MHz, CDCl$_3$): δ 7.76~7.75 (m, 2H), 7.56-7.53 (m, 2H), 7.47-7.38 (m, 3H), 7.31-7.26 (m, 5H), 3.14 (t, J = 7.1 Hz, 2H), 2.89 (t, J = 7.5 Hz, 2H), 2.22-2.19 (tt, J = 7.1, 7.5 Hz, 2H). $^{13}$C NMR (150 MHz, CDCl$_3$): δ 185.6 (C), 158.8 (C), 156.3 (C), 156.1 (C), 150.2 (C), 148.0 (C), 142.2 (C), 136.7 (C), 132.8 (CH), 130.7 (CH × 2), 129.7 (CH × 2), 128.7 (CH), 128.2 (C), 128.1 (CH × 2), 127.8 (CH × 2), 126.2 (C), 124.5 (CH), 116.4 (C), 114.3 (C), 108.9 (CH), 32.7 (CH$_2$), 30.7 (CH$_2$), 22.4 (CH$_2$). EIMS m/z (relative intensity) 406 (M$^+$, 100), 377 (16). HRMS Calcd. for C$_{27}$H$_{18}$O$_4$ 406.1205, found 406.1202. IR (neat): 2957, 2851, 1727, 1650, 1600, 1549, 1490, 1479, 1447, 1369, 1283, 1237, 1071 cm$^{-1}$. |
| 21 | $^1$H NMR (600 MHz, CDCl$_3$): δ 7.76 (dd, J = 8.4, 1.2 Hz, 2H), 7.69 (d, J = 8.9 Hz, 1H), 7.53 (d, J = 8.9 Hz, 1H), 7.46-7.41 (m, 3H), 7.30-7.26 (m, 5H), 2.85-2.83 (m, 2H), 2.54-2.52 (m, 2H), 1.88-1.86 (m, 2H), 1.79-1.78 (m, 2H). $^{13}$C NMR (150 MHz, CDCl$_3$): δ 185.6, 160.4, 155.7, 147.9, 147.3, 136.7, 132.8, 130.1, 129.9, 129.8, 129.7, 128.8, 128.7, 128.0, 127.7, 123.1, 122.4, 116.2, 115.5, 108.6, 25.9, 24.0, 21.5. HRMS (M$^+$): Calcd. for C$_{28}$H$_{20}$O$_4$ 420.1263, found 420.1265. |
| 22 | $^1$H NMR (600 MHz, CDCl$_3$): δ 8.33 (d, J = 7.8 Hz, 1H), 8.18 (d, J = 8.8 Hz, 1H), 8.1 (d, J = 8.2 Hz, 1H), 7.84-7.81 (m, 1H), 7.78 (dd, J = 7.1, 1.3 Hz, 2H), 7.61 (dd, J = 8.7, 0.7 Hz, 1H), 7.54 (t, J = 7.5 Hz, 1H), 7.50-7.48 (m, 2H), 7.43 (t, J = 7.3 Hz, 1H), 7.33-7.27 (m, 5H). $^{13}$C NMR (150 MHz, CDCl$_3$): δ 185.6 (C), 159.9 (C), 155.8 (C), 148.1 (C), 147.0 (C), 136.7 (C), 135.0 (CH), 134.2 (C), 132.8 (CH), 132.5 (C), 130.7 (CH × 2), 130.6 (CH), 129.9 (C), 129.7 (CH), 128.7 (CH), 128.5 (CH), 128.1 (CH × 2), 127.7 (CH × 2), 122.7 (CH), 121.7 (CH), 120.4 (C), 117.0 (C), 113.1 (C), 109.2 (CH). EIMS m/z (relative intensity) 415 (M+, 4), 316 (75), 315 (100), 239 (28), 105 (23), 77 (13). HRMS Calcd. for C28H16O4 416.1049, found 416.1033. IR (neat): 2924, 2851, 1737, 1650, 1599, 1552, 1488, 1446, 1353, 1310, 1237, 1096 cm$^{-1}$. |
| 26 | $^1$H NMR (600 MHz, CDCl$_3$): δ 7.78 (d, J = 8.6 Hz, 1H), 7.65 (d, J = 8.6 Hz, 1H), 7.58 (dd, J = 1.0, 7.2 Hz, 2H), 7.34-7.29 (m, 3H), 7.19-7.16 (m, 5H), 6.21 (q, J = 0.8 Hz, 1H), 2.47 (d, J = 0.8 Hz, 3H). $^{13}$C NMR (150 MHz, CDCl$_3$): δ 191.4 (C), 159.0 (C), 152.6 (C), 151.1 (C), 144.1 (C), 140.4 (C), 139.3 (C), 137.0 (C), 134.2 (C), 132.7 (CH), 130.6 (CH × 2), 129.5 (CH × 2), 128.3 (CH), 127.9 (CH × 2), 127.4 (CH × 2), 126.7 (C), 112.4 (CH), 118.5 (CH), 116.1 (CH), 114.2 (CH), 19.5 (CH$_3$). EIMS m/z (relative intensity): 396 (M$^+$, 8), 367 (4), 302 (4), 287 (6), 252 (5), 125 (7), 84 (100). HRMS Calcd. for C$_{25}$H$_{16}$O$_3$S 396.082, found 396.0815. IR (neat): 2924, 2854, 1737, 1653, 1590, 1508, 1450, 1378, 1330, 1264, 1175, 1108 cm$^{-1}$. |
| 30 | $^1$H NMR (300 MHz, CDCl$_3$): δ 7.70 (d, J = 9.0 Hz, 1H), 7.55 (d, J = 8.7 Hz, 1H), 7.37 (dd, J = 7.2, 1.8 Hz, 1H), 7.33-7.29 (m, 2H), 7.26-7.17 (m, 4H), 6.86 (td, J = 7.4, 0.7 Hz, 1H), 6.52 (d, J = 8.4 Hz, 1H), 6.21 (d, J = 1.2 Hz, 1H), 3.57 (s, 3H), 2.48 (d, J = 1.2 Hz, 3H). $^{13}$C NMR (100 MHz, CDCl$_3$): δ 185.5, 159.5, 157.3, 156.4, 152.9, 150.1, 149.1, 132.8, 130.3, 123.0, 129.3, 128.5, 128.4, 127.9, 127.1, 124.2, 120.2, 116.6, 115.1, 113.3, 110.5, 109.0, 55.2, 19.5. |
| 31 | $^1$H NMR (300 MHz, CDCl$_3$): δ 7.73 (d, J = 8.7 Hz, 1H), 7.57 (d, J = 9.0 Hz, 1H), 7.50-7.47 (m, 2H), 7.40-7.28 (m, 5H), 7.20 (t, J = 8.4 Hz, 1H), 7.01-6.97 (m, 1H), 6.24 (d, J = 1.2 Hz, 1H), 3.76 (s, 3H), 2.49 (d, J = 1.2 Hz, 3H). $^{13}$C NMR (75 MHz, CDCl$_3$): δ 185.2, 159.5, 159.2, 156.4, 152.8, 149.9, 148.1, 137.8, 130.6, 129.7, 129.1, 128.8, 127.7, 124.2, 122.5, 119.7, 116.3, 115.3, 113.7, 113.5, 108.9, 55.3, 19.5. |
| 32 | $^1$H NMR (300 MHz, CDCl$_3$): δ 7.82 (dd, J = 10.2, 2.4 Hz, 2H), 7.70 (dd, J = 9.0, 1.5 Hz, 1H), 7.56-7.47 (m, 3H), 7.37-7.32 (m, 3H), 6.79 (dd, J = 8.7, 2.7 Hz, 2H), 6.30 (d, J = 1.5, 0.9 Hz, 1H), 3.81 (s, 3H), 2.48 (d, J = 0.9 Hz, 3H). |
| 33 | $^1$H NMR (400 MHz, CDCl$_3$): δ 7.77 (d, J = 8.4 Hz, 1H), 7.58 (dd, J = 8.4, 0.4 Hz, 1H), 7.48-7.46 (m, 2H), 7.34 (t, J = 2.4 Hz, 4H), 7.24-7.23 (m, 1H), 7.16 (t, J = 8.0 Hz, 1H), 6.94 (ddd, J = 8.0, 2.4, 0.8 Hz, 1H), 6.26 (s, 1H), 2.51 (s, 3H). LCMS [M + 1]$^+$: 397.1. |
| 34 | $^1$H NMR (300 MHz, CDCl$_3$): δ 7.71-7.58 (m, 3H), 7.51 (d, J = 8.7 Hz, 1H), 7.44-7.41 (m, 2H), 7.28-7.25 (m, 3H), 6.69-6.66 (m, 2H), 6.15 (d, J = 1.2 Hz, 1H), 2.43 (d, J = 1.2 Hz, 3H). $^{13}$C NMR (75 MHz, CDCl$_3$): δ 182.6, 161.7, 158.6, 155.2, 152.6, 148.5, 147.6, 131.5, 129.7, 129.2, 127.4, 126.7, 125.7, 123.1, 115.0, 114.3, 112.1, 108.0, 18.6. |
| 35 | $^1$H NMR (300 MHz, CDCl$_3$): δ 7.77-7.21 (m, 11H), 6.23 (d, J = 0.9 Hz, 1H), 2.49 (d, J = 0.9 Hz, 3H). |
| 36 | $^1$H NMR (300 MHz, CDCl$_3$): δ 7.95-7.29 (m, 11H), 6.26 (d, J = 1.2 Hz, 1H), 2.51 (d, J = 1.2 Hz, 3H). $^{13}$C NMR (75 MHz, CDCl$_3$): δ 184.2, 159.3, 156.6, 152.8, 150.1, 147.5, 137.2, 132.5, 130.8, 130.7, 130.4, 129.8, 129.2, 129.14, 129.06, 128.8, 127.9, 126.45, 126.40, 124.8, 116.3, 115.5, 113.7, 109.0, 19.5. |
| 37 | $^1$H NMR (300 MHz, CDCl$_3$): δ 7.84-7.30 (m, 11H), 6.25 (s, 1H), 2.49 (s, 3H). $^{13}$C NMR (75 MHz, CDCl$_3$): δ 184.3, 159.3, 156.5, 152.8, 150.1, 147.6, 139.6, 134.0, 133.5, 130.6, 129.9, 129.7, 129.3, 129.1, 127.8, 125.2, 125.01, 124.95, 124.9, 124.8, 116.3, 115.5, 113.7, 108.9, 19.5. |
| 38 | $^1$H NMR (300 MHz, CDCl$_3$): δ 7.80-7.08 (m, 11H), 6.26 (d, J = 0.9 Hz, 1H), 2.50 (d, J = 0.6 Hz, 3H). |
| 39 | $^1$H NMR (300 MHz, CDCl$_3$): δ 7.75-6.93 (m, 11H), 6.24 (d, J = 1.2 Hz, 1H), 2.42 (s, 3H), 2.18 (s, 3H). |
| 40 | $^1$H NMR (300 MHz, CDCl$_3$): δ 7.75-7.18 (m, 11H), 6.26 (s, 1H), 2.51 (d, J = 0.6 Hz, 3H), 2.25 (s, 3H). |
| 41 | $^1$H NMR (300 MHz, CDCl$_3$): δ 7.73-7.69 (m, 3H), 7.55 (d, J = 8.7 Hz, 1H), 7.51-7.47 (m, 2H), 7.36-7.32 (m, 3H), 7.11 (d, J = 8.1 Hz, 2H), 6.24 (d, J = 0.9 Hz, 1H), 2.49 (d, J = 0.6 Hz, 3H), 2.35 (s, 3H). $^{13}$C NMR (100 MHz, CDCl$_3$): δ 185.1, 159.5, 156.3, 152.8, 149.9, 148.3, 143.9, 133.9, 130.6, 129.9, 129.7, 128.8, 128.7, 128.6, 128.2, 127.7, 124.0, 116.3, 115.3, 113.5, 108.9, 21.6, 19.5. |

TABLE 1-continued

| Cpd# | Analytical Data |
|---|---|
| 42 | $^1$H NMR (300 MHz, CDCl$_3$): δ 7.98-7.95 (m, 2H), 7.78 (d, J = 8.7 Hz, 1H), 7.70-7.67 (m, 1H), 7.60 (d, J = 9.0 Hz, 1H), 7.46-7.40 (m, 3H), 7.36-7.32 (m, 3H), 6.26 (d, J = 1.2 Hz, 1H), 2.51 (d, J = 0.9 Hz, 3H). |
| 43 | $^1$H NMR (300 MHz, CDCl$_3$): δ 7.79-7.74 (m, 3H), 7.58-7.53 (m, 3H), 7.42-7.39 (m, 2H), 7.37-7.29 (m, 3H), 6.25 (d, J = 1.2H, 1H), 2.49 (s, 3H). |
| 44 | $^1$H NMR (300 MHz, CDCl$_3$): δ 7.74 (d, J = 9.0 Hz, 1H), 7.56 (d, J = 9.0 Hz, 1H), 7.51-6.78 (m, 9H), 6.24 (d, J = 1.2 Hz, 1H), 2.49 (d, J = 1.2 Hz, 3H). |
| 45 | $^1$H NMR (300 MHz, CDCl$_3$): δ 7.77 (d, J = 8.7 Hz, 1H), 7.57 (d, J = 8.7 Hz, 1H), 7.57-7.11 (m, 9H), 6.26 (d, J = 1.2 Hz, 1H), 2.51 (d, J = 1.2 Hz, 3H). LCMS [M + 1]$^+$: 415.0. |
| 46 | $^1$H NMR (300 MHz, CDCl$_3$): δ 7.84-7.79 (m, 2H), 7.74 (d, J = 9.0 Hz, 1H), 7.58 (d, J = 8.7 Hz, 1H), 7.48-7.45 (m, 2H), 7.36-7.32 (m, 3H), 6.96-6.94 (m, 2H), 6.26 (d, J = 0.9 Hz, 1H), 2.50 (d, J = 0.6 Hz, 3H). $^{13}$C NMR (100 MHz, CDCl$_3$): δ 183.9, 166.7, 164.2, 159.4, 156.5, 152.8, 150.0, 147.9, 132.9, 132.8, 132.4, 132.3, 130.6, 129.5, 128.9, 128.8, 127.8, 124.3, 116.3, 115.41, 115.39, 115.2, 113.6, 108.9, 19.6. |
| 47 | $^1$H NMR (600 MHz, CDCl$_3$): δ 7.71 (d, J = 8.8 Hz, 1H), 7.53 (dd, J = 1.8, 8.8 Hz, 1H), 7.36-7.24 (m, 2H), 7.27-7.07 (m, 7H), 6.20 (s, 1H), 2.45 (s, 3H). $^{13}$C NMR (150 MHz, CDCl$_3$): δ 184.5 (C), 159.3 (C), 156.6 (C), 152.8 (C), 150.2 (C), 147.9 (C), 137.4 (C), 131.7 (CH), 130.3 (C), 130.2 (CH × 2), 129.72 (CH), 129.65 (CH), 128.9 (C), 128.7 (CH), 127.4 (CH × 2), 126.4 (CH), 125.0 (CH), 116.7 (C), 115.3 (CH), 113.5 (CH), 109.0 (CH), 29.6 (C), 19.5 (CH$_3$). EIMS m/z (relative intensity) 416 (14), 414 (M$^+$, 34), 84 (100). HRMS Calcd. for C$_{25}$H$_{15}$ClO$_4$ 414.0659, found 414.0666. IR (neat): 2923, 2853, 1734, 1657, 1628, 1603, 1555, 1493, 1471, 1434, 1378, 1357, 1272, 1180, 1152, 1080 cm$^{-1}$. |
| 48 | $^1$H NMR (300 MHz, CDCl$_3$): δ 7.64-7.37 (m, 11H), 6.23 (d, J = 1.2 Hz, 1H), 2.50 (d, J = 1.2 Hz, 3H). $^{13}$C NMR (75 MHz, CDCl$_3$): δ 184.0, 159.3, 156.5, 152.8, 150.0, 147.6, 138.1, 134.2, 132.7, 130.5, 129.6, 129.5, 129.4, 129.0, 127.8, 127.6, 124.6, 116.3, 115.4, 113.6, 109.0, 19.5. |
| 49 | $^1$H NMR (300 MHz, CDCl$_3$): δ 7.76-7.71 (m, 3H), 7.57 (d, J = 8.7 Hz, 1H), 7.48-7.44 (m, 2H), 7.38-7.32 (m, 3H), 7.29-7.24 (m, 2H), 6.25 (d, J = 1.2 Hz, 1H), 2.50 (d, J = 1.2 Hz, 3H). $^{13}$C NMR (100 MHz, CDCl$_3$): δ 184.1, 159.4, 156.4, 152.8, 150.0, 147.8, 139.2, 134.9, 131.0, 130.6, 129.4, 129.1, 128.9, 128.4, 127.9, 124.4, 116.3, 115.4, 113.6, 108.9, 19.5. |
| 50 | $^1$H NMR (300 MHz, CDCl$_3$): δ 7.75-7.34 (m, 11H), 6.25 (d, J = 0.6 Hz, 1H), 2.50 (d, J = 0.6 Hz, 3H). $^{13}$C NMR (75 MHz, CDCl$_3$): δ 184.2, 159.4, 156.4, 152.8, 150.0, 147.8, 135.3, 131.4, 131.1, 130.6, 129.4, 129.2, 128.9, 128.0, 127.9, 124.5, 116.3, 115.4, 113.6, 108.9, 19.5. |
| 51 | $^1$H NMR (300 MHz, CDCl$_3$): δ 8.14-8.09 (m, 2H), 7.89-7.85 (m, 2H), 7.79 (d, J = 9.0 Hz, 1H), 7.59 (d, J = 8.7 Hz, 1H), 7.46-7.43 (m, 2H), 7.36-7.30 (m, 3H), 6.27 (d, J = 0.9 Hz, 1H), 2.52 (d, J = 1.2 Hz, 3H). |
| 52 | $^1$H NMR (300 MHz, CDCl$_3$): δ 7.87-7.83 (m, 2H), 7.73 (d, J = 8.7 Hz, 1H), 7.59-7.30 (m, 13H), 6.25 (d, J = 1.2 Hz, 1H), 2.49 (d, J = 1.2 Hz, 3H). $^{13}$C NMR (100 MHz, CDCl$_3$): δ 185.5, 159.5, 157.3, 156.4, 152.7, 150.1, 149.1, 132.8, 130.3, 130.0, 129.3, 128.5, 128.4, 127.9, 127.1, 124.2, 120.2, 116.6, 115.1, 113.3, 110.5, 109.0, 55.2, 19.5. |
| 53 | $^1$H NMR (300 MHz, CDCl$_3$): δ 8.23 (dd, J = 7.8, 1.8 Hz, 1H), 7.81-7.73 (m, 3H), 7.61-7.48 (m, 4H), 7.23-6.98 (m, 7H), 6.23 (d, J = 0.9 Hz, 1H), 2.50 (d, J = 0.9 Hz, 3H). |
| 54 | $^1$H NMR (300 MHz, CDCl$_3$): δ 8.31 (d, J = 0.6 Hz, 1H), 7.88-7.25 (m, 13H), 6.25 (d, J = 0.6 Hz, 1H), 2.49 (d, J = 1.2 Hz, 3H). $^{13}$C NMR (75 MHz, CDCl$_3$): δ 185.3, 159.5, 156.5, 152.8, 149.9, 148.4, 135.3, 133.7, 132.1, 132.0, 130.6, 129.7, 129.4, 128.6, 128.5, 128.0, 127.8, 127.6, 126.6, 124.9, 124.1, 116.4, 115.3, 113.5, 109.0, 19.5. |
| 55 | $^1$H NMR (300 MHz, CDCl$_3$): δ 7.81-7.44 (m, 4H), 7.72-7.47 (m, 5H), 7.32-7.29 (m, 3H), 6.25 (d, J = 1.2 Hz, 1H), 2.51 (d, J = 1.2 Hz, 3H), 2.14 (s, 3H). $^{13}$C NMR (75 MHz, CDCl$_3$): δ 184.0, 168.7, 159.7, 156.4, 153.2, 149.8, 148.3, 142.6, 131.8, 131.3, 130.5, 129.7, 128.7, 128.1, 127.8, 124.1, 118.3, 116.3, 115.4, 113.4, 109.0, 24.7, 19.6. |
| 56 | $^1$H NMR (300 MHz, CDCl$_3$): δ 7.67 (d, J = 9.0 Hz, 1H), 7.52 (d, J = 8.7 Hz, 1H), 7.40 (d, J = 8.4 Hz, 1H), 7.37-7.33 (m, 2H), 7.26-7.21 (m, 3H), 6.38 (dd, J = 2.1, 8.4 Hz, 1H), 6.20 (d, J = 1.2 Hz, 1H), 6.03 (d, J = 2.4 Hz, 1H), 3.76 (s, 3H), 3.52 (s, 3H), 2.46 (s, 3H). |
| 57 | $^1$H NMR (300 MHz, CDCl$_3$): δ 7.76 (d, J = 9.0 Hz, 1H), 7.56 (d, J = 9.0 Hz, 1H), 7.37-7.08 (m, 8H), 6.23 (d, J = 1.2 Hz, 1H), 2.49 (d, J = 1.2 Hz, 3H). $^{13}$C NMR (75 MHz, CDCl$_3$): δ 159.3, 156.7, 152.7, 137.3, 135.9, 132.8, 130.6, 130.2, 129.7, 128.9, 128.8, 127.6, 126.8, 125.1, 115.4, 113.7, 109.0, 19.5. |
| 58 | $^1$H NMR (600 MHz, CDCl$_3$): δ 7.73 (d, J = 8.9 Hz, 1H), 7.59-7.54 (m, 2H), 7.44-7.43 (m, 3H), 7.35-7.33 (m, 4H), 6.23 (q, J = 1.0 Hz, 1H), 2.48 (d, J = 1.0 Hz, 3H). $^{13}$C NMR (150 MHz, CDCl$_3$): δ 182.9 (C), 159.3 (C), 156.5 (C), 152.7 (C), 150.0 (C), 147.4 (C), 137.3 (C), 136.1 (C), 132.6 (C), 131.6 (CH), 130.5 (CH × 2), 130.2 (CH), 129.8 (C), 129.3 (C), 129.1 (CH), 128.5 (CH), 127.9 (CH × 2), 124.8 (CH), 116.3 (C), 115.5 (C), 113.7 (CH), 108.9 (CH), 19.5 (CH$_3$). EIMS m/z (relative intensity) 448 (M$^+$, 100), 450 (59), 452 (12), 419 (31), 269 (56), 195 (80), 189 (51), 175 (47), 145 (67), 75 (62). HRMS Calcd. for C$_{25}$H$_{14}$Cl$_2$O$_4$ 448.0269, found 448.0269. IR (neat): 1736, 1649, 1627, 1602, 1553, 1490, 1467, 1443, 1381, 1354, 1267, 1238, 1176, 1152, 1130, 1079, 1030, 1001 cm$^{-1}$. |
| 59 | $^1$H NMR (300 MHz, CDCl$_3$): δ 7.72 (d, J = 8.7 Hz, 1H), 7.54 (d, J = 8.7 Hz, 1H), 7.49 (dd, J = 8.7, 1.8 Hz, 1H), 7.41-7.38 (m, 2H), 7.31-7.27 (m, 3H), 6.79 (td, J = 8.4, 2.4 Hz, 1H), 6.56-6.49 (m, 1H), 6.22 (s, 1H), 2.47 (s, 3H). |

TABLE 1-continued

| Cpd# | Analytical Data |
|---|---|
| 60 | $^1$H NMR (600 MHz, CDCl$_3$): δ 7.74 (d, J = 8.9 Hz, 1H), 7.65-7.62 (m, 1H), 7.57-7.54 (m, 2H), 7.46-7.44 (m, 2H), 7.36-7.33 (m, 3H), 7.06 (dd, J = 8.4, 17.2 Hz, 1H), 6.24 (q, J = 1.0 Hz, 1H), 2.49 (d, J = 1.0 Hz, 3H). $^{13}$C NMR (150 MHz, CDCl$_3$): δ 182.6 (C), 159.3 (C), 156.5 (C), 153.3 (dd, J = 256.2, 12.8 Hz, C), 152.7 (C), 150.0 (C), 149.9 (dd, J = 249.5, 13.1 Hz, C), 147.4 (C), 133.5 (C), 130.5 (CH × 2), 129.5 (C), 129.4 (C), 129.1 (CH), 127.9 (CH × 2), 126.8 (d, J = 4.1 Hz, CH), 124.69 (CH), 119.0 (d, J = 18.3 Hz, CH), 117.1 (d, J = 17.7 Hz, CH), 116.3 (C), 115.5 (C), 113.7 (CH), 108.9 (CH), 19.5 (CH$_3$). EIMS m/z (relative intensity) 416 (M$^+$, 100), 387 (33), 141 (70), 113 (60), 84 (52), 77 (17). HRMS Calcd. for C$_{25}$H$_{14}$F$_2$O$_4$ 416.086, found 416.0857. IR (neat): 1737, 1656, 1650, 1604, 1555, 1514, 1493, 1473, 1430, 1379, 1355, 1289, 1236, 1203, 1161, 1111, 1079 cm$^{-1}$. |
| 61 | $^1$H NMR (300 MHz, CDCl$_3$): δ 7.75 (d, J = 8.7 Hz, 1H), 7.56 (d, J = 8.7 Hz, 1H), 7.44-7.41 (m, 2H), 7.32-7.28 (m, 3H), 7.19-7.13 (m, 1H), 7.04-6.96 (m, 1H), 6.78 (td, J = 8.9, 4.4 Hz, 1H), 6.24 (d, J = 1.2 Hz, 1H), 2.490 (d, J = 1.2 Hz, 3H). $^{13}$C NMR (100 MHz, CDCl$_3$): δ 180.9, 159.42, 159.38, 159.3, 157.11, 157.08, 156.97, 156.92, 156.6, 154.62, 154.59, 152.7, 150.2, 147.8, 130.5, 130.4, 129.0, 128.8, 127.55, 127.46, 127.37, 127.30, 125.1, 120.24, 120.15, 120.0, 119.9, 117.4, 117.3, 117.2, 117.1, 116.72, 116.68, 116.53, 116.47, 116.43, 115.4, 113.6, 109.0, 19.5. |
| 62 | $^1$H NMR (300 MHz, CDCl$_3$): δ 7.71 (d, J = 9.0 Hz, 1H), 7.53 (d, J = 8.7 Hz, 1H), 7.40-7.36 (m, 2H), 7.28-7.20 (m, 3H), 7.19 (d, J = 7.5 Hz, 1H), 6.92 (s, 1H), 6.77 (d, J = 8.1 Hz, 1H), 6.23 (d, J = 1.2 Hz, 1H), 2.48 (d, J = 0.6 Hz, 3H), 2.38 (s, 3H), 2.25 (s, 3H). $^{13}$C NMR (100 MHz, CDCl$_3$): δ 187.4, 159.5, 156.4, 152.8, 150.0, 148.8, 141.6, 137.7, 134.1, 131.7, 130.3, 129.9, 129.5, 128.7, 128.4, 127.5, 125.7, 124.3, 116.5, 115.2, 113.5, 109.0, 21.3, 19.9, 19.5. |
| 63 | $^1$H NMR (400 MHz, CDCl$_3$): δ 7.77 (d, J = 6.6 Hz, 1H), 7.85-7.21 (m, 8H), 6.74 (d, J = 6.3 Hz, 1H), 6.29 (d, J = 0.9 Hz, 1H), 6.02 (s, 2H), 2.50 (d, J = 0.9 Hz, 3H). |
| 64 | $^1$H NMR (300 MHz, CDCl$_3$): δ 7.85-7.32 (m, 8H), 7.76 (d, J = 8.7 Hz, 1H), 6.79 (d, J = 8.7 Hz, 1H), 6.29 (d, J = 1.2 Hz, 1H), 4.30-4.28 (m, 2H), 4.25-4.22 (m, 2H), 2.50 (d, J = 1.2 Hz, 3H). |
| 65 | $^1$H NMR (300 MHz, CDCl$_3$): δ 7.89 (br, NH), 7.73 (d, J = 8.7 Hz, 1H), 7.57 (d, J = 8.7 Hz, 1H), 7.52-7.45 (m, 3H), 7.36-7.34 (m, 3H), 7.24 (d, J = 1.8 Hz, 1H), 6.87 (d, J = 8.4 Hz, 1H), 6.26 (d, J = 1.2 Hz, 1H), 4.65 (s, 2H), 2.51 (d, J = 0.9 Hz, 3H). |
| 66 | $^1$H NMR (300 MHz, CDCl$_3$): δ 8.50 (t, J = 2.0 Hz, 1H), 8.25 (dd, J = 8.1, 1.2 Hz, 1H), 8.08 (d, J = 7.8 Hz, 1H), 7.79 (d, J = 8.7 Hz, 1H), 7.62 (d, J = 9.0 Hz, 1H), 7.51 (t, J = 8.0 Hz, 1H), 7.465-7.42 (m, 2H), 7.31-7.26 (m, 3H), 6.27 (s, 1H), 2.52 (d, J = 0.6 Hz, 3H). |
| 67 | LCMS [M + 1]+: 396.1. |
| 68 | $^1$H NMR (300 MHz, CDCl$_3$): δ 7.73 (d, J = 8.7 Hz, 1H), 7.78 (d, J = 9.0 Hz, 1H), 7.50-7.46 (m, 2H), 7.37-7.27 (m, 5H), 7.18 (dd, J = 8.4, 8.8 Hz, 1H), 7.00-6.96 (m, 1H), 6.25 (d, J = 0.9 Hz, 1H), 3.98 (q, J = 6.9 Hz, 2H), 2.50 (d, J = 1.2 Hz, 3H), 1.40 (t, J = 6.9 Hz, 3H). $^{13}$C NMR (75 MHz, CDCl$_3$): δ 185.3, 159.5, 158.6, 156.4, 152.9, 149.9, 148.1, 137.7, 130.6, 129.7, 129.1, 128.8, 128.7, 127.7, 124.2, 122.4, 120.1, 116.3, 115.3, 114.3, 113.5, 109.0, 63.6, 19.6, 14.7. |
| 69 | $^1$H NMR (300 MHz, CDCl$_3$): δ 7.73 (d, J = 8.7 Hz, 1H), 7.77 (d, J = 8.7 Hz, 1H), 7.50-7.46 (m, 2H), 7.37-7.26 (m, 5H), 7.21-7.15 (m, 1H), 7.00-6.96 (m, 1H), 6.26 (d, J = 1.2 Hz, 1H), 3.86 (d, J = 6.6 Hz, 2H), 2.50 (d, J = 1.2 Hz, 3H), 1.81-1.72 (m, 2H), 1.02 (t, J = 7.5 Hz, 1H). $^{13}$C NMR (75 MHz, CDCl$_3$): δ 185.4, 159.5, 158.8, 156.4, 152.9, 149.9, 148.1, 137.7, 132.3, 130.6, 130.1, 129.7, 129.2, 129.1, 128.7, 128.6, 128.2, 127.9, 127.7, 124.2, 122.3, 120.1, 120.0, 116.3, 115.3, 114.5, 114.4, 113.502, 109.0, 69.6, 22.4, 19.6, 10.5. |
| 70 | $^1$H NMR (300 MHz, CDCl$_3$): δ 7.73 (d, J = 9.0 Hz, 1H), 7.58 (d, J = 8.7 Hz, 1H), 7.49-7.46 (m, 2H), 7.37-7.26 (m, 5H), 7.18 (dd, J = 7.8, 7.8 Hz, 1H), 7.00-6.96 (m, 1H), 6.25 (d, J = 1.2 Hz, 1H), 3.90 (t, J = 6.9 Hz, 2H), 2.60 (d, J = 1.2 Hz, 3H), 1.78-1.70 (m, 2H), 1.51-1.43 (m, 2H), 0.97 (t, J = 7.2 Hz, 3H). $^{13}$C NMR (75 MHz, CDCl$_3$): δ 185.4, 159.5, 158.8, 156.4, 152.9, 149.9, 148.1, 137.7, 130.6, 129.7, 129.1, 128.7, 128.6, 127.7, 124.2, 122.3, 120.1, 116.3, 115.3, 114.4, 113.5, 109.0, 67.8, 31.1, 19.6, 19.2, 13.8. |
| 71 | $^1$H NMR (300 MHz, CDCl$_3$): δ 7.73 (d, J = 9.0 Hz, 1H), 7.77 (d, J = 9.0 Hz, 1H), 7.49-7.46 (m, 2H), 7.37-7.26 (m, 5H), 7.18 (dd, J = 7.8, 7.8 Hz, 1H), 7.00-6.96 (m, 1H), 6.25 (d, J = 0.9 Hz, 1H), 3.89 (t, J = 6.6 Hz, 2H), 2.50 (s, 3H), 1.78-1.73 (m, 2H), 1.44-1.36 (m, 4H), 0.93 (d, J = 6.9 Hz, 3H). $^{13}$C NMR (75 MHz, CDCl$_3$): δ 185.4, 159.5, 158.8, 156.4, 152.9, 149.9, 148.1, 137.7, 130.6, 129.6, 129.0, 128.7, 128.6, 127.7, 124.2, 122.3, 120.1, 116.3, 115.3, 114.4, 113.5, 109.0, 68.1, 28.8, 28.1, 22.4, 19.6, 14.0. |
| 72 | $^1$H NMR (300 MHz, CDCl$_3$): δ 7.69 (d, J = 9.0 Hz, 1H), 7.52 (d, J = 9.0 Hz, 1H), 7.49-7.46 (m, 2H), 7.37-7.26 (m, 5H), 7.19-7.14 (m, 1H), 6.99-6.95 (m, 1H), 6.21 (d, J = 0.9 Hz, 1H), 3.88 (t, J = 6.6 Hz, 2H), 2.45 (d, J = 0.9 Hz, 1H), 1.77-1.72 (m, 2H), 1.44-1.25 (m, 6H), 0.90 (d, J = 6.6 Hz, 1H). $^{13}$C NMR (75 MHz, CDCl$_3$): δ 185.1, 159.3, 158.7, 156.3, 152.8, 149.7, 148.0, 137.6, 130.5, 129.6, 129.0, 128.6, 128.4, 127.6, 124.1, 122.1, 119.9, 116.1, 115.2, 114.3, 113.3, 108.8, 68.0, 31.4, 28.9, 25.5, 22.4, 19.4, 13.9. |
| 73 | $^1$H NMR (300 MHz, CDCl$_3$): δ 7.75 (d, J = 9.0 Hz, 1H), 7.59 (d, J = 9.0 Hz, 1H), 7.50-7.45 (m, 2H), 7.42 (dt, J = 7.8, 1.2 Hz, 1H), 7.36-7.27 (m, 5H), 7.21 (t, J = 8.1 Hz, 1H), 7.02 (ddd, J = 8.1, 2.4, 0.9 Hz, 1H), 6.27 (d, J = 1.2 Hz, 1H), 4.18 (t, J = 6.0 Hz, 2H), 3.79 (t, J = 6.0 Hz, 2H), 2.51 (d, J = 1.2 Hz, 3H). |
| 74 | $^1$H NMR (300 MHz, CDCl$_3$): δ 7.74 (d, J = 9.0 Hz, 1H), 7.59 (d, J = 9.0 Hz, 1H), 7.50-7.46 (m, 2H), 7.39 (d, J = 7.5 Hz, 1H), 7.34~7.32 (m, 3H), 7.28-7.26 (m, 1H), 7.20 (t, J = 8.1 Hz, 1H), 6.99 (dd, J = 7.2, 2.1 Hz, 1H), 6.26 (d, J = 1.2 Hz, 1H), 4.06 (t, J = 6.0 Hz, 2H), 3.73 (t, J = 6.0 Hz, 2H), 2.52 (d, J = 1.2 Hz, 3H), 2.21 (quin, J = 6.0 Hz, 2H). |

TABLE 1-continued

| Cpd# | Analytical Data |
|---|---|
| 75 | ¹H NMR (300 MHz, CDCl$_3$): δ 7.75 (d, J = 8.7 Hz, 1H), 7.59 (d, J = 8.7 Hz, 1H), 7.50-7.47 (m, 2H), 7.37 (dt, J = 7.8, 1.2 Hz, 1H), 7.35-7.30 (m, 3H), 7.28-7.24 (m, 1H), 7.19 (t, J = 7.8 Hz, 1H), 6.98 (dd, J = 7.2, 2.7 Hz, 1H), 6.26 (s, 1H), 3.94 (t, J = 6.0 Hz, 2H), 3.62 (t, J = 6.0 Hz, 2H), 2.15 (d, J = 1.2 Hz, 3H), 1.98~1.90 (m, 4H). |
| 76 | ¹H NMR (300 MHz, CDCl$_3$): δ 7.74 (d, J = 8.7 Hz, 1H), 7.58 (d, J = 8.7 Hz, 1H), 7.50-7.43 (m, 2H), 7.38 (dt, J = 7.8, 1.2 Hz, 1H), 7.34-7.30 (m, 4H), 7.22 (t, J = 8.4 Hz, 1H), 7.01 (dd, J = 8.4, 2.7 Hz, 1H), 6.26 (d, J = 1.2 Hz, 1H), 6.02 (dddd, J = 17.4, 10.5, 5.4, 5.4 Hz, 1H), 5.39 (ddd, J = 17.1, 3.0, 1.8 Hz, 1H), 5.30 (ddd, J = 10.5, 3.0, 1.5 Hz, 1H), 4.49 (ddd, J = 5.7, 1.5, 1.5 Hz, 2H), 2.51 (s, 3H). |
| 77 | ¹H NMR (300 MHz, CDCl$_3$): δ 7.74 (d, J = 9.0 Hz, 1H), 7.58 (d, J = 9.0 Hz, 1H), 7.49-7.46 (m, 2H), 7.38-7.27 (m, 5H), 7.18 (t, J = 7.8 Hz, 1H), 6.99 (dd, J = 8.1, 2.7 Hz, 1H), 6.26 (d, J = 0.9 Hz, 1H), 5.93-5.81 (m, 1H), 5.16 (dd, J = 17.1, 1.5 Hz, 1H), 5.11 (dd, J = 10.5, 1.2 Hz, 1H), 3.95 (t, J = 6.9 Hz, 2H), 2.51 (t, J = 6.9 Hz, 2H), 2.51 (s, 3H). |
| 78 | ¹H NMR (300 MHz, CDCl$_3$): δ 7.73 (d, J = 9.0 Hz, 1H), 7.57 (d, J = 9.0 Hz, 1H), 7.50-7.46 (m, 2H), 7.37-7.26 (m, 5H), 7.18 (d, J = 8.1 Hz, 1H), 7.00-6.97 (dd, J = 8.1, 2.7 Hz, 1H), 6.25 (s, 1H), 5.91-5.78 (m, 1H), 5.10-4.99 (m, 1H), 3.91 (t, J = 6.0 Hz, 2H), 2.50 (s, 3H), 2.22 (q, J = 6.6 Hz, 2H), 1.86 (quin, J = 6.6 Hz, 2H). |
| 79 | ¹H NMR (300 MHz, CDCl$_3$): δ 7.73 (d, J = 9.0 Hz, 1H), 7.58 (d, J = 9.0 Hz, 1H), 7.50-7.45 (m, 2H), 7.37-7.27 (m, 5H), 7.18 (t, J = 8.1 Hz, 1H), 6.98 (ddd, J = 8.1, 1.8, 0.9 Hz, 1H), 6.25 (s, 1H), 5.90-5.76 (m, 1H), 5.08-4.96 (m, 2H), 4.90 (t, J = 6.6 Hz, 2H), 2.50 (s, 3H), 2.12 (q, J = 7.5 Hz, 2H), 1.78 (quin, J = 6.6 Hz, 2H), 1.60 (quin, J = 7.5 Hz, 2H). |
| 80 | ¹H NMR (300 MHz, CDCl$_3$): δ 7.74 (d, J = 8.7 Hz, 1H) 7.56 (d, J = 8.7 Hz, 1H), 7.50-7.47 (m, 2H), 7.38 (dt, J = 8.1, 1.2 Hz, 1H), 7.35-7.29 (m, 4H), 7.20 (t, J = 8.1 Hz, 1H), 7.00 (ddd, J = 8.1, 2.7, 1.2 Hz, 1H), 6.27 (d, J = 1.2 Hz, 1H), 4.06 (t, J = 5.7 Hz, 2H), 3.74 (t, J = 4.8 Hz, 2H), 2.79 (t, J = 5.7 Hz, 2H), 2.57 (t, J = 4.8 Hz, 2H), 2.51 (d, J = 1.2 Hz, 3H). |
| 81 | ¹H NMR (300 MHz, CDCl$_3$): δ 7.74 (d, J = 8.7 Hz, 1H), 7.58 (d, J = 8.7 Hz, 1H), 7.50-7.46 (m, 2H), 7.38~7.24 (m, 5H), 7.18 (t, J = 8.4 Hz, 1H), 6.89 (dd, J = 8.4, 1.8 Hz, 1H), 6.26 (d, J = 1.2 Hz, 1H), 3.97 (t, J = 6.0 Hz, 2H), 3.72 (t, J = 4.8 Hz, 4H), 2.51 (d, J = 1.2 Hz, 3H), 2.58~2.40 (m, 6H), 1.97 (quin, J = 7.8 Hz, 2H). |
| 82 | ¹H NMR (300 MHz, CDCl$_3$): δ 7.74 (d, J = 9 Hz, 1H), 7.58 (d, J = 9.0 Hz, 1H), 7.50-7.47 (m, 2H), 7.38-7.32 (m, 4H), 7.28-7.26 (m, 1H), 7.18 (t, J = 8.1 Hz, 1H), 6.98 (ddd, J = 8.1, 2.7, 0.9 Hz, 1H), 6.26 (d, J = 1.2 Hz, 1H), 3.93 (t, J = 6.0 Hz, 2H), 3.72 (t, J = 4.5 Hz, 4H), 2.51 (d, J = 1.2 Hz, 3H), 2.46 (t, J = 7.5 Hz, 4H), 2.40 (t, J = 7.5 Hz, 2H), 1.82-1.63 (m, 4H). |
| 83 | ¹H NMR (300 MHz, CDCl$_3$): δ 7.74 (d, J = 9.0 Hz, 1H), 7.59 (d, J = 9.0 Hz, 1H), 7.50-7.46 (m, 2H), 7.38-7.29 (m, 5H), 7.19 (t, J = 8.1 Hz, 1H), 7.00 (dt, J = 8.1, 2.7 Hz, 1H), 6.26 (d, J = 1.2 Hz, 1H), 4.06 (t, J = 6.3 Hz, 2H), 3.77 (t, J = 6.3 Hz, 2H), 2.51 (d, J = 1.2 Hz, 3H). |
| 84 | ¹H NMR (300 MHz, CDCl$_3$): δ 7.74 (d, J = 8.7 Hz, 1H), 7.59 (d, J = 8.7 Hz, 1H), 7.49-7.46 (m, 2H), 7.37~7.25 (m, 5H), 7.18 (t, J = 8.4 Hz, 1H), 6.89 (dd, J = 8.4, 2.4 Hz, 1H), 6.26 (s, 1H), 3.95 (t, J = 6.0 Hz, 2H), 2.51 (s, 3H), 2.60~2.36 (m, 6H), 1.74-1.40 (m, 6H). |
| 85 | ¹H NMR (300 MHz, CDCl$_3$): δ 7.75 (d, J = 8.7 Hz, 1H), 7.59 (d, J = 8.7 Hz, 1H), 7.50-7.47 (m, 2H), 7.38-7.32 (m, 5H), 7.19 (t, J = 8.4 Hz, 1H), 6.98 (dd, J = 8.4, 2.7 Hz, 1H), 6.26 (d, J = 1.2 Hz, 1H), 3.93 (s, 2H), 2.69-2.55 (m, 6H), 2.51 (s, 3H), 1.79-1.50 (m, 12H). |
| 86 | ¹H NMR (300 MHz, CDCl$_3$): δ 7.62 (d, J = 9 Hz, 1H), 7.50~7.21 (m, 9H), 7.11 (dd, J = 8.4, 2.1 Hz, 1H), 6.26 (s, 1H), 4.47 (t, J = 4.2 Hz, 2H), 3.43 (t, J = 4.2 Hz, 2H), 2.91 (s, 6H), 2.51 (s, 3H). |
| 87 | ¹H NMR (300 MHz, CDCl$_3$): δ 7.75 (d, J = 9.0 Hz, 1H), 7.59 (d, J = 9.0 Hz, 1H), 7.50-7.45 (m, 2H), 7.37-7.24 (m, 5H), 7.18 (t, J = 8.1 Hz, 1H), 6.99 (ddd, J = 8.4, 2.7, 0.9 Hz, 1H), 6.27 (d, J = 1.2 Hz, 1H), 3.96 (t, J = 6.6 Hz, 2H), 2.52 (d, J = 1.2 Hz, 3H), 2.50 (t, J = 7.8 Hz, 2H), 2.30 (s, 6H), 1.97 (quin, J = 7.8 Hz, 2H). |
| 88 | ¹H NMR (300 MHz, CDCl$_3$): δ 7.75 (d, J = 8.7 Hz, 1H), 7.59 (d, J = 8.7 Hz, 1H), 7.49-7.47 (m, 2H), 7.38-7.32 (m, 5H), 6.99 (t, J = 8.7 Hz, 1H), 6.26 (s, 1H), 3.93 (t, J = 6.0 Hz, 2H), 2.51 (s, 3H), 2.45 (t, J = 7.2 Hz, 2H), 2.33 (s, 6H), 1.85-1.71 (m, 4H). |
| 89 | ¹H NMR (300 MHz, CDCl$_3$): δ 7.74 (d, J = 9.0 Hz, 1H), 7.53 (d, J = 9.0 Hz, 1H), 7.49-7.28 (m, 7H), 7.19 (t, J = 7.5 Hz, 1H), 7.00 (dd, J = 7.5, 2.7 Hz, 1H), 6.26 (d, J = 1.2 Hz, 1H), 4.05 (t, J = 5.7 Hz, 2H), 2.81 (t, J = 5.7 Hz, 2H), 2.66 (bs, 4H), 2.57 (bs, 4H), 2.51 (d, J = 1.2 Hz, 3H), 2.35 (s, 3H). |
| 90 | ¹H NMR (300 MHz, CDCl$_3$): δ 7.75 (d, J = 8.7 Hz, 1H), 7.59 (d, J = 8.7 Hz, 1H), 7.50~7.47 (m, 2H), 7.38-7.32 (m, 4H), 7.27 (dd, J = 6.9, 2.4 Hz, 1H), 7.18 (t, J = 8.4 Hz, 1H), 6.99 (dd, J = 8.1, 2.4 Hz, 1H), 6.26 (d, J = 1.2 Hz, 1H), 3.96 (t, J = 6.6 Hz, 2H), 2.51 (s, 3H), 2.53-2.33 (m, 10H), 2.92 (s, 3H), 1.95 (quin, J = 7.5 Hz, 2H). |
| 91 | ¹H NMR (300 MHz, CDCl$_3$): δ 7.74 (d, J = 8.7 Hz, 1H), 7.58 (d, J = 8.7 Hz, 1H), 7.49-7.45 (m, 2H), 7.37-7.27 (m, 5H), 7.18 (t, J = 8.4 Hz, 1H), 6.27 (ddd, J = 8.4, 2.4, 0.6 Hz, 1H), 6.26 (d, J = 1.2 Hz, 1H), 3.89 (t, J = 6.6 Hz, 2H), 2.50 (d, J = 1.2 Hz, 3H), 2.60-2.38 (m, 10H), 2.30 (d, J = 1.2 Hz, 3H), 1.75 (quin, J = 6.6 Hz, 4H). |
| 92 | ¹H NMR (300 MHz, CDCl$_3$): δ 7.74 (d, J = 8.7 Hz, 1H), 7.62-7.56 (m, 4H), 7.50-7.44 (m, 4H), 6.55 (dd, J = 1.8, 1.8 Hz, 1H), 6.25 (d, J = 1.2 Hz, 1H), 2.50 (d, J = 1.2 Hz, 3H). ¹³C NMR (75 MHz, CDCl$_3$): δ 171.2, 170.7, 159.4, 156.2, 152.7, 151.0, 149.9, 147.6, 147.1, 130.4, 129.5, 128.8, 127.8, 124.3, 121.2, 116.5, 115.3, 113.6, 112.4, 108.8, 19.6. |
| 94 | ¹H NMR (400 MHz, CDCl$_3$): δ 7.77-7.72 (m, 1H), 7.61-7.58 (m, 2H), 7.56-7.44 (m, 3H), 7.22-7.21 (m, 1H), 6.26-6.21 (m, 3H), 2.51 (s, 3H), 2.40 (s, 3H). |

TABLE 1-continued

| Cpd# | Analytical Data |
|---|---|
| 95 | ¹H NMR (300 MHz, CDCl₃): δ 8.11-8.10 (m, 1H), 7.76-7.71 (m, 2H), 7.63-7.60 (m, 3H), 7.58-7.26 (m, 3H), 7.16-7.14 (m, 1H), 6.25 (d, J = 1.2 Hz, 1H), 2.50 (d, J = 1.2 Hz, 3H). ¹³C NMR (100 MHz, CDCl₃): δ 175.2, 161.69, 160.37, 155.09, 149.83, 149.60, 142.78, 135.99, 135.26, 134.98, 134.85, 129.59, 129.17, 128.66, 128.55, 126.48, 126.02, 113.56, 113.46, 113.01, 108.77, 107.84, 25.46. |
| 96 | ¹H NMR (400 MHz, CDCl₃): δ 8.30-8.29 (m, 1H), 7.73 (d, J = 8.8 Hz, 1H), 7.63-7.62 (m, 1H), 7.58-7.55 (m, 3H), 7.44-7.42 (m, 3H), 7.27-7.25 (m, 1H), 6.23 (d, J = 1.2 Hz, 1H), 2.48 (s, 3H). ¹³C NMR (100 MHz, CDCl₃): δ 177.3, 159.4, 156.0, 153.0, 152.8, 149.8, 148.2, 140.3, 134.8, 133.3, 130.4, 129.7, 129.2, 128.8, 128.5, 128.2, 127.9, 127.8, 127.2, 126.8, 126.6, 126.5, 126.4, 125.6, 124.2, 116.5, 115.3, 113.5, 113.1, 108.8, 19.5. |
| 97 | ¹H NMR (300 MHz, CDCl₃): δ 7.76 (d, J = 8.7 Hz, 1H), 7.59-7.40 (m, 13H), 6.80 (s, 1H), 6.26 (d, J = 1.2 Hz, 1H), 2.50 (d, J = 1.2 Hz, 3H). |
| 98 | ¹H NMR (300 MHz, CDCl₃): δ 7.89 (d, J = 3.9 Hz, 1H), 7.76 (d, J = 9.0 Hz, 1H), 7.62-7.48 (m, 7H), 7.13 (d, J = 3.9 Hz, 1H), 6.26 (d, J = 0.8 Hz, 1H), 2.51 (d, J = 0.8 Hz, 1H). |
| 100 | ¹H NMR (300 MHz, CDCl₃): δ 7.72 (d, J = 9.0 Hz, 1H), 7.62-7.39 (m, 7H), 6.91 (d, J = 5.1 Hz, 1H), 6.25 (d, J = 1.2 Hz, 1H), 2.49 (s, 3H), 2.50 (s, 3H). |
| 101 | ¹H NMR (300 MHz, CDCl₃): δ 9.67 (brs, 1H), 7.98-7.93 (m, 1H), 7.75-7.72 (m, 1H), 7.65-7.42 (m, 6H), 7.10-7.07 (m, 1H), 6.39-6.36 (m, 1H), 6.24 (s, 1H), 2.50 (s, 3H). |
| 102 | LCMS [M + 1]⁺: 384.1. |
| 105 | ¹H NMR (400 MHz, CDCl₃): δ 8.46-7.32 (m, 8H), 6.26 (d, J = 0.6 Hz, 1H), 2.52 (d, J = 0.9 Hz, 3H). |
| 106 | ¹H NMR (400 MHz, CDCl₃): δ 8.36 (s, 1H), 7.75 (d, J = 8.8 Hz, 1H), 7.64-7.61 (m, 2H), 7.59-7.42 (m, 9H), 6.26 (d, J = 1.2 Hz, 1H), 2.59 (s, 3H), 2.51 (d, J = 0.8 Hz, 3H). |
| 107 | ¹H NMR (400 MHz, CDCl₃): δ 7.94 (d, J = 2.1 Hz, 1H), 7.78-7.42 (m, 8H), 6.26 (d, J = 0.6 Hz, 1H), 2.51 (d, J = 0.6 Hz, 3H). |
| 109 | ¹H NMR (300 MHz, CDCl₃): δ 7.69 (d, J = 9.0 Hz, 1H), 7.54-7.46 (m, 6H), 6.21 (d, J = 0.9 Hz, 1H), 2.48 (d, J = 1.2 Hz, 3H), 2.11 (s, 8H), 1.80 (s, 7H). ¹³C NMR (75 MHz, CDCl₃): δ 197.2, 159.8, 155.5, 153.0, 150.0, 148.7, 130.6, 130.2, 128.8, 128.0, 124.0, 116.7, 115.4, 113.8, 108.9, 47.3, 37.8, 36.9, 28.3, 19.8. |
| 110 | ¹H NMR (300 MHz, CDCl₃): δ 7.84-7.49 (m, 8H), 6.27 (d, J = 0.6 Hz, 1H), 4.50 (q, J = 7.2 Hz, 2H), 2.51 (d, J = 0.6 Hz, 3H), 1.26 (t, J = 7.2 Hz, 3H). ¹³C NMR (75 MHz, CDCl₃): δ 169.1, 165.9, 159.1, 159.0, 156.7, 156.6, 152.6, 150.2, 145.8, 132.4, 130.3, 129.6, 128.6, 128.0, 125.8, 116.6, 115.7, 114.0, 110.4, 109.0, 62.7, 29.7, 19.5, 14.1. |
| 111 | ¹H NMR (600 MHz, CDCl₃): δ 7.80-7.79 (m, 2H), 7.63-7.59 (m, 2H), 7.48-7.43 (m, 8H), 7.33 (s, 1H), 6.25 (s, 1H), 2.49 (s, 3H). ¹³C NMR (150 MHz, CDCl₃): δ 170.2 (C), 165.4 (C), 162.8 (C), 159.3 (C), 156.6 (C), 152.8 (C), 150.1 (C), 146.3 (C), 131.8 (C), 130.6 (CH), 130.3 (CH × 2), 129.5 (CH), 129.1 (CH × 2), 128.9 (C), 128.0 (CH × 2), 126.9 (CH × 2, C), 125.5 (CH), 116.6 (C), 115.6 (C), 113.9 (CH), 109.1 (CH), 108.2 (CH), 19.6 (CH₃). EIMS m/z (relative intensity): 447 (M⁺, 56), 176 (93), 148 (100), 91 (31), 84 (53), 77 (46), 71 (22), 57 (38), 51 (43). HRMS Calcd. for C₂₈H₁₇NO₅ 447.1107, found 447.1106. IR (neat): 2917, 2849, 1736, 1657, 1649, 1599, 1572, 1552, 1492, 1468, 1421, 1352, 1288, 1250, 1228, 1204, 1167, 1080, 1052 cm⁻¹. |
| 112 | ¹H NMR (300 MHz, CDCl₃): δ 7.81 (d, J = 8.7 Hz, 1H), 7.75 (d, J = 8.4 Hz, 2H), 7.64-7.60 (m, 3H), 7.52-7.45 (m, 5H), 7.31 (s, 1H), 7.27 (s, J = 0.9 Hz, 1H), 2.59 (s, 3H). ¹³C NMR (100 MHz, CDCl₃): δ 183.3, 159.2, 156.7, 152.7, 150.2, 147.7, 137.2, 135.8, 132.7, 130.6, 130.6, 130.2, 129.6, 128.82, 128.80, 127.6, 126.8, 125.2, 116.6, 115.4, 113.6, 109.0, 19.5. |
| 113 | ¹H NMR (400 MHz, CDCl₃): δ 7.89 (d, J = 2.0 Hz, 1H), 7.80 (d, J = 8.4 Hz, 1H), 7.66-7.59 (m, 4H), 7.56 (d, J = 8.4 Hz, 1H), 7.49-7.46 (m, 3H), 7.27 (s, 1H), 6.26 (s, 1H), 2.50 (s, 3H). ¹³C NMR (100 MHz, CDCl₃): δ 169.8 (C), 165.8 (C), 160.9 (C), 159.1 (C), 156.6 (C), 152.6 (C), 150.2 (C), 146.2 (C), 134.9 (C), 133.5 (C), 132.0 (C), 131.2 (CH), 130.3 (CH × 2), 129.6 (CH), 128.8 (C), 128.7 (C), 128.0 (CH × 2), 127.9 (C), 126.0 (CH), 125.6 (CH), 116.5 (C), 115.7 (C), 113.9 (CH), 109.0 (CH), 107.7 (CH), 19.5 (CH₃). EIMS m/z (relative intensity): 519 (9), 517 (37), 515 (M⁺, 52), 269 (34), 195 (52), 176 (54), 148 (62), 86 (61), 84 (100), 75 (53). HRMS Calcd. for C₂₈H₁₅Cl₂NO₅ 515.0237, found 515.0329. IR (neat): 1736, 1657, 1602, 1555, 1493, 1468, 1425, 1363, 1287, 1173, 1080, 1031 cm⁻¹. |
| 114 | ¹H NMR (600 MHz, CDCl₃): δ 7.79 (d, J = 8.9 Hz, 1H), 7.67 (d, J = 8.4 Hz, 1H), 7.60-7.58 (m, 3H), 7.53-7.52 (m, 2H), 7.48-7.46 (m, 3H), 7.36 (dd, J = 1.8, 3.0 Hz, 1H), 6.25 (s, 1H), 2.49 (s, 3H). ¹³C NMR (150 MHz, CDCl₃): δ 170.1 (C), 165.0 (C), 160.5 (C), 159.1 (C), 156.6 (C), 152.6 (C), 146.2 (C), 150.2 (C), 137.0 (C), 133.6 (C), 132.0 (C), 131.8 (CH), 130.4 (CH), 130.3 (CH × 2), 129.5 (CH), 128.8 (C), 128.0 (CH × 2), 127.8 (C), 125.5 (CH), 116.6 (CH), 115.6 (C), 113.9 (CH), 111.1 (CH), 109.0 (CH), 19.6 (CH₃). EIMS m/z (relative intensity): 515 (73), 195 (91), 117 (78), 85 (48), 71 (70), 57 (100). HRMS Calcd. for C₂₈H₁₅Cl₂NO₅ 515.0327, found 515.0328. IR (neat): 2923, 2851, 1736, 1656, 1603, 1569, 1551, 1493, 1437, 1384, 1355, 1288, 1230, 1208, 1171, 1080, 1029 cm⁻¹. |
| 115 | ¹H NMR (300 MHz, CDCl₃): δ 8.25-8.24 (m, 1H), 7.80-7.77 (m, 1H), 7.74-7.67 (m, 2H), 7.58 (d, J = 9.0 Hz, 1H), 7.42-7.38 (m, 2H), 7.25-7.20 (m, 4H), 6.24 (d, J = 1.2 Hz, 1H), 2.49 (d, J = 1.2 Hz, 3H). |

TABLE 1-continued

| Cpd# | Analytical Data |
|---|---|
| 116 | $^1$H NMR (400 MHz, CDCl$_3$): δ 9.00 (s, 1H), 6.65 (d, J = 4.0 Hz, 1H), 8.05-8.02 (m, 1H), 7.77 (d, J = 9.0 Hz, 1H), 7.59 (d, J = 9.0 Hz, 1H), 7.49-7.47 (m, 2H), 7.37-7.34 (m, 3H), 7.27-7.23 (m, 1H), 6.26 (q, J = 1.2 Hz, 1H), 2.50 (d, J = 1.2 Hz, 3H). $^{13}$C NMR (100 MHz, CDCl$_3$): δ 183.5 (C), 159.3 (C), 156.6 (C), 152.9 (CH), 152.7 (C), 150.6 (CH), 150.1 (C), 147.5 (C), 136.6 (CH), 132.5 (C), 130.7 (CH × 2), 130.0 (C), 129.2 (C), 129.18 (CH), 128.0 (CH × 2), 124.9 (CH), 123.0 (CH), 116.4 (C), 115.5 (C), 113.8 (CH), 109.0 (CH), 19.5 (CH$_3$). EIMS m/z (relative intensity) 381 (M$^+$, 7), 279 (10), 88 (10), 86 (63), 84 (100), 71 (15), 57 (22), 51 (34). HRMS Calcd. for C$_{24}$H$_{15}$ClO$_4$ 381.1001, found 381.1006. IR (neat): 2924, 2854, 1731, 1650, 1626, 1602, 1585, 1553, 1492, 1471, 1446, 1416, 1380, 1366, 1263, 1178, 1153, 1080, 1063 cm$^{-1}$. |
| 117 | $^1$H NMR (300 MHz, CDCl$_3$): δ 8.62-8.60 (m, 1H), 7.78 (d, J = 9.3 Hz, 1H), 7.59-7.52 (m, 2H), 7.47-7.44 (m, 1H), 7.37-7.27 (m, 2H), 6.25 (d, J = 1.2 Hz, 1H), 2.50 (d, J = 1.2 Hz, 3H). $^{13}$C NMR (75 MHz, CDCl$_3$): δ 184.0, 159.2, 156.5, 152.7, 150.1, 150.0, 147.1, 143.3, 130.6, 130.5, 129.3, 129.0, 127.8, 125.1, 122.3, 116.2, 115.5, 113.7, 108.9, 19.5. |
| 118 | $^1$H NMR (300 MHz, CDCl$_3$): δ 7.86-7.83 (m, 2H), 7.61-7.58 (m, 2H), 7.46-7.41 (m, 2H), 7.26-7.08 (m, H), 6.95 (d, J = 8.7 Hz, 1H), 6.12 (s, 1H), 5.12 (s, 2H), 2.39 (s, 3H). |
| 119 | $^1$H NMR (300 MHz, CDCl$_3$): δ 7.73-7.51 (m, 7H), 6.21 (s, 1H), 2.48 (s, 3H), 2.34 (d, J = 0.8 Hz, 3H). $^{13}$C NMR (75 MHz, CDCl$_3$): δ 188.7, 159.3, 155.9, 152.7, 150.1, 148.2, 130.3, 130.0, 129.2, 128.4, 128.2, 127.9, 124.6, 117.0, 115.2, 113.5, 108.8, 28.5, 19.4. |
| 120 | $^1$H NMR (400 MHz, CDCl$_3$): δ 7.78-7.76 (m 2H), 7.54-7.50 (m, 2H), 7.40-7.36 (m, 2H), 7.22-7.19 (m, 1H), 6.11 (d, J = 1.2 Hz, 1H), 3.66 (s, 3H), 2.35 (d, J = 0.8 Hz, 1H). |
| 121 | $^1$H NMR (300 MHz, CDCl$_3$): δ 7.70 (d, J = 8.7 Hz, 1H), 7.57-7.52 (m, 3H), 7.51-7.47 (m, 3H), 6.22 (d, J = 1.2 Hz, 1H), 4.30 (q, J = 7.1 Hz, 2H), 2.48 (d, J = 1.2 Hz, 3H), 1.22 (t, J = 7.2 Hz, 3H). |
| 122 | $^1$H NMR (300 MHz, CDCl$_3$): δ 7.70 (d, J = 9.0 Hz, 1H), 7.54-7.46 (m, 6H), 6.22 (d, J = 1.2 Hz, 1H), 2.48 (d, J = 1.2 Hz, 3H), 1.40 (s, 9H). |
| 127 | $^1$H NMR (300 MHz, CDCl$_3$): δ 7.71 (d, J = 9.0 Hz, 1H), 7.68-7.42 (m, 6H), 6.22 (d, J = 1.2 Hz, 1H), 3.70 (m, 1H), 2.93-1.07 (m, 10H), 2.59 (s, 3H). |
| 128 | $^1$H NMR (300 MHz, CDCl$_3$): δ 7.65-7.61 (m, 2H), 7.56-7.42 (m, 5H), 6.23 (d, J = 0.9 Hz, 1H), 2.48 (d, J = 0.9 Hz, 3H). |
| 129 | $^1$H NMR (300 MHz, CDCl$_3$): δ 7.62-7.57 (m, 3H), 7.54-7.43 (m, 4H), 2.67 (s, 3H). |
| 130 | $^1$H NMR (300 MHz, CDCl$_3$): δ 7.65-7.61 (m, 3H), 7.56-7.45 (m, 6H), 7.39-7.29 (m, 3H), 6.25 (d, J = 0.9 Hz, 1H), 2.44 (d, J = 1.2 Hz, 3H). LCMS [M + 1]$^+$: 353.1. |
| 131 | $^1$H NMR (300 MHz, CDCl$_3$): δ 7.53-7.36 (m, 7H), 6.17 (d, J = 1.2 Hz, 1H), 2.77 (t, J = 7.5 Hz, 2H), 2.44 (d, J = 0.9 Hz, 3H), 1.79 (h, J = 7.5 Hz, 2H), 0.96 (t, J = 7.5 Hz, 3H). |
| 132 | $^1$H NMR (300 MHz, CDCl$_3$): δ 8.05 (d, J = 7.5 Hz, 2H), 7.56 (d, J = 8.7 Hz, 1H), 7.60-7.39 (m, 6H), 7.06-7.01 (m, 1H), 6.85-6.79 (m, 1H), 6.28 (d, J = 1.2 Hz, 1H), 2.51 (d, J = 1.2 Hz, 3H). |
| 133 | $^1$H NMR (300 MHz, CDCl$_3$): δ 7.81 (d, J = 7.2 Hz, 2H), 7.76 (d, J = 8.7 Hz, 1H), 7.59 (d, J = 8.7 Hz, 1H), 7.50 (dd, J = 7.5, 7.5 Hz, 2H), 7.37 (d, J = 8.1 Hz, 1H), 7.34-7.26 (m, 2H), 7.18 (d, J = 9.9 Hz, 1H), 7.04 (t, J = 8.7 Hz, 1H), 6.27 (s, 1H), 2.51 (s, 3H). |
| 134 | $^1$H NMR (300 MHz, CDCl$_3$): δ 7.80-7.72 (m, 3H), 7.55 (d, J = 9.0 Hz, 1H), 7.52-7.44 (m, 3H), 7.36-7.31 (m, 2H), 7.04-6.99 (m, 2H), 6.25 (d, J = 1.2 Hz, 1H), 2.49 (d, J = 1.2 Hz, 3H). $^{13}$C NMR (75 MHz, CDCl$_3$): δ 185.2, 164.5, 161.2, 159.4, 156.3, 152.9, 149.8, 148.1, 136.4, 133.0, 132.5, 132.4, 129.6, 128.1, 127.6, 125.6, 125.5, 124.3, 115.3, 115.0, 114.7, 113.5, 108.9, 19.5. |
| 135 | $^1$H NMR (400 MHz, CDCl$_3$): δ 7.85 (d, J = 6.8 Hz, 2H), 7.74 (d, J = 8.8 Hz, 1H), 7.59 (d, J = 8.8 Hz, 1H), 7.49 (t, J = 7.6 Hz, 1H), 7.40 (d, J = 7.6 Hz, 1H), 7.38-7.32 (m, 3H), 7.13-7.08 (m, 4H), 6.25 (d, J = 1.2 Hz, 1H), 2.45 (d, J = 1.2 Hz, 3H). |
| 136 | $^1$H NMR (300 MHz, CDCl$_3$): δ 7.83 (d, J = 7.2 Hz, 2H), 7.76 (d, J = 9.0 Hz, 1H), 7.58 (d, J = 9.0 Hz, 1H), 7.56-7.53 (m, 3H), 7.48-7.37 (m, 3H), 6.28 (s, 1H), 2.52 (s, 3H). |
| 137 | $^1$H NMR (300 MHz, CDCl$_3$): δ 7.82-7.78 (m, 2H), 7.75 (d, J = 9.3 Hz, 1H), 7.57 (d, J = 8.7 Hz, 1H), 7.54-7.49 (m, 1H), 7.45-7.42 (m, 2H), 7.38-7.30 (m, 4H), 6.27 (d, J = 1.2 Hz, 1H), 2.51 (d, J = 0.9 Hz, 3H). |
| 138 | $^1$H NMR (300 MHz, CDCl$_3$): δ 7.81-7.74 (m, 3H), 7.59-7.44 (m, 5H), 7.38-7.33 (m, 2H), 7.28-7.22 (m, 1H), 6.27 (d, J = 1.2 Hz, 1H), 2.51 (d, J = 1.2 Hz, 3H). $^{13}$C NMR (75 MHz, CDCl$_3$): δ 185.1, 159.2, 156.3, 152.8, 149.7, 148.3, 136.4, 133.6, 133.1, 131.7, 129.5, 129.23, 129.15, 128.2, 127.1, 124.4, 121.6, 116.0, 115.4, 113.7, 108.9, 19.5. |
| 139 | $^1$H NMR (300 MHz, CDCl$_3$): δ 7.81-7.74 (m, 3H), 7.60-7.44 (m, 5H), 7.38-7.33 (m, 2H), 7.28-7.22 (m, 1H), 6.23 (d, J = 1.2 Hz, 1H), 2.46 (d, J = 1.2 Hz, 3H). $^{13}$C NMR (75 MHz, CDCl$_3$): δ 185.1, 159.2, 156.3, 152.8, 149.7, 148.3, 136.4, 133.6, 133.1, 131.7, 129.5, 129.23, 129.15, 128.2, 127.1, 124.4, 121.6, 116.0, 115.4, 113.7, 108.9, 19.5. |
| 140 | $^1$H NMR (300 MHz, CDCl$_3$): δ 7.81-7.73 (m, 3H), 7.58-7.45 (m, 4H), 7.39-7.26 (m, 4H), 6.27 (s, 1H), 2.50 (s, 3H). $^{13}$C NMR (75 MHz, CDCl$_3$): δ 185.2, 159.4, 156.3, 152.9, 152.8, 149.8, 148.2, 136.5, 133.6, 133.1, 132.2, 131.7, 131.0, 129.7, 129.5, 129.24, 129.17, 128.6, 128.2, 127.5, 124.4, 124.4, 123.2, 121.6, 116.0, 115.4, 113.7, 113.6, 109.0, 19.6. |
| 141 | $^1$H NMR (300 MHz, CDCl$_3$): δ 7.76-7.72 (m, 3H), 7.57 (d, J = 9.0 Hz, 1H), 7.46-7.41 (m, 1H), 7.33-7.20 (m, 5H), 7.10 (d, J = 7.5 Hz, 1H), 6.25 (d, J = 0.9 Hz, 1H), 2.50 (d, J = 0.9 Hz, 3H), 2.25 (s, 3H). |
| 142 | $^1$H NMR (300 MHz, CDCl$_3$): δ 7.78-7.68 (m, 3H), 7.53-7.45 (m, 2H), 7.42-7.27 (m, 4H), 7.13-7.10 (m, 2H), 6.22 (s, 1H), 2.46 (s, 3H), 2.32 (s, 3H). $^{13}$C NMR (75 MHz, CDCl$_3$): δ 185.4, 159.5, 156.3, 152.9, 149.8, 147.9, 138.4, 136.5, 132.7, 130.5, 129.6, 128.7, 128.4, 128.0, 127.8, 126.4, 124.1, 116.2, 115.2, 113.3, 108.8, 21.3, 19.4. |

TABLE 1-continued

| Cpd# | Analytical Data |
|---|---|
| 143 | $^1$H NMR (300 MHz, CDCl$_3$): δ 7.88-7.76 (m, 5H), 7.75-7.51 (m, 4H), 7.43-7.38 (m, 2H), 6.27 (d, J = 1.2 Hz, 1H), 2.51 (d, J = 1.2 Hz, 3H). $^{13}$C NMR (75 MHz, CDCl$_3$): δ 184.6, 159.0, 156.1, 152.7, 149.6, 148.5, 136.3, 134.8, 134.1, 133.3, 132.2, 131.3, 129.7, 128.7, 128.4, 126.3, 124.7, 118.4, 115.9, 115.6, 113.8, 112.1, 109.0, 19.5. |
| 144 | $^1$H NMR (300 MHz, CDCl$_3$): δ 8.25-7.61 (m, 11H), 6.21 (s, 1H), 2.51 (d, J = 1.2 Hz, 3H). LCMS [M + 1]$^+$: 426.0. |
| 145 | $^1$H NMR (300 MHz, CDCl$_3$): δ 8.27-8.24 (m, 2H), 7.90-7.80 (m, 2H), 7.77-7.70 (m, 3H), 7.70-7.53 (m, 2H), 7.44-7.27 (m, 2H), 6.28 (d, J = 0.9 Hz, 1H), 2.52 (d, J = 0.9 Hz, 3H). $^{13}$C NMR (75 MHz, CDCl$_3$): δ 184.6, 159.1, 156.2, 152.8, 147.9, 136.9, 136.3, 133.5, 131.5, 130.2, 129.8, 129.5, 128.4, 128.2, 126.4, 124.7, 123.0, 115.7, 113.9, 109.1, 19.5. |
| 146 | $^1$H NMR (300 MHz, CDCl$_3$): δ 7.75-7.30 (m, 11H), 6.21 (s, 1H), 3.82 (s, 2H), 2.33 (s, 3H). |
| 147 | $^1$H NMR (300 MHz, CDCl$_3$): δ 7.89-7.21 (m, 14H), 6.22 (s, 1H), 2.47 (s, 3H). |
| 148 | $^1$H NMR (400 MHz, CDCl$_3$): δ 7.85 (d, J = 7.2 Hz, 2H), 7.74 (d, J = 8.8 Hz, 1H), 7.59 (d, J = 8.7 Hz, 1H), 7.47 (t, J = 7.2 Hz, 1H), 7.40-7.33 (m, 4H), 7.13-7.12 (m, 2H), 6.25 (d, J = 1.2 Hz, 1H), 2.50 (s, 3H). |
| 149 | $^1$H NMR (300 MHz, CDCl$_3$): δ 7.85 (dd, J = 8.7, 1.8 Hz, 2H), 7.58 (d, J = 8.7 Hz, 2H), 7.62 (d, J = 8.7 Hz, 1H), 7.54 (d, J = 7.5 Hz, 1H), 7.43 (d, J = 7.5 Hz, 1H), 7.39 (d, J = 1.8 Hz, 2H), 7.35 (dd, J = 1.8, 1.8 Hz, 1H), 6.28 (d, J = 1.2 Hz, 1H), 2.51 (d, J = 1.2 Hz, 3H). |
| 150 | $^1$H NMR (300 MHz, CDCl$_3$): δ 7.84 (d, J = 6.9 Hz, 2H), 7.76 (d, J = 9.0 Hz, 1H), 7.64 (t, J = 1.8 Hz, 1H), 7.59-7.53 (m, 4H), 7.43 (t, J = 6.0 Hz, 2H), 6.29 (d, J = 1.5 Hz, 1H), 2.52 (d, J = 1.5 Hz, 3H). LCMS [M + 1]$^+$: 539.9. |
| 151 | $^1$H NMR (300 MHz, CDCl$_3$): δ 9.13 (t, J = 2.1 Hz, 1H), 8.81 (t, J = 2.1 Hz, 2H), 7.92 (dd, J = 8.4, 1.5 Hz, 2H), 7.83 (d, J = 9.0 Hz, 1H), 7.65-7.61 (m, 2H), 7.50 (t, J = 7.2 Hz, 2H), 6.28 (d, J = 0.9 Hz, 1H), 2.51 (d, J = 0.9 Hz, 3H). |
| 153 | $^1$H NMR (300 MHz, CDCl$_3$): δ 8.05-8.01 (m, 2H), 7.83 (s, 1H), 7.83-7.68 (m, 2H), 7.66-7.28 (m, 3H), 6.32 (d, J = 0.9 Hz, 1H), 2.53 (s, 3H). $^{13}$C NMR (75 MHz, CDCl$_3$): 183.7, 160.1, 157.6, 153.3, 152.6, 149.0, 136.6, 133.3, 129.3, 128.7, 124.5, 117.0, 115.1, 113.6, 113.4, 109.1, 22.6. |
| 154 | $^1$H NMR (300 MHz, CDCl$_3$): δ 8.06-8.03 (m, 2H), 7.67 (d, J = 8.7 Hz, 1H), 7.64-7.60 (m, 1H), 7.56-7.51 (m, 3H), 7.45 (d, J = 8.7 Hz, 1H), 6.29 (d, J = 1.2 Hz, 1H), 2.91 (s, 3H), 2.51 (d, J = 0.9 Hz, 3H). |
| 155 | $^1$H NMR (300 MHz, CDCl$_3$): δ 8.06-7.44 (m, 7H), 6.32 (d, J = 1.2 Hz, 1H), 3.37 (t, J = 5.4 Hz, 2H), 2.52 (d, J = 1.2 Hz, 3H), 2.52 (d, J = 1.2 Hz, 3H), 1.87 (sex, J = 7.2 Hz, 2H), 1.07 (t, J = 7.2 Hz, 3H). |
| 156 | $^1$H NMR (300 MHz, CDCl$_3$): δ 8.07-8.03 (m, 2H), 7.69-7.43 (m, 5H), 6.30 (s, 1H), 2.57 (d, J = 1.2 Hz, 3H), 1.83-1.34 (m, 8H), 0.89 (t, J = 7.2 Hz, 3H). $^{13}$C NMR (75 MHz, CDCl$_3$): δ 185.4, 159.9, 159.8, 156.2, 153.1, 153.0, 150.2, 148.5, 148.3, 137.6, 132.8, 132.2, 131.8, 129.6, 128.6, 128.3, 128.1, 124.0, 117.43, 117.35, 114.9, 113.2, 108.8, 39.3. 31.6, 29.9, 28.4, 25.1, 23.3, 22.4, 19.5, 14.0. |
| 157 | $^1$H NMR (300 MHz, CDCl$_3$): δ 8.06-7.52 (m, 7H), 6.31 (d, J = 1.2 Hz, 1H), 3.38 (t, J = 7.5 Hz, 2H), 2.52 (d, J = 1.2 Hz, 3H), 1.80 (quin, J = 7.8 Hz, 2H), 1.62-1.26 (m, 6H), 0.87 (t, J = 6.9 Hz, 3H). |
| 158 | $^1$H NMR (300 MHz, CDCl$_3$): δ 8.06-7.44 (m, 7H), 6.31 (s, 1H), 3.38 (t, J = 7.5 Hz, 2H), 2.51 (s, 3H), 1.80 (quin, J = 7.5 Hz, 2H), 1.63 (bs, 2H), 1.48 (quin, J = 7.2 Hz, 2H), 1.43 (bs, 10H), 0.86 (t, J = 6.3 Hz, 3H). |
| 159 | $^1$H NMR (300 MHz, CDCl$_3$): δ 7.84-7.24 (m, 9H), 6.48-6.46 (m, 1H), 6.28 (s, 1H), 2.49 (s, 3H). $^{13}$C NMR (75 MHz, CDCl$_3$): δ 185.5, 159.6, 156.4, 153.0, 149.3, 148.0, 143.3, 142.8, 136.8, 133.0, 129.2, 128.3, 124.1, 116.9, 115.4, 114.6, 114.4, 113.3, 111.9, 108.9, 19.5. |
| 160 | $^1$H NMR (300 MHz, CDCl$_3$): δ 7.83-7.29 (m, 10H), 6.26 (d, J = 0.6 Hz, 1H), 2.48 (d, J = 0.6 Hz, 3H). $^{13}$C NMR (75 MHz, CDCl$_3$): δ 185.2, 159.5, 156.2, 152.9, 149.7, 148.5, 136.4, 133.1, 131.3, 129.5, 129.2, 128.3, 128.2, 126.8, 124.3, 120.9, 116.0, 115.4, 113.5, 108.9, 19.5. |
| 161 | $^1$H NMR (300 MHz, CDCl$_3$): δ 8.17-7.95 (m, 4H), 7.77-7.30 (m, 10H), 6.37 (s, 1H), 2.55 (s, 3H). |
| 165 | $^1$H NMR (400 MHz, CDCl$_3$): δ 7.95-7.93 (m, 2H), 7.67 (d, J = 8.8 Hz, 1H), 7.64-7.60 (m, 1H), 7.53-7.49 (m, 2H), 7.43 (d, J = 8.8 Hz, 1H), 6.30 (q, J = 1.2 Hz, 1H), 3.68 (tt, J = 3.6, 12.4 Hz, 1H), 2.50 (d, J = 1.2 Hz, 3H), 2.34-2.23 (m, 2H), 1.89-1.85 (m, 2H), 1.74-1.71 (m, 3H), 1.65-1.42 (m, 1H), 1.42-1.33 (m, 2H). $^{13}$C NMR (100 MHz, CDCl$_3$): δ 186.5 (C), 159.8 (C), 156.8 (C), 153.1 (C), 149.4 (C), 148.1 (C), 137.9 (C), 135.0 (C), 133.1 (CH), 129.7 (CH × 2), 128.4 (CH × 2), 123.8 (CH), 117.1 (C), 115.1 (C), 113.0 (CH), 108.9 (CH), 35.1 (CH), 30.6 (CH$_2$ × 2), 26.7 (CH$_2$ × 2), 25.5 (CH$_2$), 19.7 (CH$_3$). EIMS m/z (relative intensity) 386 (M$^+$, 54), 329 (24), 317 (100), 203 (28), 105 (55), 78 (62), 63 (90), 57 (63). HRMS Calcd. for C$_{25}$H$_{12}$O$_4$ 386.1518, found 386.1518. IR (neat): 3058, 2923, 2852, 1738, 1636, 1599, 1538, 1468, 1447 cm$^{-1}$. |
| 166 | $^1$H NMR (600 MHz, CDCl$_3$): δ 7.75 (d, J = 8.0 Hz, 1H), 7.72 (d, J = 8.8 Hz, 1H), 7.56 (d, J = 8.8 Hz, 1H), 7.46-7.39 (m, 3H), 7.34-7.14 (m, 6H), 6.23 (s, 1H), 2.48 (s, 3H). $^{13}$C NMR (100 MHz, CDCl$_3$): δ 220.0 (C), 159.4 (C), 157.4 (C), 154.8 (C), 152.8 (C), 150.4 (C), 145.4 (C), 131.8 (CH), 130.8 (CH), 130.3 (C), 129.0 (CH × 2), 128.3 (CH), 127.6 (CH × 3), 124.7 (CH), 124.3 (CH), 117.2 (CH), 115.4 (C), 113.4 (CH), 108.8 (CH), 19.5 (CH$_3$). EIMS m/z (relative intensity) 396 (M$^+$, 60), 378 (100), 367 (26), 189 (10), 105 (32), 83 (75), 77 (20). HRMS Calcd. for C$_{25}$H$_{16}$O$_3$S 396.082, found 396.0823. IR (neat): 2918, 2851, 1735, 1647, 1600, 1541, 1488, 1443, 1381, 1356, 1155, 1078 cm$^{-1}$. |

TABLE 1-continued

| Cpd# | Analytical Data |
|---|---|
| 170 | ¹H NMR (300 MHz, CDCl$_3$): δ 7.60-7.55 (m, 2H), 7.52-7.44 (m, 6H), 7.43-7.29 (m, 4H), 6.18 (d, J = 1.2 Hz, 1H), 5.97 (s, 1H), 2.76 (s, 1H), 2.44 (d, J = 0.9 Hz, 3H). |
| 171 | LCMS [M + 1]$^+$: 396.1 |
| 172 | ¹H NMR (300 MHz, CDCl$_3$): δ 7.58-7.54 (m, 2H), 7.52-7.44 (m, 6H), 7.42-7.28 (m, 4H), 6.18 (d, J = 1.2 Hz, 1H), 5.96 (d, J = 5.4 Hz, 1H), 2.76 (d, J = 5.4 Hz, 1H), 2.44 (d, J = 1.2 Hz, 3H). LCMS [M + 1]$^+$: 383.0. |
| 173 | ¹H NMR (300 MHz, CDCl$_3$): δ 7.57-7.23 (m, 12H), 6.19 (d, J = 0.9 Hz, 1H), 4.15 (s, 2H), 2.25 (d, J = 0.9 Hz, 3H). LCMS [M + 1]$^+$: 367.1. |
| 174 | LCMS [M + 1]$^+$: 438.1 |
| 175 | LCMS [M + 1]$^+$: 486.1 |
| 176 | LCMS [M + 1]$^+$: 410.1 |
| 177 | ¹H NMR (300 MHz, CD$_3$OD): δ 7.82 (d, J = 8.7 Hz, 1H), 7.55 (d, J = 8.7 Hz, 1H), 7.41-7.01 (m, 9H), 6.21 (d, J = 1.2 Hz, 1H), 4.06-3.54 (m, 12H), 2.47 (d, J = 0.9 Hz, 3H). |
| 178 | ¹H NMR (300 MHz, CD$_3$OD): δ 7.91 (d, J = 8.7 Hz, 1H), 7.63 (d, J = 9.0 Hz, 1H), 7.46-7.03 (m, 9H), 6.27 (d, J = 1.2 Hz, 1H), 4.09-3.58 (m, 16H), 2.52 (d, J = 1.2 Hz, 3H). |
| 179 | ¹H NMR (400 MHz, CDCl$_3$): δ 7.74 (d, J = 8.8 Hz, 1H), 7.58 (d, J = 8.8 Hz, 1H), 7.49-7.32 (m, 7H), 7.19 (t, J = 8.0 Hz, 1H), 7.00 (dd, J = 8.0, 2.4 Hz, 1H), 6.26 (d, J = 1.2 Hz, 1H), 3.74 (d, J = 5.8 Hz, 2H), 2.51 (d, J = 1.2 Hz, 3H), 1.25 (bs, 1H), 0.65 (q, J = 5.8 Hz, 2H), 0.34 (q, J = 4.8 Hz, 2H). |
| 180 | ¹H NMR (300 MHz, CDCl$_3$): δ 7.75 (d, J = 8.7 Hz, 1H), 7.64 (dt, J = 8.1, 1.2 Hz, 1H), 7.58 (d, J = 8.7 Hz, 1H), 7.56-7.18 (m, 8H), 6.26 (d, J = 1.2 Hz, 1H), 2.51 (d, J = 1.2 Hz, 3H), 2.30 (s, 3H). |
| 181 | ¹H NMR (300 MHz, CDCl$_3$): δ 7.75 (d, J = 9.0 Hz, 1H), 7.59 (d, J = 9.0 Hz, 1H), 7.63-7.19 (m, 9H), 6.26 (s, 1H), 2.51 (s, 3H), 1.83-1.79 (m, 1H), 1.19-1.10 (m, 2H), 1.09-1.00 (m, 2H). |
| 182 | ¹H NMR (300 MHz, CDCl$_3$): δ 7.75 (d, J = 9.0 Hz, 1H), 7.64 (dt, J = 7.8, 1.5 Hz, 1H), 7.60-7.23 (m, 9H), 6.66 (dd, J = 17.4, 1.5 Hz, 1H), 6.26 (d, J = 1.2 Hz, 1H), 6.04 (dd, J = 10.5, 1.2 Hz, 1H), 2.51 (d, J = 1.2 Hz, 3H). |
| 183 | ¹H NMR (300 MHz, CDCl$_3$): δ 7.73 (d, J = 9.0 Hz, 1H), 7.58 (d, J = 9.0 Hz, 1H), 7.45-7.29 (m, 7H), 7.00 (ddd, J = 8.4, 2.4, 0.9 Hz, 1H), 6.25 (d, J = 1.2 Hz, 1H), 4.08 (t, J = 5.4 Hz, 2H), 3.03 (t, J = 5.4 Hz, 2H), 2.50 (d, J = 1.2 Hz, 3H), 2.02-1.25 (m, 14H). |
| 184 | ¹H NMR (300 MHz, CDCl$_3$): δ 7.74 (d, J = 9.0 Hz, 1H), 7.58 (d, J = 8.7 Hz, 1H), 7.49-7.00 (m, 9H), 6.26 (s, 1H), 4.04 (t, J = 4.5 Hz, 2H), 3.94 (t, J = 3.9 Hz, 2H), 2.50 (s, 3H). |
| 185 | ¹H NMR (300 MHz, CDCl$_3$): δ 7.73 (d, J = 8.7 Hz, 1H), 7.58 (d, J = 8.7 Hz, 1H), 7.49-6.97 (m, 9H), 6.25 (d, J = 1.2 Hz, 1H), 4.06 (t, J = 6.0 Hz, 2H), 3.85 (t, J = 6.0 Hz, 2H), 2.50 (d, J = 1.2 Hz, 3H), 2.06-1.98 (m, 2H). |
| 186 | ¹H NMR (300 MHz, CDCl$_3$): δ 7.73 (d, J = 9.0 Hz, 1H), 7.58 (d, J = 9.0 Hz, 1H), 7.50-6.96 (m, 9H), 6.25 (d, J = 0.9 Hz, 1H), 3.93 (t, J = 6.0 Hz, 2H), 3.47 (m, 2H), 2.50 (s, 3H), 2.10-1.64 (m, 4H). |
| 187 | ¹H NMR (300 MHz, CDCl$_3$): δ 7.74 (d, J = 9.0 Hz, 1H), 7.58 (d, J = 9.0 Hz, 1H), 7.51-6.96 (m, 9H), 6.26 (d, J = 1.2 Hz, 1H), 3.91 (t, J = 6.3 Hz, 2H), 3.44 (t, J = 6.3 Hz, 2H), 2.51 (d, J = 0.6 Hz, 3H), 1.98-1.56 (m, 6H). |
| 188 | ¹H NMR (300 MHz, CD$_3$OD): δ 7.88 (d, J = 9.0 Hz, 1H), 7.60 (d, J = 9.0 Hz, 1H), 7.44-6.98 (m, 9H), 6.25 (d, J = 1.2 Hz, 1H), 3.89 (t, J = 6.3 Hz, 2H), 3.56 (t, J = 6.6 Hz, 2H), 2.50 (d, J = 1.2 Hz, 3H), 1.78-1.42 (m, 8H). |
| 189 | ¹H NMR (400 MHz, CDCl$_3$): δ 7.73 (d, J = 6.6 Hz, 1H), 7.57 (d, J = 6.6 Hz, 1H), 7.49-6.99 (m, 9H), 6.25 (d, J = 0.9 Hz, 1H), 3.99-3.93 (m, 4H), 2.50 (d, J = 0.9 Hz, 3H), 0.90 (s, 9H), 0.09 (s, 6H). |
| 190 | ¹H NMR (300 MHz, CDCl$_3$): δ 7.74 (d, J = 9.0 Hz, 1H), 7.58 (d, J = 9.0 Hz, 1H), 7.50-6.97 (m, 9H), 6.26 (d, J = 1.2 Hz, 1H), 4.02 (t, J = 6.3 Hz, 2H), 3.78 (t, J = 6.0 Hz, 2H), 2.51 (d, J = 1.2 Hz, 3H), 1.96 (t, J = 6.0 Hz, 2H), 0.88 (s, 9H), 0.042 (s, 6H). |
| 191 | ¹H NMR (300 MHz, CDCl$_3$): δ 7.73 (d, J = 9.0 Hz, 1H), 7.57 (d, J = 9.0 Hz, 1H), 7.50-6.96 (m, 9H), 6.25 (d, J = 1.2 Hz, 1H), 3.93 (t, J = 6.3 Hz, 2H), 3.68 (t, J = 6.3 Hz, 2H), 2.50 (d, J = 0.9 Hz, 3H), 1.85-1.65 (m, 4H), 0.90 (s, 9H), 0.05 (s, 6H). |
| 193 | ¹H NMR (300 MHz, CDCl$_3$): δ 7.74 (d, J = 9.0 Hz, 1H), 7.58 (d, J = 9.0 Hz, 1H), 7.50-6.96 (m, 9H), 6.26 (d, J = 1.2 Hz, 1H), 3.90 (t, J = 6.3 Hz, 2H), 3.62 (t, J = 6.6 Hz, 2H), 2.51 (d, J = 1.2 Hz, 3H), 1.79-1.39 (m, 8H), 0.89 (s, 9H), 0.05 (s, 6H). |
| 194 | LCMS [M + 1]$^+$: 771.2. |
| 195 | ¹H NMR (400 MHz, CDCl$_3$): δ 7.93 (brs, 2H), 7.64 (brs, 1H), 7.44 (brs, 2H), 7.28 (brs, 5H), 7.05 (brs, 1H), 6.26 (brs, 1H), 4.42-3.45 (m, 11H), 2.53 (brs, 3H). |
| 196 | ¹H NMR (300 MHz, CDCl$_3$): δ 7.72 (d, J = 8.7 Hz, 1H), 7.57-7.54 (m, 1H), 7.48-7.45 (m, 2H), 7.36-7.31 (m, 5H), 7.19-7.13 (m, 1H), 6.99-6.95 (m, 1H), 6.22 (s, 1H), 5.42-5.30 (m, 2H), 5.21-4.94 (m, 3H), 4.47-4.43 (m, 1H), 4.12-3.43 (m, 7H), 2.16 (s, 3H). |
| 197 | ¹H NMR (300 MHz, CDCl$_3$): δ 7.95 (d, J = 9.0 Hz, 1H), 7.67 (d, J = 9.0 Hz, 1H), 7.47-7.45 (m, 2H), 7.33-7.19 (m, 6H), 7.05-7.03 (m, 1H), 6.29 (s, 1H), 4.26-4.22 (m, 1H), 4.09-3.46 (m, 16H), 2.55 (s, 3H). |
| 198 | ¹H NMR (300 MHz, CDCl$_3$): δ 7.86 (d, J = 15.9 Hz, 1H), 7.73 (d, J = 9.0 Hz, 1H), 7.67-7.30 (m, 15H), 6.61 (d, J = 15.9 Hz, 1H), 6.24 (d, J = 1.2 Hz, 1H), 2.48 (d, J = 1.2 Hz, 3H). |
| 199 | ¹H NMR (300 MHz, CDCl$_3$): δ 7.76 (d, J = 9.0 Hz, 1H), 7.62 (d, J = 9.0 Hz, 1H), 7.50-7.21 (m, 8H), 7.11 (dd, J = 8.4, 2.1 Hz, 1H), 6.26 (s, 1H), 4.47 (t, J = 4.2 Hz, 2H), 3.43 (t, J = 4.2 Hz, 2H), 2.91 (s, 6H), 2.51 (s, 3H). |

TABLE 1-continued

| Cpd# | Analytical Data |
|---|---|
| 200 | $^1$H NMR (300 MHz, CDCl$_3$): δ 7.73 (d, J = 9.0 Hz, 1H), 7.57 (d, J = 9.0 Hz, 1H), 7.49-6.96 (m, 14H), 6.25 (d, J = 1.2 Hz, 1H), 4.03 (t, J = 6.0 Hz, 2H), 2.95 (m, 2H), 2.74 (t, J = 6.0 Hz, 2H), 2.54-2.50 (m, 5H), 2.07-1.99 (m, 3H), 1.67-1.63 (m, 2H), 1.40-1.26 (m, 2H). |
| 201 | $^1$H NMR (300 MHz, CDCl$_3$): δ 7.78-7.32 (m, 16H), 6.26 (d, J = 1.2 Hz, 1H), 2.39 (d, J = 1.2 Hz, 3H). |
| 202 | $^1$H NMR (300 MHz, CDCl$_3$): δ 7.75 (d, J = 8.7 Hz, 1H), 7.66-7.19 (m, 10H), 6.26 (d, J = 1.2 Hz, 1H), 2.63 (dt, J = 7.2, 2.7 Hz, 2H), 2.59 (d, J = 1.2 Hz, 3H), 2.05~2.04 (m, 1H), 2.81 (t, J = 7.2 Hz, 2H). |
| 203 | $^1$H NMR (300 MHz, CDCl$_3$): δ 7.75 (d, J = 8.7 Hz, 1H), 7.70-7.23 (m, 10H), 6.25 (s, 1H), 2.50 (s, 3H), 2.41 (t, J = 6.9 Hz, 2H), 1.64 (quin, J = 7.8 Hz, 2H), 1.47-1.29 (m, 4H), 0.93 (t, J = 6.9 Hz, 3H). |
| 204 | $^1$H NMR (300 MHz, CDCl$_3$): δ 7.80 (dd, J = 8.7, 1.5 Hz, 1H), 7.77 (d, J = 8.7 Hz, 1H), 7.59 (d, J = 8.7 Hz, 1H), 7.56-7.28 (m, 6H), 7.00 (dd, J = 8.7, 1.2 Hz, 1H), 6.75 (td, J = 8.1, 0.9 Hz, 1H), 6.27 (d, J = 1.2 Hz, 1H), 2.52 (d, J = 1.2 Hz, 3H). LCMS [M + 1]$^+$: 397.1. |
| 205 | $^1$H NMR (300 MHz, CDCl$_3$): δ 7.74 (d, J = 9.0 Hz, 1H), 7.58-7.51 (m, 6H), 6.24 (s, 1H), 2.49 (s, 3H). |
| 206 | $^1$H NMR (400 MHz, CDCl$_3$): δ 7.84-7.73 (m, 3H), 7.65-7.62 (m, 4H), 7.46-7.25 (m, 5H), 7.07-7.03 (m, 2H), 6.11 (d, J = 0.9 Hz, 1H), 2.44 (d, J = 0.6 Hz, 3H). |
| 207 | LCMS [M + 1]$^+$: 425.1. |
| 208 | $^1$H NMR (300 MHz, CDCl$_3$): δ 8.34 (s, 1H), 7.88-7.82 (m, 4H), 7.79-7.71 (m, 1H), 7.62-7.49 (m, 3H), 7.40 (s, 4H), 6.25 (d, J = 0.9 Hz, 1H), 2.48 (s, 3H). $^{13}$C NMR (75 MHz, CDCl$_3$): δ 184.9, 159.3, 156.3, 152.9, 149.7, 148.4, 135.4, 133.6, 132.1, 132.0, 131.0, 129.4, 128.74, 128.68, 128.2, 127.8, 127.4, 126.8, 124.8, 124.3, 123.1, 115.9, 115.4, 113.5, 109.0, 19.5. |
| 209 | $^1$H NMR (300 MHz, CDCl$_3$): δ 7.91-7.86 (m, 2H), 7.75 (d, J = 8.7 Hz, 1H), 7.58-7.49 (m, 3H), 7.41-7.38 (m, 2H), 7.27-7.03 (m, 2H), 6.27 (s, 1H), 2.51 (s, 3H). $^{13}$C NMR (75 MHz, CDCl$_3$): δ 183.4, 167.4, 164.0, 159.3, 156.2, 152.8, 149.8, 147.9, 132.8, 132.7, 132.5, 132.4, 132.1, 131.0, 128.5, 127.6, 124.5, 123.3, 115.9, 115.7, 115.5, 115.4, 113.7, 108.9, 19.6. |
| 210 | $^1$H NMR (300 MHz, CDCl$_3$): δ 7.80-7.74 (m, 3H), 7.57-7.50 (m, 3H), 7.40-7.26 (m, 4H), 6.27 (s, 1H), 2.50 (s, 3H). $^{13}$C NMR (75 MHz, CDCl$_3$): δ 183.6, 159.3, 156.2, 152.8, 149.8, 147.8, 139.7, 134.8, 132.1, 131.1, 128.6, 128.4, 127.9, 124.6, 123.4, 115.9, 115.5, 113.7, 108.9, 19.5. |
| 211 | $^1$H NMR (300 MHz, CDCl$_3$): δ 7.77-7.69 (m, 4H), 7.58-7.51 (m, 6H), 7.40-7.37 (m, 2H), 6.27 (d, J = 0.9 Hz, 1H), 2.510 (d, J = 0.9 Hz, 3H). $^{13}$C NMR (75 MHz, CDCl$_3$): δ 183.8, 159.3, 156.3, 152.8, 149.8, 147.8, 135.3, 132.1, 131.6, 131.2, 131.1, 128.4, 128.0, 124.6, 123.5, 116.0, 115.5, 113.7, 109.0, 19.6. |
| 212 | $^1$H NMR (300 MHz, CDCl$_3$): δ 7.74-7.70 (m, 3H), 7.55 (dd, J = 9.0, 0.9 Hz, 1H), 7.48 (dd, J = 6.0, 2.1 Hz, 2H), 7.38 (dd, J = 6.0, 2.1 Hz, 2H), 7.16 (d, J = 8.7 Hz, 2H), 6.26 (d, J = 0.9 Hz, 1H), 2.50 (s, 3H), 2.382 (s, 3H). $^{13}$C NMR (75 MHz, CDCl$_3$): δ 184.8, 159.4, 156.3, 152.9, 149.7, 148.4, 144.3, 138.8, 132.2, 131.0, 129.9, 129.0, 128.7, 127.0, 124.2, 123.1, 116.0, 115.4, 113.6, 109.0, 21.7, 19.6. |
| 213 | $^1$H NMR (300 MHz, CDCl$_3$): δ 7.89 (d, J = 8.1 Hz, 2H), 7.78 (d, J = 9.0 Hz, 1H), 7.64-7.55 (m, 3H), 7.50-7.47 (m, 2H), 7.38-7.27 (m, 2H), 2.51 (s, 3H). $^{13}$C NMR (75 MHz, CDCl$_3$): δ 183.9, 159.2, 156.4, 152.8, 149.9, 147.5, 139.6, 134.3, 133.9, 132.1, 131.0, 129.8, 128.8, 128.2, 125.20, 125.15, 125.11, 123.6, 115.9, 115.6, 113.8, 109.0, 19.5. |
| 214 | $^1$H NMR (300 MHz, CDCl$_3$): δ 7.85-7.82 (m, 2H), 7.72 (d, J = 8.7 Hz, 1H), 7.57-7.47 (m, 3H), 7.41-7.38 (m, 2H), 6.85-6.83 (m, 2H), 6.25 (s, 1H), 3.85 (s, 3H), 2.50 (s, 3H). $^{13}$C NMR (75 MHz, CDCl$_3$): δ 183.5, 163.8, 159.4, 156.2, 152.9, 149.6, 148.6, 132.3, 132.2, 131.0, 129.0, 128.8, 126.5, 124.0, 123.0, 115.9, 115.4, 113.6, 113.5, 108.9, 55.5, 19.5. |
| 215 | $^1$H NMR (300 MHz, CDCl$_3$): δ 7.89-7.86 (m, 2H), 7.74 (d, J = 9.0 Hz, 1H), 7.61-7.55 (m, 5H), 7.50-7.36 (m, 7H), 2.50 (d, J = 0.9 Hz, 3H). $^{13}$C NMR (75 MHz, CDCl$_3$): δ 184.6, 159.4, 156.3, 152.9, 149.8, 148.3, 146.0, 139.7, 135.1, 132.2, 131.0, 130.3, 128.9, 128.7, 128.3, 127.5, 127.3, 126.9, 124.4, 123.2, 116.0, 115.4, 113.6, 109.0, 19.6. |
| 216 | $^1$H NMR (300 MHz, CDCl$_3$): δ 8.25-8.22 (m, 2H), 8.00-7.97 (m, 2H), 7.80 (d, J = 8.7 Hz, 1H), 7.59-7.51 (m, 3H), 7.42-7.39 (m, 2H), 6.29 (d, J = 1.2 Hz, 1H), 2.52 (d, J = 1.2 Hz, 3H). $^{13}$C NMR (75 MHz, CDCl$_3$): δ 183.0, 159.1, 156.4, 152.7, 145.0, 149.9, 147.2, 141.6, 132.1, 131.2, 130.5, 129.4, 128.1, 125.3, 123.8, 123.4, 116.0, 115.7, 113.9, 109.0, 19.6. |
| 217 | $^1$H NMR (300 MHz, CDCl$_3$): δ 7.78-7.66 (m, 3H), 7.57 (d, J = 9.0 Hz, 1H), 7.50-7.46 (m, 3H), 7.38-7.27 (m, 3H), 6.27 (d, J = 1.2 Hz, 1H), 2.51 (d, J = 1.2 Hz, 3H). $^{13}$C NMR (75 MHz, CDCl$_3$): δ 183.6, 159.2, 156.4, 152.8, 149.8, 147.6, 138.0, 134.4, 132.8, 132.1, 131.0, 129.64, 129.58, 128.4, 128.3, 127.6, 124.8, 123.441, 115.9, 115.5, 113.7, 109.0, 19.5. |
| 218 | $^1$H NMR (300 MHz, CDCl$_3$): δ 7.90 (d, J = 2.1 Hz, 1H), 7.78 (d, J = 9.0 Hz, 1H), 7.69 (dd, J = 9.0, 2.1 Hz, 1H), 7.60-7.46 (m, 4H), 7.41-7.37 (m, 2H), 6.28 (d, J = 1.2 Hz, 1H), 2.52 (d, J = 1.2 Hz, 3H). $^{13}$C NMR (75 MHz, CDCl$_3$): δ 182.4, 159.2, 156.4, 152.8, 149.9, 147.4, 137.8, 136.0, 132.9, 132.1, 131.6, 131.2, 130.4, 129.5, 128.6, 128.5, 128.3, 125.0, 123.7, 116.0, 115.6, 113.8, 109.0, 19.6. |
| 219 | $^1$H NMR (300 MHz, CDCl$_3$): δ 7.71 (d, J = 9.0 Hz, 1H), 7.54 (d, J = 9.0 Hz, 1H), 7.38-7.30 (m, 3H), 7.22-7.19 (m, 2H), 6.93-6.89 (m, 1H), 6.58 (d, J = 9.0 Hz, 1H), 6.23 (d, J = 1.2 Hz, 1H), 3.63 (s, 3H), 2.48 (d, J = 1.2 Hz, 3H). $^{13}$C NMR (75 MHz, CDCl$_3$): δ 185.2, 159.4, 157.3, 156.3, 152.9, 149.9, 149.2, 133.0, 131.9, 130.3, 130.0, 128.3, 127.7, 127.0, 124.4, 122.9, 120.4, 116.2, 115.2, 113.4, 110.6, 109.0, 55.3, 19.5. |

TABLE 1-continued

| Cpd# | Analytical Data |
|---|---|
| 220 | $^1$H NMR (300 MHz, CDCl$_3$): δ 7.89-7.38 (m, 11H), 6.89-6.83 (m, 2H), 6.14 (d, J = 1.2 Hz, 1H), 2.38 (d, J = 0.9 Hz, 3H). |
| 221 | $^1$H NMR (300 MHz, CDCl$_3$): δ 7.68 (d, J = 9.0 Hz, 1H), 7.47 (d, J = 9.0 Hz, 1H), 7.39-7.32 (m, 2H), 7.19-7.08 (m, 1H), 7.04-6.89 (m, 3H), 6.81-6.72 (m, 1H), 6.17 (d, J = 1.2 Hz, 1H), 2.41 (d, J = 0.9 Hz, 1H). |
| 222 | $^1$H NMR (300 MHz, CDCl$_3$): δ 7.70-7.48 (m, 4H), 7.42-7.35 (m, 4H), 6.18 (d, J = 1.2 Hz, 1H), 2.31 (d, J = 1.2 Hz, 3H). |
| 223 | $^1$H NMR (300 MHz, CDCl$_3$): δ 7.87-7.82 (m, 2H), 7.73 (d, J = 8.7 Hz, 1H), 7.563 (d, J = 8.7 Hz, 1H), 7.48-7.44 (m, 2H), 7.36-7.32 (m, 2H), 6.87-6.82 (m, 2H), 6.27 (d, J = 1.2 Hz, 1H), 3.85 (s, 3H), 2.51 (d, J = 0.9 Hz, 3H). |
| 224 | $^1$H NMR (300 MHz, CDCl$_3$): δ 7.80 (d, J = 7.2 Hz, 2H), 7.75 (d, J = 8.7 Hz, 1H), 7.58 (d, J = 8.7 Hz, 1H), 7.53-7.48 (m, 2H), 7.44-7.30 (m, 4H), 6.27 (s, 1H), 2.51 (s, 3H). |
| 225 | $^1$H NMR (300 MHz, CDCl$_3$): δ 7.81-7.77 (m, 2H), 7.46-7.35 (m, 5H), 6.19 (d, J = 0.9 Hz, 1H), 2.42 (d, J = 1.2 Hz, 3H). $^{13}$C NMR (75 MHz, CDCl$_3$): δ 160.7, 156.8, 156.7, 153.5, 129.3, 129.0, 128.8, 124.9, 120.2, 118.5, 114.6, 114.5, 112.6, 107.9, 98.3, 19.2. |
| 226 | $^1$H NMR (300 MHz, CDCl$_3$): δ 7.50-7.19 (m, 7H), 6.81 (s, 1H), 6.16 (d, J = 0.9 Hz, 1H), 5.93 (s, 1H), 3.70 (brs, 1H), 2.40 (d, J = 0.9 Hz, 3H). |
| 227 | $^1$H NMR (300 MHz, CDCl$_3$): δ 8.16 (dd, J = 8.1, 1.5 Hz, 2H), 7.58 (d, J = 8.7 Hz, 1H), 7.51-6.45 (m, 4H), 2.68 (s, 3H). $^{13}$C NMR (75 MHz, CDCl$_3$): δ 156.1, 155.2, 151.9, 151.5, 146.2, 129.7, 129.6, 128.7, 128.6, 127.0, 121.8, 117.2, 115.1, 111.4, 108.8, 90.5, 20.3. |
| 228 | $^1$H NMR (400 MHz, CDCl$_3$): δ 7.50-7.48 (m, 1H), 7.42-7.38 (m, 3H), 7.34-7.20 (m, 6H), 7.06 (d, J = 7.2 Hz, 2H), 6.12 (q, J = 1.2 Hz, 1H), 4.19 (s, 2H), 3.56 (s, 3H), 2.46 (d, J = 1.2 Hz, 3H). $^{13}$C NMR (100 MHz, CDCl$_3$): δ 161.0 (C), 153.7 (C), 148.8 (C), 139.3 (C), 138.5 (C), 136.2 (C), 134.3 (C), 130.6 (CH × 2), 128.7 (CH × 2), 127.82 (CH × 2), 127.79 (CH × 2), 126.9 (CH), 126.5 (CH), 117.3 (CH), 116.8 (C), 114.5 (C), 111.9 (C), 111.3 (CH), 105.9 (CH), 30.7 (CH$_2$), 30.6 (CH$_3$), 19.6 (CH$_3$). EIMS m/z (relative intensity) 379 (M$^+$, 100), 351 (6), 302 (13), 274 (8), 150 (5), 84 (11). HRMS Calcd. for C$_{26}$H$_{21}$NO$_2$ 379.4504, found 379.1559. |
| 229 | $^1$H NMR (300 MHz, d6-DMSO): δ 11.78 (br, 1H), 7.46-7.11 (m, 12H), 6.14 (q, J = 1.2 Hz, 1H), 4.07 (s, 2H), 2.45 (d, J = 1.2 Hz, 3H). $^{13}$C NMR (75 MHz, d6-DMSO): δ 160.0 (C), 154.8 (C), 148.2 (C), 139.2 (C), 138.4 (C), 135.9 (C), 134.5 (C), 130.5 (CH × 2), 128.6 (CH × 2), 128.1 (CH × 3), 127.7 (CH × 2), 126.3 (CH × 2), 117.7 (CH), 114.4 (C), 114.1 (C), 111.2 (C), 110.2 (CH), 108.5 (CH), 31.5 (CH$_2$), 19.1 (CH$_3$). EIMS m/z (relative intensity) 365 (88), 288 (23), 260 (13), 249 (14), 221 (15), 217 (26), 213 (19), 158 (27), 131 (30), 111 (100), 91 (68). HRMS Calcd. for C$_{25}$H$_{19}$NO$_2$ 365.1416, found 365.1415. IR (neat): 3221 (br), 1701, 1560, 1458 cm$^{-1}$. |
| 230 | $^1$H NMR (300 MHz, CDCl$_3$): δ 8.13-8.08 (m, 2H), 7.67 (d, J = 9.0 Hz, 1H), 7.46 (d, J = 9.0 Hz, 1H), 7.04-6.99 (m, 2H), 6.30 (d, J = 0.9 Hz, 1H), 3.92 (s, 3H), 2.91 (s, 3H), 2.52 (d, J = 0.9 Hz, 3H). |
| 231 | $^1$H NMR (600 MHz, d6-DMSO): δ 8.30 (d, J = 8.0 Hz, 1H), 7.75 (d, J = 8.6 Hz, 1H), 7.60 (d, J = 8.0 Hz, 1H), 7.49-7.47 (m, 2H), 7.32-7.30 (m, 1H), 6.28 (q, J = 1.0 Hz, 1H), 2.49 (d, J = 1.0 Hz, 3H). $^{13}$C NMR (150 MHz, d6-DMSO): δ 160.2 (C), 155.0 (C), 149.8 (C), 142.5 (C), 139.5 (C), 126.1 (CH), 122.6 (CH), 122.2 (CH), 120.5 (C), 120.2 (C), 111.6 (CH), 111.0 (C), 109.9 (CH), 109.4 (C), 108.2 (CH), 18.9 (CH$_3$). EIMS m/z (relative intensity) 249 (M$^+$, 100), 221 (87), 193 (16), 158 (44), 130 (44), 111 (97), 91 (95). HRMS Calcd. for C$_{16}$H$_{11}$NO$_2$ 249.0790, found 249.0790. IR (neat): 3250 (br), 1697, 1630, 1598, 1385, 1336, 1085 cm$^{-1}$. |
| 232 | $^1$H NMR (600 MHz, CDCl$_3$): δ 8.64 (dd, J = 0.6, 7.7 Hz, 1H), 8.08-8.07 (m, 2H), 7.68-7.24 (m, 7H), 7.12 (d, J = 8.6 Hz, 1H), 6.22 (q, J = 1.1 Hz, 1H), 5.72 (s, 2H), 2.49 (d, J = 1.1 Hz, 3H). $^{13}$C NMR (100 MHz, CDCl$_3$): δ 192.0 (C), 161.4 (C), 153.8 (C), 143.3 (C), 140.5 (C), 134.5 (C), 134.4 (CH), 129.2 (CH × 2), 128.5 (CH), 128.1 (CH × 2), 126.4 (C), 124.1 (CH), 122.0 (CH), 121.5 (C), 121.2 (CH), 113.7 (C), 112.3 (C), 111.2 (CH), 108.3 (CH), 107.3 (C), 105.2 (CH), 49.1 (CH$_2$), 19.3 (CH$_3$). EIMS m/z (relative intensity) 367 (M$^+$, 70), 270 (54), 262 (100), 249 (53), 221 (40), 191 (20), 105 (86), 77 (23). HRMS Calcd. for C$_{24}$H$_{17}$NO$_3$ 367.1208, found 367.1197. IR (neat): 1718, 1701, 1630, 1601, 1448, 1390, 1224 cm$^{-1}$. |
| 233 | $^1$H NMR (300 MHz, CDCl$_3$): δ 7.72 (d, J = 9.0 Hz, 1H), 7.58 (d, J = 9.0 Hz, 1H), 7.50-7.06 (m, 9H), 6.27 (d, J = 1.2 Hz, 1H), 4.65 (t, J = 2.7 Hz, 2H), 2.54-2.51 (m, 4H). |
| 234 | $^1$H NMR (300 MHz, CDCl$_3$): δ 7.86-7.73 (m, 3H), 7.66-7.55 (m, 2H), 7.47-7.34 (m, 6H), 6.22 (d, J = 1.2 Hz, 1H), 5.89 (s, 1H), 2.60 (brs, 1H), 2.48 (d, J = 1.2 Hz, 3H). |
| 235 | $^1$H NMR (300 MHz, CDCl$_3$): δ 7.71-7.64 (m, 3H), 7.57-7.45 (m, 4H), 6.26 (d, J = 1.2 Hz, 1H), 5.18-5.02 (m, 2H), 3.81-3.71 (m, 1H), 2.95-2.67 (m, 2H), 2.50 (d, J = 1.2 Hz, 3H), 2.39-2.18 (m, 2H). |
| 236 | $^1$H NMR (400 MHz, CDCl$_3$): δ 7.74 (d, J = 6.6 Hz, 1H), 7.59 (d, J = 6.6 Hz, 1H), 7.49-6.96 (m, 9H), 6.26 (d, J = 0.6 Hz, 1H), 3.93 (t, J = 6.0 Hz, 2H), 3.26 (t, J = 5.1 Hz, 2H), 2.51 (s, 3H), 2.05-1.85 (m, 4H). |
| 237 | $^1$H NMR (300 MHz, CDCl$_3$): δ 7.74 (d, J = 9.0 Hz, 1H), 7.58 (d, J = 9.0 Hz, 1H), 7.50-6.96 (m, 9H), 6.26 (d, J = 1.2 Hz, 1H), 4.08 (t, J = 6.6 Hz, 2H), 3.90 (t, J = 6.3 Hz, 2H), 2.51 (d, J = 0.9 Hz, 3H), 2.05 (s, 3H), 1.82-1.38 (m, 8H). |
| 238 | $^1$H NMR (400 MHz, CDCl$_3$): δ 7.74 (d, J = 6.6 Hz, 1H), 7.57 (d, J = 6.6 Hz, 1H), 7.50-6.92 (m, 9H), 6.26 (d, J = 0.6 Hz, 1H), 2.51 (d, J = 0.6 Hz, 3H), 0.98 (s, 9H), 0.192 (s, 6H). |

TABLE 1-continued

| Cpd# | Analytical Data |
|---|---|
| 239 | $^1$H NMR (300 MHz, d6-DMSO): δ 7.93 (d, J = 9.3 Hz, 1H), 7.76 (d, J = 9.3 Hz, 1H), 7.72-7.69 (m, 2H), 7.56-7.51 (m, 1H), 7.40-7.35 (m, 2H), 7.28 (d, J = 8.4 Hz, 2H), 6.51 (d, J = 8.4 Hz, 2H), 6.36 (s, 1H), 2.49 (s, 3H). $^{13}$C NMR (75 MHz, d6-DMSO): δ 185.1 (C), 158.9 (C), 157.6 (C), 155.9 (C), 154.0 (C), 149.4 (C), 147.1 (C), 136.6 (C), 132.9 (CH), 132.1 (CH × 2), 129.3 (CH × 2), 128.2 (CH × 2), 128.1 (C), 125.3 (CH), 119.8 (C), 115.5 (C), 115.1 (C), 114.4 (CH × 2), 112.7 (CH), 108.9 (CH), 19.0 (CH$_3$). IR (neat): 3350 (br), 2957, 2925, 2853, 1731, 1708, 1647, 1601, 1552, 1509, 1472, 1447, 1357, 1269, 1172, 1081 cm$^{-1}$. EIMS m/z (relative intensity) 396 (M$^+$, 16), 105 (5), 79 (25), 78 (100), 63 (82). HRMS Calcd. for C$_{25}$H$_{16}$O$_5$ 396.0998, found 396.0998. |
| 240 | $^1$H NMR (400 MHz, CDCl$_3$): δ 7.74 (d, J = 8.8 Hz, 1H), 7.58 (d, J = 8.8 Hz, 1H), 6.26 (s, 1H), 7.52-7.02 (m, 13H), 4.14 (t, J = 5.6 Hz, 2H), 2.96-2.87 (m, 8H), 2.51 (s, 3H). |
| 241 | $^1$H NMR (300 MHz, CDCl$_3$): δ 7.73 (d, J = 9.0 Hz, 1H), 7.57 (d, J = 9.0 Hz, 1H), 7.54-7.17 (m, 8H), 7.05 (ddd, J = 8.4, 2.7, 0.9 Hz, 1H), 6.25 (d, J = 1.2 Hz, 1H), 4.13 (t, J = 5.4 Hz, 2H), 4.06 (s, 4H), 3.16 (t, J = 5.7 Hz, 2H), 2.47 (d, J = 1.2 Hz, 3H). |
| 242 | $^1$H NMR (300 MHz, CDCl$_3$): δ 7.74 (d, J = 9.0 Hz, 1H), 7.58 (d, J = 9.0 Hz, 1H), 7.50-7.27 (m, 7H), 7.18 (t, J = 8.4 Hz, 1H), 6.98 (dd, J = 8.4, 2.4 Hz, 1H), 6.26 (d, J = 1.2 Hz, 1H), 3.90 (t, J = 6.6 Hz, 2H), 2.51 (d, J = 1.2 Hz, 3H), 1.75 (quin, J = 6.3 Hz, 2H), 1.43-1.26 (m, 8H), 0.90 (t, J = 6.9 Hz, 3H). |
| 243 | $^1$H NMR (300 MHz, CDCl$_3$): δ 7.72 (d, J = 8.7 Hz, 1H), 7.56 (d, J = 8.7 Hz, 1H), 7.50-7.27 (m, 7H), 7.18 (t, J = 8.1 Hz, 1H), 6.98 (ddd, J = 8.1, 2.7, 0.9 Hz, 1H), 6.24 (d, J = 0.9 Hz, 1H), 3.89 (t, J = 6.6 Hz, 2H), 2.49 (d, J = 0.9 Hz, 3H), 1.75 (quin, J = 6.6 Hz, 2H), 1.46-1.29 (10H, m), 0.87 (t, J = 6.6 Hz, 3H). |
| 244 | $^1$H NMR (300 MHz, CDCl$_3$): δ 7.74 (d, J = 9.0 Hz, 1H), 7.58 (d, J = 9.0 Hz, 1H), 7.50-7.27 (m, 7H), 7.18 (t, J = 8.4 Hz, 1H), 6.98 (ddd, J = 8.4, 2.4, 0.9 Hz, 1H), 6.26 (d, J = 1.2 Hz, 1H), 3.89 (t, J = 6.6 Hz, 2H), 2.51 (d, J = 1.2 Hz, 3H), 1.75 (quin, J = 7.2 Hz, 1H), 1.50-1.27 (m, 15H), 0.88 (t, J = 6.6 Hz, 3H). |
| 245 | $^1$H NMR (300 MHz, CDCl$_3$): δ 7.76 (d, J = 9.0 Hz, 1H), 7.58 (d, J = 9.0 Hz, 1H), 7.47-6.79 (m, 8H), 6.28 (d, J = 1.2 Hz, 1H), 3.82 (s, 3H), 2.51 (d, J = 1.2 Hz, 3H). |
| 246 | $^1$H NMR (300 MHz, CDCl$_3$): δ 7.75 (d, J = 9.0 Hz, 1H), 7.58 (d, J = 9.0 Hz, 1H), 7.44-7.02 (m, 8H), 6.27 (d, J = 1.2 Hz, 1H), 3.80 (s, 3H), 2.51 (d, J = 1.2 Hz, 3H). |
| 247 | $^1$H NMR (300 MHz, CDCl$_3$): δ 7.70 (d, J = 8.7 Hz, 1H), 7.53 (d, J = 8.7 Hz, 1H), 7.36-7.09 (m, 7H), 6.98-6.94 (m, 1H), 6.22 (d, J = 1.2 Hz, 1H), 3.73 (s, 3H), 2.47 (d, J = 0.9 Hz, 1H), 2.03 (s, 3H). $^{13}$C NMR (75 MHz, CDCl$_3$): δ 185.4, 159.4, 159.1, 156.4, 152.8, 149.9, 147.9, 137.8, 137.1, 131.5, 129.4, 129.3, 129.0, 128.9, 127.6, 124.2, 122.2, 119.5, 116.2, 115.2, 113.43, 113.38, 108.8, 55.2, 21.1, 19.4. |
| 248 | $^1$H NMR (400 MHz, CDCl$_3$): δ 7.75-7.69 (m, 3H), 7.54 (d, J = 8.8 Hz, 1H), 7.46-7.34 (m, 3H), 7.30-7.26 (m, 2H), 6.84-6.80 (m, 2H), 6.24 (q, J = 1.2 Hz, 1H), 3.78 (s, 3H), 2.48 (d, J = 1.2 Hz, 3H). $^{13}$C NMR (100 MHz, CDCl$_3$): δ 185.6 (C), 160.0 (C), 159.6 (C), 156.5 (C), 152.9 (C), 150.1 (C), 148.0 (C), 136.7 (C), 132.8 (CH), 132.1 (CH × 2), 129.7 (CH × 2), 128.7 (C), 128.1 (CH × 2), 124.1 (CH), 121.6 (C), 116.4 (C), 115.3 (C), 113.5 (CH), 113.3 (CH × 2), 109.0 (CH), 55.2 (CH$_3$), 19.6 (CH$_3$). IR (neat): 3058 (w), 2927 (w), 2834 (w), 1730 (s), 1652 (m), 1602 (s), cm$^{-1}$. EIMS m/z (relative intensity) 410 (M$^+$, 62), 152 (11), 105 (78), 77 (100), 57 (43), 55 (36). HRMS Calcd. for C$_{26}$H$_{18}$O$_5$ 410.1154, found 410.1153 |
| 249 | $^1$H NMR (300 MHz, CDCl$_3$): δ 7.60-7.00 (m, 11H), 6.11 (s, 1H), 2.40 (d, J = 1.2 Hz, 3H). |
| 250 | $^1$H NMR (300 MHz, CDCl$_3$): δ 7.74 (d, J = 8.7 Hz, 1H), 7.58 (d, J = 8.7 Hz, 1H), 7.50-7.16 (m, 13H), 7.00 (dd, J = 8.4, 2.7 Hz, 1H), 6.53 (d, J = 15.9 Hz, 1H), 6.21~5.30 (m, 2H), 4.05 (t, J = 5.7 Hz, 2H), 3.20-2.96 (m, 2H), 2.81 (t, J = 5.4 Hz, 2H), 2.63-2.47 (m, 7H). |
| 251 | $^1$H NMR (300 MHz, CDCl$_3$): δ 7.62 (d, J = 9.0 Hz, 1H), 7.360 (d, J = 9.0 Hz, 1H), 7.312-7.308 (m, 2H), 7.29-7.09 (m, 6H), 6.95-6.92 (m, 1H), 6.08 (s, 1H), 3.86 (t, J = 6.3 Hz, 2H), 3.72-3.58 (m, 3H), 3.43-3.30 (m, 1H), 2.87-2.79 (m, 1H), 2.68-2.57 (m, 3H), 2.32 (d, J = 0.9 Hz, 3H), 1.89-1.84 (m, 2H), 1.038 (t, J = 7.2 Hz, 1H). |
| 252 | $^1$H NMR (300 MHz, CDCl$_3$): δ 7.75 (d, J = 9.0 Hz, 1H), 7.58 (d, J = 8.7 Hz, 2H), 7.50-7.46 (m, 2H), 7.42-7.36 (m, 2H), 7.32-7.24 (m, 2H), 7.09-7.05 (m, 1H), 6.27 (d, J = 1.2 Hz, 1H), 3.81 (s, 3H), 2.51 (d, J = 0.9 Hz, 3H). |
| 253 | $^1$H NMR (300 MHz, CDCl$_3$): δ 7.77-7.73 (m, 2H), 7.59-7.56 (m, 2H), 7.55-7.45 (m, 2H), 7.39-7.36 (m, 2H), 7.30-7.26 (m, 2H), 6.27 (d, J = 1.2 Hz, 1H), 3.90 (t, J = 6.6 Hz, 2H), 2.51 (d, J = 1.2 Hz, 3H), 1.84-1.77 (m, 2H), 1.04 (d, J = 7.5 Hz, 3H). |
| 254 | $^1$H NMR (300 MHz, CDCl$_3$): δ 8.18-8.17 (m, 1H), 7.78-7.75 (m, 2H), 7.63-7.59 (m, 4H), 7.52-7.49 (m, 1H), 7.21-7.20 (m, 1H), 6.28 (s, 1H), 2.51 (d, J = 0.6 Hz, 3H). |
| 255 | $^1$H NMR (300 MHz, CDCl$_3$): δ 7.74-7.71 (m, 3H), 7.58 (d, J = 9.0 Hz, 1H), 7.53-7.39 (m, 4H), 6.26 (d, J = 1.2 Hz, 1H), 2.51 (d, J = 1.2 Hz, 3H). LCMS [M + 1]$^+$: 277.1. |
| 256 | $^1$H NMR (300 MHz, CDCl$_3$): δ 7.75 (d, J = 8.7 Hz, 1H), 7.58 (d, J = 9.0 Hz, 2H), 7.56-7.44 (m, 2H), 7.39-7.36 (m, 1H), 7.30-7.22 (m, 3H), 7.05-7.02 (m, 1H), 6.27 (d, J = 1.5 Hz, 1H), 3.81 (s, 3H), 2.51 (d, J = 1.2 Hz, 3H). $^{13}$C NMR (75 MHz, CDCl$_3$): δ 184.9, 159.3, 159.2, 156.2, 152.8, 149.7, 148.2, 137.6, 133.5, 131.7, 131.6, 129.2, 129.1, 127.1, 124.5, 122.2, 121.5, 119.7, 115.9, 115.4, 113.6, 113.5, 108.9, 55.3, 19.5. |
| 257 | $^1$H NMR (300 MHz, CDCl$_3$): δ 8.05-8.04 (m, 1H), 7.99-7.63 (m, 2H), 7.58-7.39 (m, 3H), 7.27-7.12 (m, 2H), 6.24 (s, 1H), 2.48 (s, 3H). |
| 258 | $^1$H NMR (300 MHz, CDCl$_3$): δ 8.19-8.17 (m, 1H), 7.78-7.75 (m, 3H), 7.61-7.55 (m, 4H), 7.37 (dd, J = 7.5, 7.5 Hz, 1H), 7.21-7.18 (m, 1H), 6.26 (d, J = 1.2 Hz, 1H), 2.51 (d, J = 1.2 Hz, 3H). $^{13}$C NMR (75 MHz, CDCl$_3$): δ 175.0, 159.2, 155.9, 152.6, 149.7, 147.5, 142.6, 135.3, 134.9, 133.3, 131.9, 131.7, 129.3, 129.0, 128.3, 127.2, 124.5, 121.7, 116.4, 115.5, 113.8, 108.8, 19.6. |

TABLE 1-continued

| Cpd# | Analytical Data |
|---|---|
| 259 | $^1$H NMR (300 MHz, CDCl$_3$): δ 7.73 (d, J = 8.7 Hz, 1H), 7.56-7.48 (m, 2H), 7.48-7.43 (m, 2H), 7.34-7.17 (m, 3H), 7.01-6.98 (m, 1H), 6.27 (d, J = 0.9 Hz, 1H), 2.50 (d, J = 1.2 Hz, 3H). $^{13}$C NMR (75 MHz, CDCl$_3$): δ 175.0, 159.2, 155.9, 152.6, 149.7, 147.5, 142.6, 135.3, 134.9, 133.3, 131.9, 131.7, 129.3, 129.0, 128.3, 127.2, 124.5, 121.7, 116.4, 115.5, 113.8, 108.8, 19.6. |
| 260 | $^1$H NMR (300 MHz, CDCl$_3$): δ 7.73 (d, J = 9.0 Hz, 1H), 7.58-7.54 (m, 2H), 7.48-7.43 (m, 2H), 7.37-7.34 (m, 1H), 7.27-7.20 (m, 3H), 7.03-6.99 (m, 1H), 6.24 (d, J = 1.2 Hz, 1H), 4.00 (d, J = 7.2 Hz, 2H), 2.48 (d, J = 1.2 Hz, 3H), 1.40 (d, J = 7.2 Hz, 3H). $^{13}$C NMR (75 MHz, CDCl$_3$): δ 184.9, 159.1, 158.7, 156.2, 152.8, 148.2, 137.6, 133.4, 131.7, 131.6, 129.2, 129.15, 129.09, 127.0, 124.4, 122.1, 121.5, 120.1, 115.8, 115.4, 114.2, 113.5, 108.9, 63.6, 19.5, 14.7. |
| 261 | $^{13}$C NMR (75 MHz, CDCl$_3$): δ 185.0, 159.2, 158.9, 156.2, 152.8, 149.7, 148.3, 137.6, 133.5, 131.7, 131.6, 129.2, 129.1, 127.0, 124.4, 122.0, 121.5, 120.1, 115.9, 115.4, 114.2, 113.6, 108.9, 69.6, 31.5, 19.5, 14.1. |
| 262 | $^1$H NMR (300 MHz, CDCl$_3$): δ 7.74 (d, J = 8.7 Hz, 1H), 7.58-7.56 (m, 2H), 7.55-7.44 (m, 2H), 7.44-7.34 (m, 1H), 7.27-7.20 (m, 3H), 7.03-7.00 (m, 1H), 6.25 (d, J = 1.2 Hz, 1H), 3.93 (t, J = 6.6 Hz, 2H), 2.49 (d, J = 1.2 Hz, 3H), 1.78-1.71 (m, 2H), 1.52-1.45 (m, 2H), 0.98 (d, J = 6.6 Hz, 3H). $^{13}$C NMR (75 MHz, CDCl$_3$): δ 185.0, 159.2, 158.9, 156.3, 152.8, 148.3, 137.6, 133.5, 131.7, 131.6, 129.2, 129.1, 127.0, 124.4, 122.0, 121.6, 120.2, 115.4, 114.2, 113.6, 108.9, 67.8, 31.1, 19.5, 19.1, 13.8. |
| 263 | $^1$H NMR (300 MHz, CDCl$_3$): δ 7.72 (d, J = 8.7 Hz, 1H), 7.56-7.48 (m, 2H), 7.46-7.43 (m, 2H), 7.36-7.34 (m, 1H), 7.27-7.19 (m, 3H), 7.03-6.99 (m, 1H), 6.24 (d, J = 1.2 Hz, 1H), 3.91 (t, J = 6.6 Hz, 2H), 2.48 (s, 3H), 1.79-1.75 (m, 2H), 1.46-1.34 (m, 4H), 0.93 (d, J = 6.6 Hz, 3H). $^{13}$C NMR (75 MHz, CDCl$_3$): δ 185.0, 159.1, 158.9, 156.2, 152.8, 149.6, 148.2, 137.5, 133.5, 131.7, 131.6, 129.15, 129.08, 127.0, 124.4, 122.0, 121.5, 120.1, 115.8, 115.4, 114.2, 113.5, 108.9, 68.1, 28.7, 28.0, 22.3, 19.5, 13.9. |
| 264 | $^1$H NMR (300 MHz, CDCl$_3$): δ 7.82-7.79 (m, 2H), 7.68 (d, J = 8.7 Hz, 1H), 7.57-7.54 (m, 3H), 6.54-6.51 (m, 2H), 6.25 (d, J = 0.9 Hz, 1H), 3.04 (s, 6H), 2.50 (d, J = 1.5 Hz, 3H). |
| 265 | $^1$H NMR (300 MHz, CDCl$_3$): δ 7.82 (d, J = 9.0 Hz, 2H), 7.72 (d, J = 8.7 Hz, 1H), 7.57 (d, J = 8.7 Hz, 1H), 7.52-7.33 (m, 5H), 6.80 (d, J = 9.0 Hz, 2H), 6.26 (d, J = 0.9 Hz, 1H), 4.13 (t, J = 5.6 Hz, 2H), 3.74 (m, 4H), 2.80 (t, J = 5.6 Hz, 2H), 2.57 (m, 4H), 2.51 (d, J = 0.9 Hz, 3H). |
| 266 | $^1$H NMR (300 MHz, CDCl$_3$): δ 7.81 (d, J = 8.7 Hz, 2H), 7.72 (d, J = 9.0 Hz, 1H), 7.58 (d, J = 8.7 Hz, 1H), 7.51-7.33 (m, 5H), 6.81 (d, J = 9.3 Hz, 2H), 6.26 (d, J = 0.9 Hz, 1H), 4.08 (t, J = 5.7 Hz, 2H), 2.73 (t, J = 5.6 Hz, 2H), 2.51 (d, J = 0.9 Hz, 3H), 2.34 (s, 6H). |
| 267 | $^1$H NMR (400 MHz, CDCl$_3$): δ 7.83 (d, J = 6.6 Hz, 2H), 7.72 (d, J = 6.6 Hz, 1H), 7.58 (d, J = 6.0 Hz, 1H), 7.51-7.21 (m, 9H), 6.84 (d, J = 6.3 Hz, 2H), 6.26 (s, 1H), 4.20 (t, J = 4.2 Hz, 2H), 4.07 (s, 4H), 3.19 (t, J = 8.7 Hz, 2H), 2.51 (s, 3H). |

Example 3

In Vitro Anticancer Assay (Growth Inhibition Assay)

Anticancer activities of the compounds of this invention were evaluated using a growth inhibition assay described in Kuo et al., *Cancer Res.* 2004, 64(13), 4621-4628.

Human cervical carcinoma KB cells were maintained in plastic dishes in DMEM medium supplemented with 10% fetal bovine serum. For in vitro treatment, tumor cells were seeded in 100 mL of culture medium/well in 96-well plates to a final cell density of 6×10$^3$ cell/mL and incubated in a CO$_2$ incubator at 37° C. for 24 h. The cells were treated with at least five different concentrations of a test compound, and incubated in a CO$_2$ incubator at 37° C. for 72 h. The number of viable cells was estimated using MTS assay and absorbance was measured at 490 nm. For each test compound, dose-response curves were measured with at least five different drug concentrations, and the concentration causing 50% cell growth inhibition (IC$_{50}$) compared with the control was calculated.

Compounds 1-4, 6, 8-12, 16-22, 26, 30-92, 94-98, 100-102, 105-107, 109-122, 127-151, 153-161, 165, 166, 170-191, and 193-266 were tested in this assay. Unexpectedly, Compounds 8, 19, 21, 22, 35, 37, 52, 91, 97, 102, 110, 112, 117, 119, 127, 156, 158, 174, 176, 208, 210-212, 214, 223, 265, and 266 showed IC$_{50}$ values between 1 μM and 10 μM; Compounds 2, 3, 10, 11, 26, 36, 38, 41, 42, 46, 49-51, 58, 60-62, 66, 85, 88-90, 92, 94, 98, 116, 133, 135-138, 153-155, 157, 159, 161, 165, 173, 175, 177, 183, 184, 189, 190, 193-195, 197-199, 204, 206, 209, 217, 219-221, 224, 226, 244, 248, 251, 253, 254, and 264 showed IC$_{50}$ values between 101 nM and 999 nM; and Compounds 1, 4, 6, 9, 14, 20, 30-34, 39, 40, 44, 45, 47, 48, 53-57, 59, 67-84, 86, 87, 95, 96, 100, 107, 115, 132, 134, 139-148, 150, 151, 160, 166, 170-172, 178-182, 185-188, 191, 196, 200-203, 207, 222, 233, 234, 236-243, 246, 247, 249, 250, 252, and 256-263 showed IC$_{50}$ values between 0.1 nM and 100 nM.

Compound 1 was evaluated against 21 human tumor cell lines derived from nine cancer cell types: nasopharyngeal carcinoma (HONE-1, CPT 30, and HONE-cis6), cervical carcinoma (KB, KB-CPT100, KB7D, KB-1036, KB-S15, and KB-vin10), gastric carcinoma (TSGH), breast carcinoma (MCF-7), colorectal carcinoma (HT29), non-small cell lung carcinoma (H460), lymphoma (BJAB and H9), leukemia (CEM and HL 60), and hepatocellular carcinoma (Hep 3B, Hep G2, Huh 7, and Hcc36). As indicated in Table 2 below, some of the above cell lines are resistant to certain conventional anticancer drugs ("drug-resistant cells"). Compound 140 was tested against the following 15 cell lines: HONE-1, CPT 30, and HONE-cis6, KB, KB-CPT100, KB7D, KB-1036, KB-S 15, and KB-vin10, TSGH, MCF-7, H460, BJAB, H9, and Hep G2. Compound 32 was tested against the following 8 cell lines: HONE-1, KB, TSGH, MCF-7, H460, BJAB, H9, and Hep G2.

Cells in logarithmic growth phase were cultured at a density of 5000 cells/ml/well in a 24-well plate. Drug-resistant cells were cultured in a medium free of test compounds for 3 days before use. The cells were exposed to various concentrations of a test compound for 72 h. The methylene blue dye assay was used to evaluate the effect of the test compound on cell growth, as has been described in Finlay et al., *Anal. Biochem.* 1984, 139, 272-277. The $IC_{50}$ value resulting from 50% inhibition of cell growth was calculated graphically as a comparison with control growth. Unexpectedly, Compounds 1 and 140 showed $IC_{50}$ values less than 10 nM for most of the tested cell lines; and Compound 32 showed $IC_{50}$ values less than 150 nM for most of the tested cell lines.

TABLE 2

| Cell lines | Compound 1 $IC_{50}$ | Compound 140 $IC_{50}$ | Compound 32 $IC_{50}$ | Notes |
| --- | --- | --- | --- | --- |
| HONE1 | 2 nM | 3 nM | 55 nM | |
| CPT30 | 8.5 nM | 10.5 nM | n/a | Drug-resistant cell lines were generated by camptothecin-driven selection. |
| HONE-cis6 | 4.5 nM | 10 nM | n/a | Drug-resistant cell lines were generated by cisplatin-driven selection. |
| KB | 1.3-1.8 nM | 7.7 nM | 41 nM | |
| KB-CPT100 | 6.25 nM | 9 nM | n/a | Drug-resistant cell lines were generated by camptothecin-driven selection. |
| KB7D | 0.8 nM | 8 nM | n/a | KB-7D cells were generated by VP-16-driven selection. |
| KB-1036 | 4 nM | 13 nM | n/a | KB-1036 cells were generated by D-501036 driven selection. |
| KB-S15 | 0.5 nM | 10 nM | n/a | Drug-resistant cell lines were generated by paclitaxel-driven selection. |
| KB-vin10 | 2.5 nM | 10 nM | n/a | KB-VIN10 cells were generated by vincristine-driven selection. |
| TSGH | 17 nM | 41 nM | 150 nM | |
| MCF7 | 4 nM | 13 nM | 150 nM | |
| HT29 | 7 nM | n/a | n/a | |
| H460 | 0.5 nM | 3 nM | 40 nM | |
| BJAB | 110 nM | 60 nM | 45 nM | |
| H9 | 3.5 nM | 20 nM | 124 nM | |
| CEM | 1 μM | n/a | n/a | |
| HL60 | 1 μM | n/a | n/a | |
| Hep 3B | 35 μM | n/a | n/a | |
| Hep G2 | 3.5 μM | 2.6 μM | 5.5 μM | |
| Huh 7 | 26.7 μM | n/a | n/a | |
| Hcc36 | 10.8 μM | n/a | n/a | |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

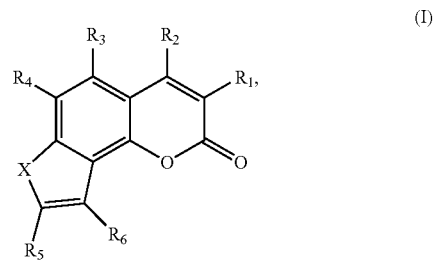

wherein
each of $R_1$, $R_2$, $R_3$, and $R_4$, independently, is H, alkyl, alkenyl, alkynyl, cycloalkyl, cycloalkenyl, heterocycloalkyl, heterocycloalkenyl, aryl, heteroaryl, halo, nitro, cyano, amino, hydroxy, alkoxy, aryloxy, $C(O)R_a$, $C(O)OR_a$, $C(O)NR_aR_b$, $C(S)R_b$, or $C(NR_b)R_a$, in which each of $R_a$ and $R_b$, independently, is H, alkyl, alkenyl, alkynyl, hydroxy, alkoxy, amino, cycloalkyl, cycloalkenyl, heterocycloalkyl, heterocycloalkenyl, aryl, or heteroaryl; or $R_1$ and $R_2$, together with the carbon atoms to which they are bonded, are cycloalkenyl, heterocycloalkenyl, aryl, or heteroaryl; or $R_2$ and $R_3$, together with the carbon atoms to which they are bonded, are cycloalkenyl or heterocycloalkenyl; or $R_3$ and $R_4$, together with the carbon atoms to which they are bonded, are cycloalkenyl, heterocycloalkenyl, aryl, or heteroaryl;

$R_5$ is $C(O)R_c$, in which $R_c$ is aryl substituted at the 2- or 3-position with halo, nitro, cyano, or alkoxy;

$R_6$ is aryl; and

X is O.

2. The compound of claim 1, wherein $R_6$ is phenyl.

3. The compound of claim 1, wherein $R_5$ is $C(O)R_c$, in which $R_c$ is aryl substituted at the 2- or 3-position with halo or alkoxy.

4. The compound of claim 3, wherein $R_2$ is methyl.

5. The compound of claim 1, wherein the compound is one of the following compounds:

Compound 30

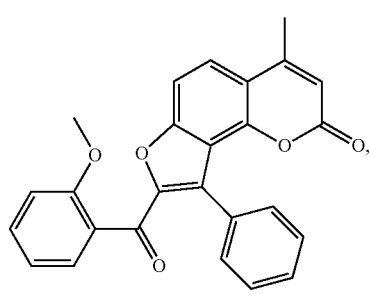

Compound 31

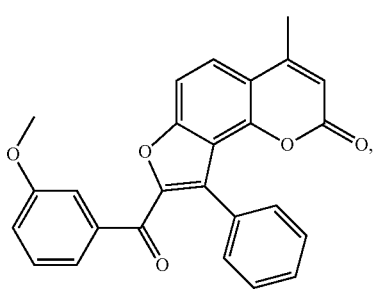

Compound 44

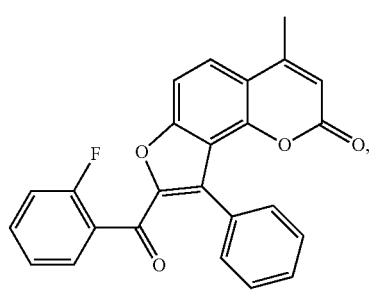

Compound 45

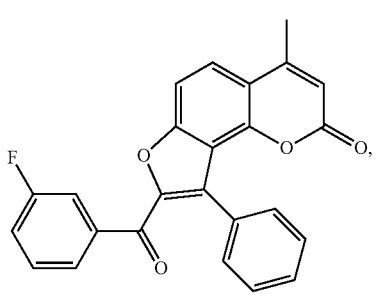

Compound 47

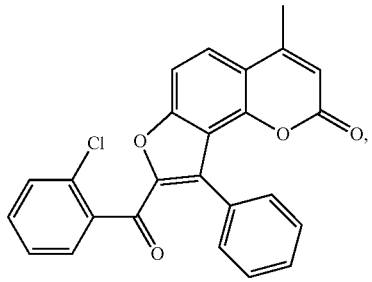

Compound 48

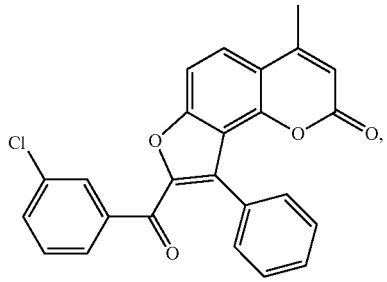

Compound 56

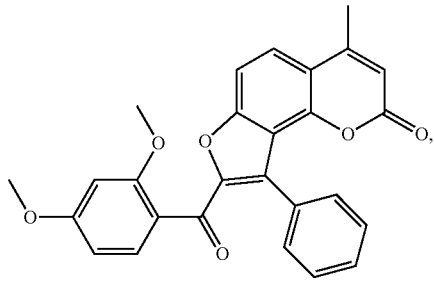

Compound 57

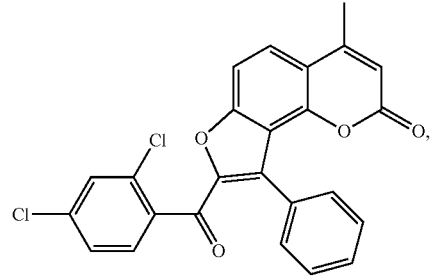

Compound 59

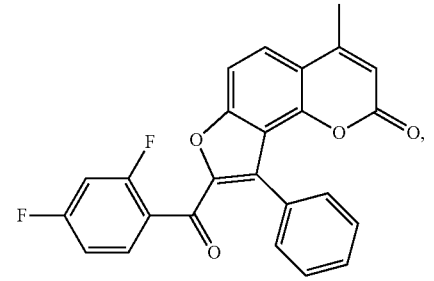

Compound 60
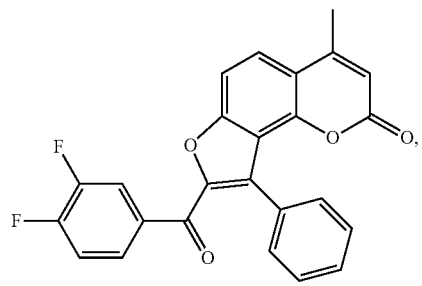
Compound 61
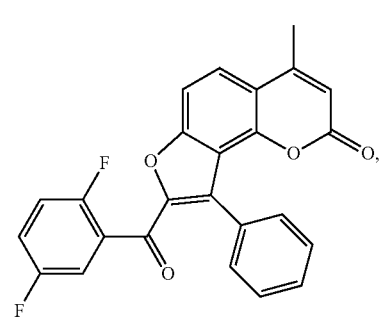
Compound 68
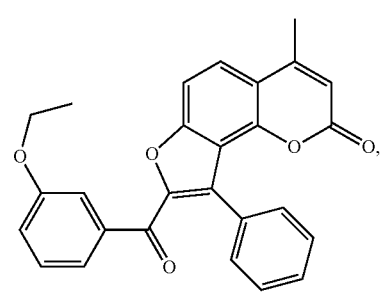
Compound 69
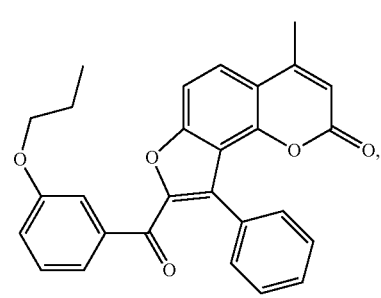
Compound 70
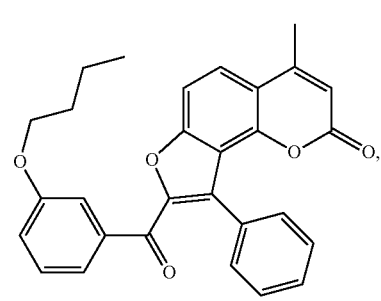
Compound 71
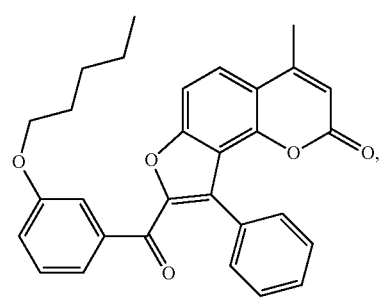
Compound 72
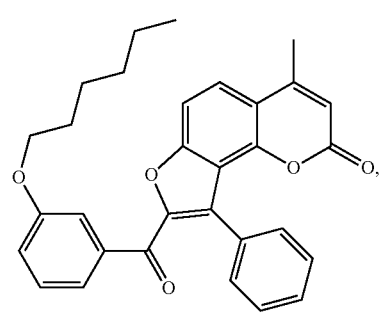
Compound 73
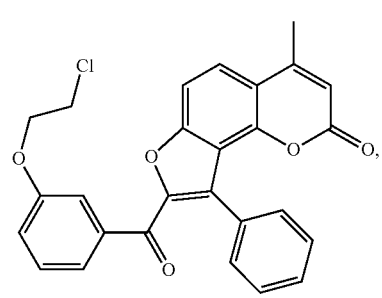
Compuond 74
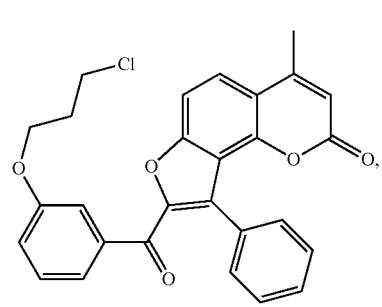
Compound 75
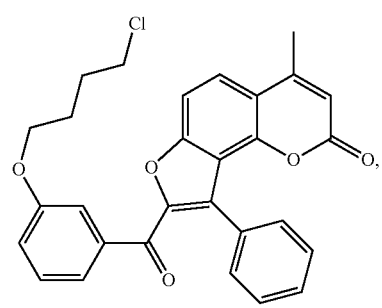

-continued
Compound 76
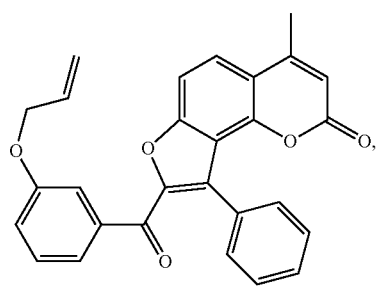
Compound 77
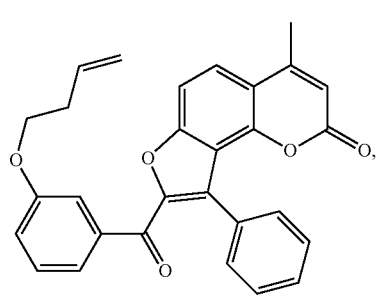
Compound 78
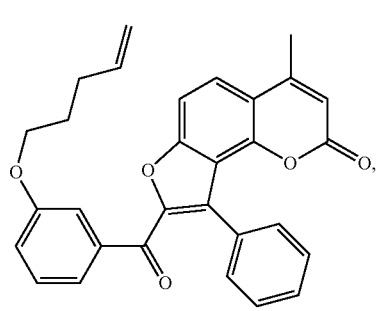
Compound 79
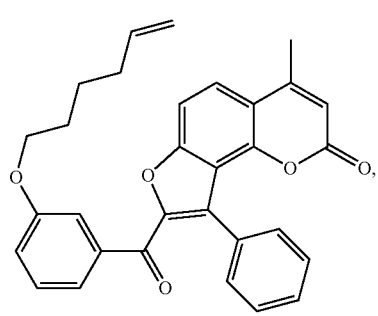
Compound 80
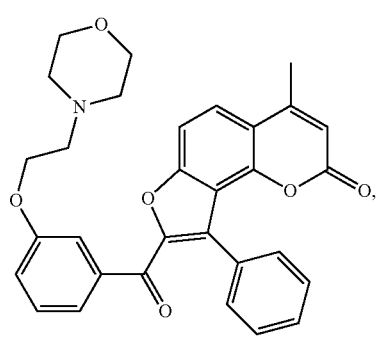
-continued
Compound 81
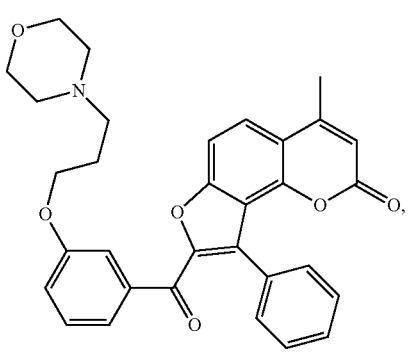
Compound 82
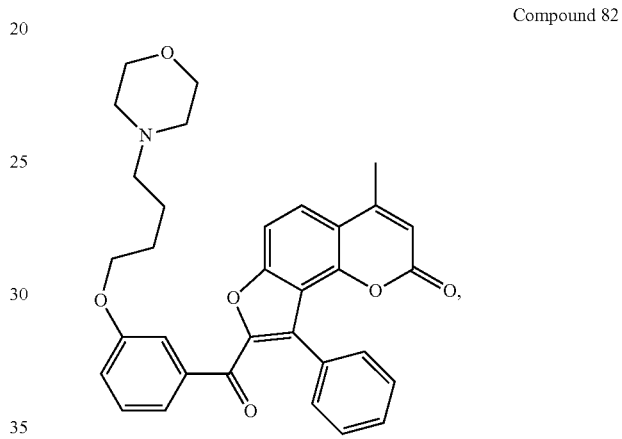
Compound 83
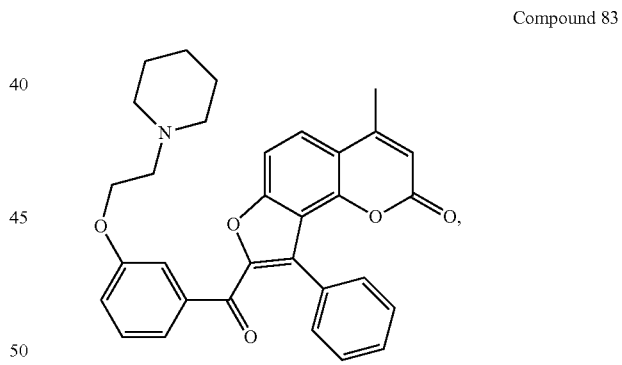
Compound 84
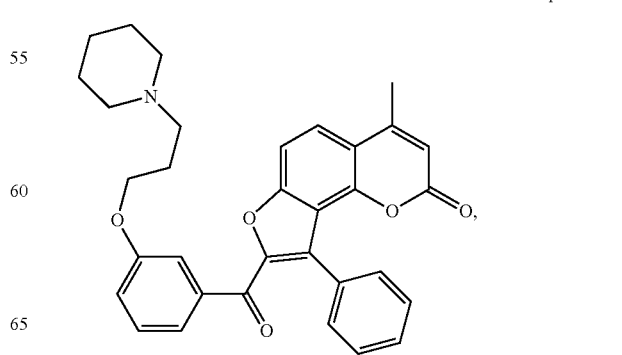

Compound 85
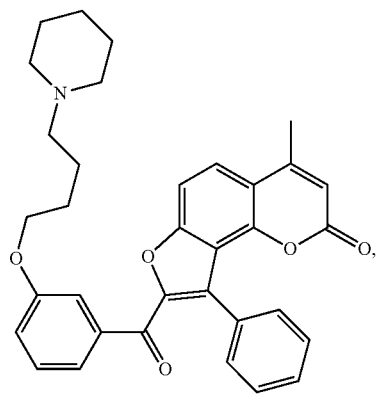
Compound 86
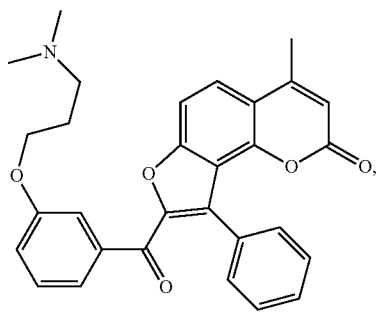
Compound 87
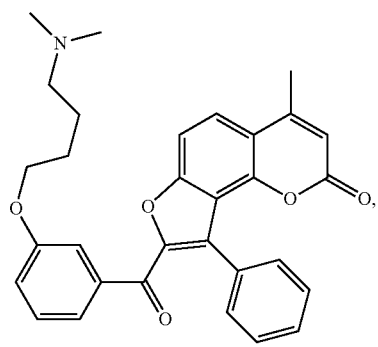
Compound 88
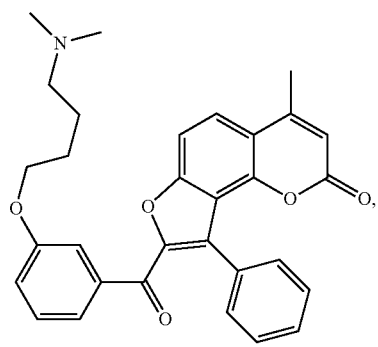
Compound 89
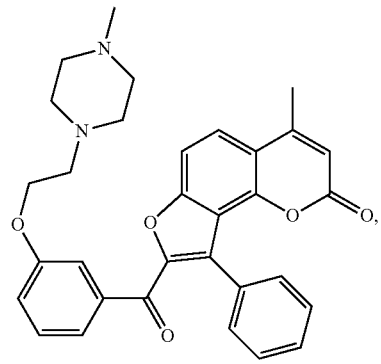
Compound 90
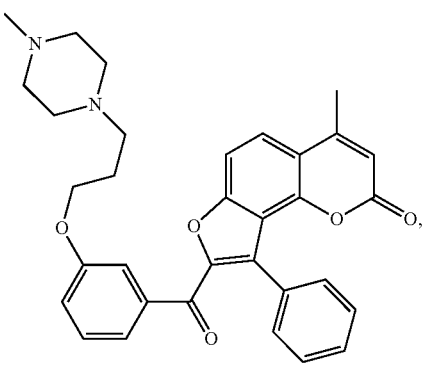
Compound 91
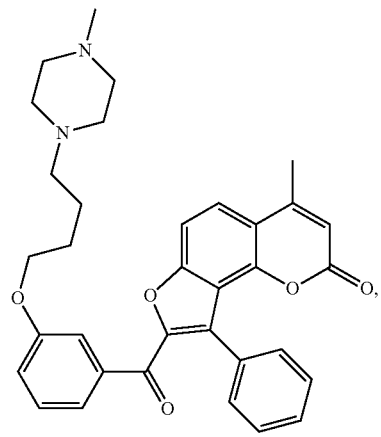
Compound 177
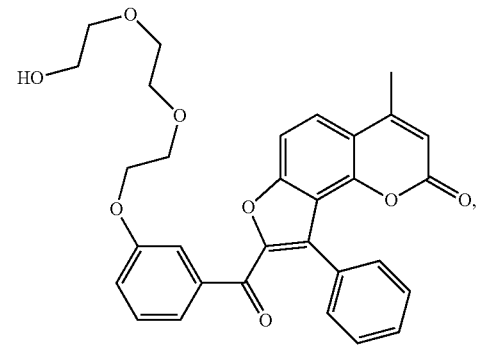

Compound 178
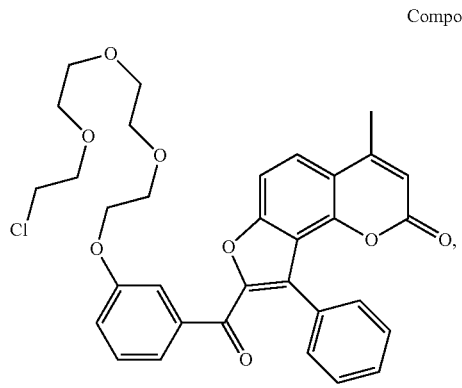
Compound 179
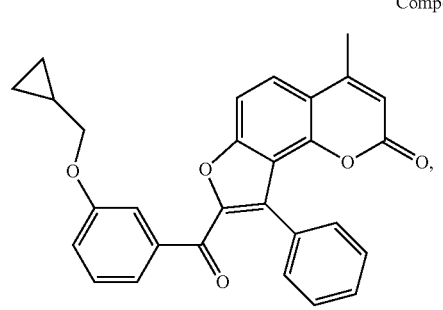
Compound 183
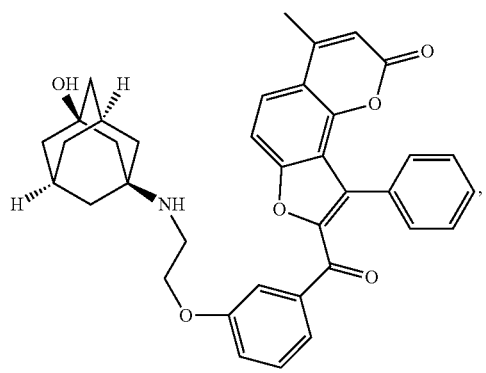
Compound 184
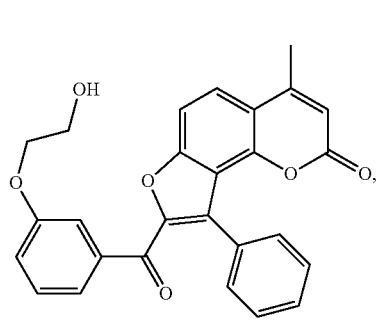
Compound 185
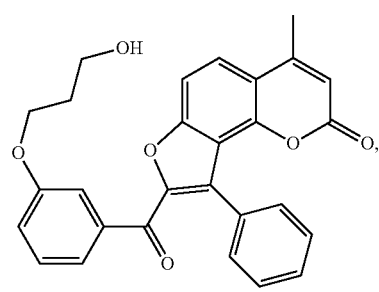
Compound 186
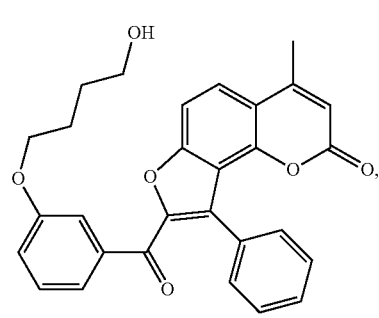
Compound 187
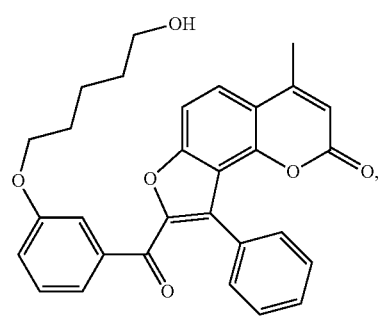
Compound 188
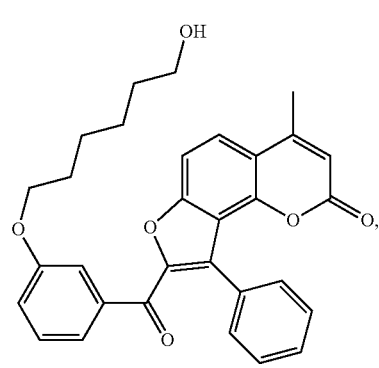
Compound 189
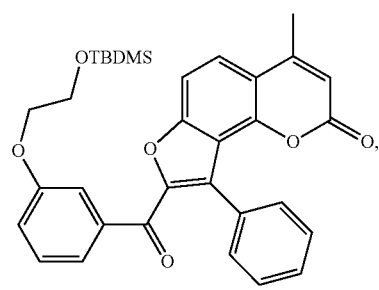

Compound 190
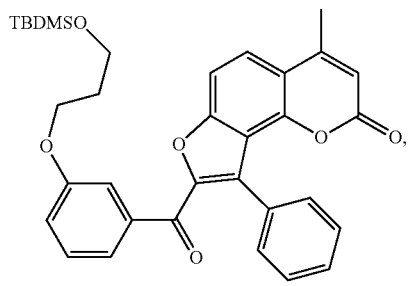
Compound 191
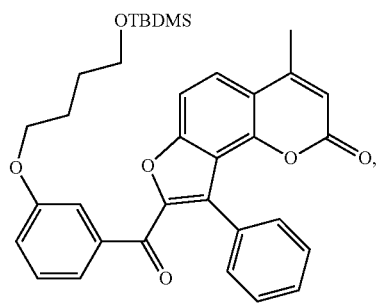
Compound 192
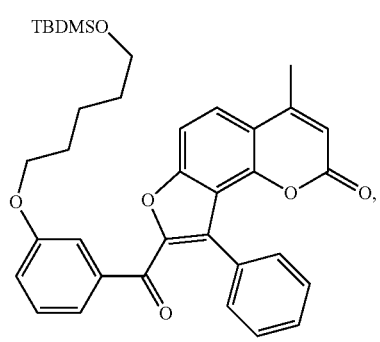
Compound 193
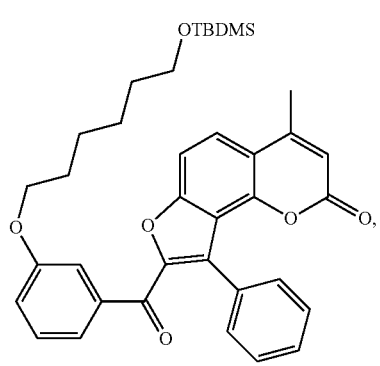
Compound 194
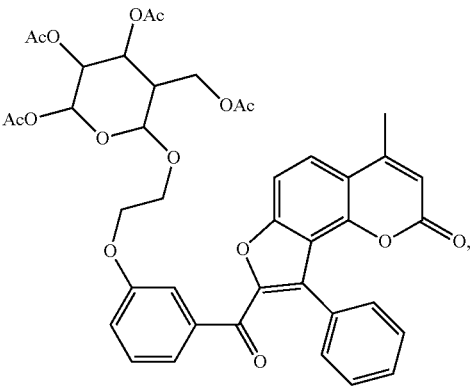
Compound 195
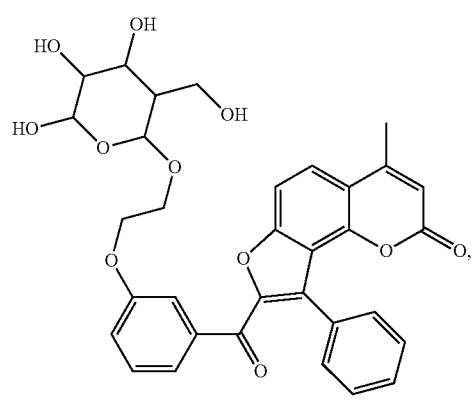
Compound 196
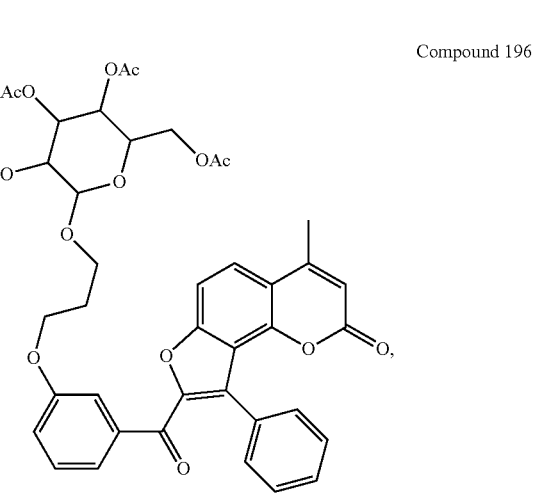

Compound 197
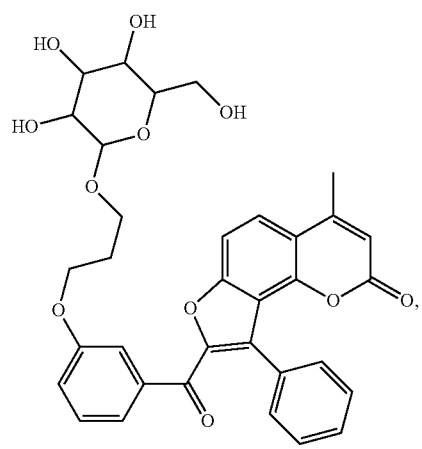
Compound 199
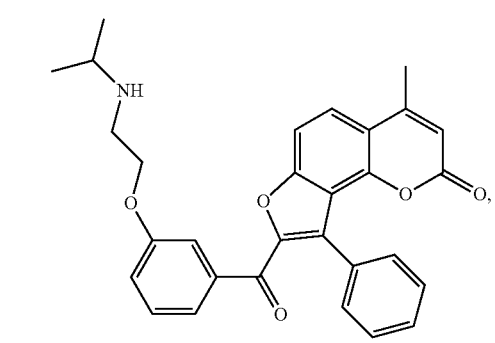
Compound 200
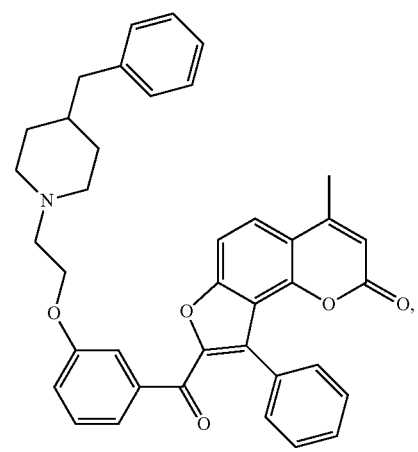
Compound 233
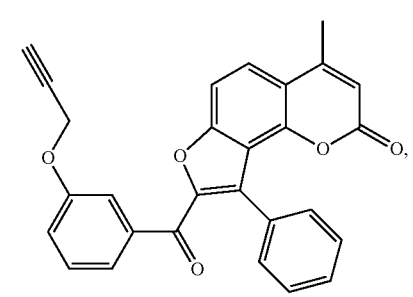
Compound 236
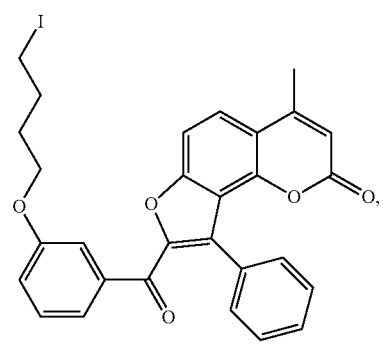
Compound 237
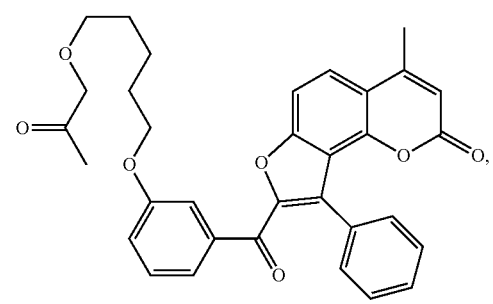
Compound 240
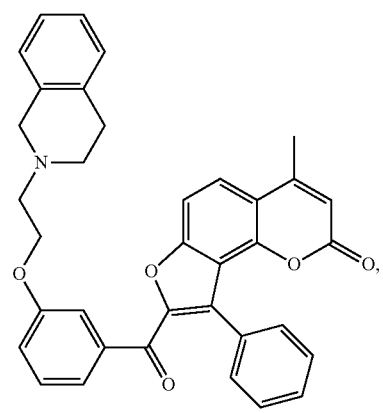
Compound 241
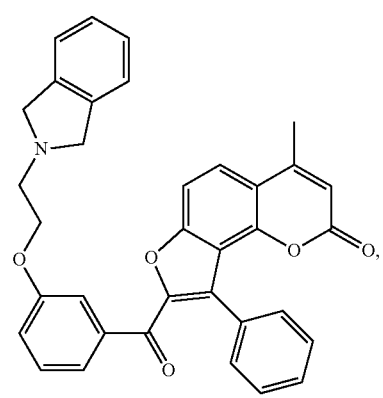

Compound 242
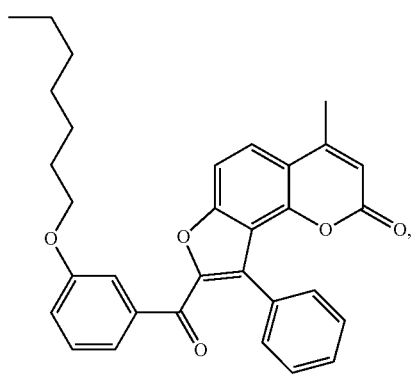
Compound 243
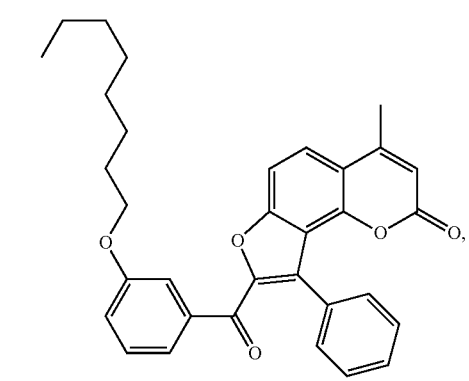
Compound 245
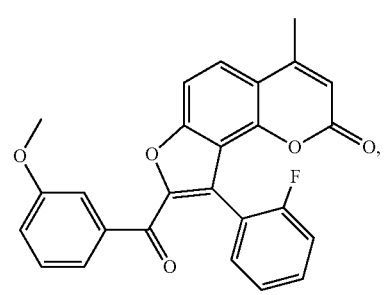
Compound 246
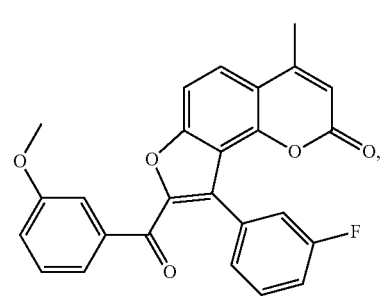
Compound 247
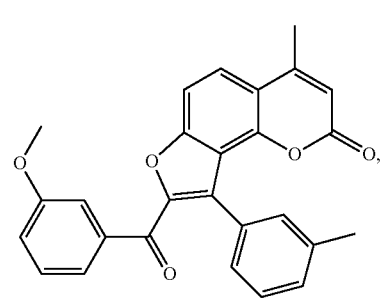
Compound 250
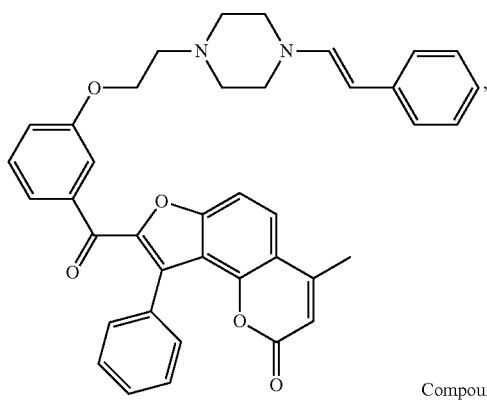
Compound 252
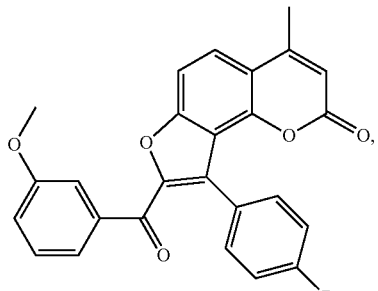
Compound 256
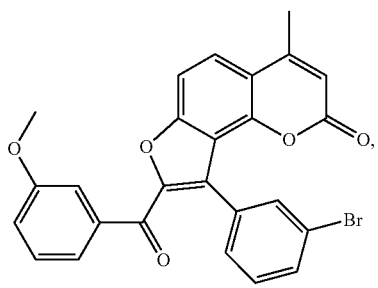
Compound 260
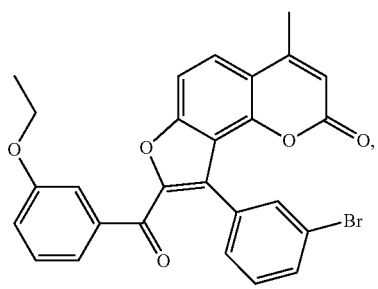
Compound 261
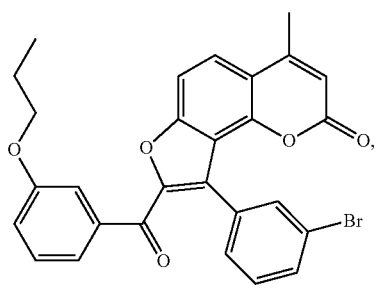

Compound 262
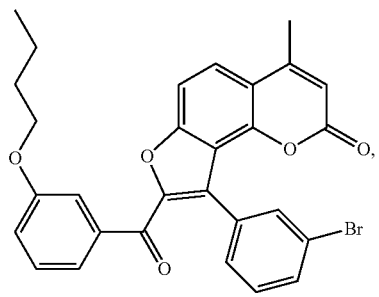 and
Compound 263
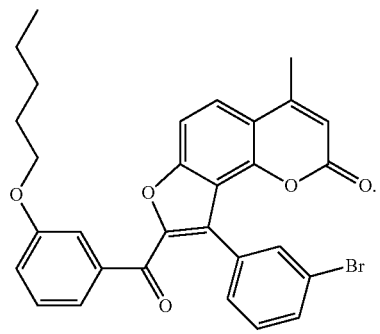
* * * * *